United States Patent
Dales et al.

(10) Patent No.: US 9,187,426 B2
(45) Date of Patent: Nov. 17, 2015

(54) ORGANIC COMPOUNDS

(75) Inventors: Natalie Dales, Cambridge, MA (US); Zaihui Zhang, Burnaby (CA); Jianmin Fu, Burnaby (CA); Duanjie Hou, Burnaby (CA); Shaoyi Sun, Burnaby (CA); Vishnumurthy Kodumuru, Burnaby (CA); Natalia Pokrovskaia, Burnaby (CA)

(73) Assignees: Novartis AG, Basel (CH); Xenon Pharmaceuticals, Burnaby, BC (CA)

(*) Notice: Subject to any disclaimer, the term of this patent is extended or adjusted under 35 U.S.C. 154(b) by 180 days.

(21) Appl. No.: 13/000,413

(22) PCT Filed: Jun. 25, 2009

(86) PCT No.: PCT/EP2009/057998
§ 371 (c)(1),
(2), (4) Date: Dec. 21, 2010

(87) PCT Pub. No.: WO2009/156484
PCT Pub. Date: Dec. 30, 2009

(65) Prior Publication Data
US 2011/0105530 A1 May 5, 2011

Related U.S. Application Data

(60) Provisional application No. 61/076,443, filed on Jun. 27, 2008.

(51) Int. Cl.
| | |
|---|---|
| C07D 401/14 | (2006.01) |
| A61K 31/4439 | (2006.01) |
| C07D 213/81 | (2006.01) |
| A61K 31/444 | (2006.01) |
| C07D 401/04 | (2006.01) |
| C07D 409/12 | (2006.01) |
| C07D 413/04 | (2006.01) |
| C07D 413/14 | (2006.01) |
| C07D 417/14 | (2006.01) |

(52) U.S. Cl.
CPC ............ *C07D 213/81* (2013.01); *A61K 31/444* (2013.01); *A61K 31/4439* (2013.01); *C07D 401/04* (2013.01); *C07D 401/14* (2013.01); *C07D 409/12* (2013.01); *C07D 413/04* (2013.01); *C07D 413/14* (2013.01); *C07D 417/14* (2013.01)

(58) Field of Classification Search
CPC .......................... C07D 401/14; A61K 31/4439
USPC ........................................ 546/256; 514/333
See application file for complete search history.

(56) References Cited

U.S. PATENT DOCUMENTS

| | | | |
|---|---|---|---|
| 4,600,430 | A | 7/1986 | Abdulla et al. |
| 6,004,963 | A | 12/1999 | Zimmer et al. |
| 7,615,565 | B2 | 11/2009 | Huth et al. |

FOREIGN PATENT DOCUMENTS

| | | |
|---|---|---|
| EP | 0719773 | 7/1996 |
| JP | S6133172 | 2/1986 |
| JP | H0249725 | 2/1990 |
| JP | 2004107323 | 4/2004 |
| WO | 9601821 | 1/1996 |
| WO | 0058360 | 10/2000 |
| WO | 0123420 | 4/2001 |
| WO | 0162954 | 8/2001 |
| WO | 0194342 | 12/2001 |
| WO | 0226944 | 4/2002 |
| WO | 03057220 | 7/2003 |
| WO | 2004009558 | 1/2004 |
| WO | 2004013102 | 2/2004 |
| WO | 2006/034446 A2 | 3/2006 |
| WO | 2006034440 | 3/2006 |
| WO | 2007/130075 A1 | 11/2007 |

OTHER PUBLICATIONS

Dorwald, Side Reactions in Organic Synthesis, 2005, Wiley: VCH Weinheim Preface, pp. 1-15 & Chapter 8, pp. 279-308.*
Dobrzyn et al. I, "Stearoyl-CoA desaturase, etc.," Biochimica et Biophysica Acts 1797 (2010): 1189-1194.*
Dobrzyn et al II, "Metabolic reprogramming, etc.," Progress in Lipid Research 57 (2015): 1-12.*
Chow et al., "Estimated plasma, etc.," Metabolism Clinical and Experimental 62 (2013) 100-108.*
Merino et al., "Genetic variation, etc.," Lipids in Health and Disease 2010, 9:63, 1-14.*
Cohen et al., "Leptin and the, etc.," J. Nutr. 134: 2455S-2463S, 2004.*
Hodson et al, "Stearoly, etc.," Progress in Lipid Research 52 (2013) 15-42.*
de Antueno et al., Lipids, 28(4):285-290 (1993).
Binczek et al., Biol. Chem., 388(4):405-418 (2007).
Bundgaard, Design of Prodrugs, Chapter I, pp. 7-9 and 21-24 (1985).
Clark et al., Dermatol. Clin., 25(2):137-146 (2007).
Crossley et al., J. Chem., 1:2327-2330 (1974).
Deng et al., Synthesis, 16:2445-2449 (2001).
Geiger, Dermatology, 191(4):305-310 (1995).
Ghibaudi et al., Obes. Res., 10:956-963 (2002).
Grundy et al., Cardiol. Rev., 13(6):322-327 (2006).
Jeffcoat et al., Eur. J. Biochem., 101(2):439-445 (1979).
Miyazaki, J. Nutr., 131(9):2260-2268 (2001).
Patel, Expert Opin Investig Drugs., 12(4):623-633 (2003).
Shanklin, Proc. Natl. Acad. Sci. USA, 88:2510-2514 (1991).
Zheng et al., Nat. Genet., 23:268-270 (1999).

* cited by examiner

*Primary Examiner* — Patricia L Morris
(74) *Attorney, Agent, or Firm* — Joshua K. Roth

(57) ABSTRACT

The present invention provides heterocyclic derivatives that modulate the activity of stearoyl-CoA desaturase. Methods of using such derivatives to modulate the activity of stearoyl-CoA desaturase and pharmaceutical compositions comprising such derivatives are also encompassed.

2 Claims, No Drawings

ORGANIC COMPOUNDS

This application is the National Stage of Application No. PCT/EP09/057998, filed on Jun. 25, 2009, which claims benefit under 35 U.S.C. §119(e) of U.S. Provisional Application No. 61/076,443, filed Jun. 27, 2008. The contents of National Stage Application No. PCT/EP09/057998 and U.S. Provisional Application No. 61/076,443 are incorporated herein by reference in their entirety.

The present invention relates generally to the field of inhibitors of stearoyl-CoA desaturase, such as heterocyclic derivatives, and uses for such compounds in treating and/or preventing various human diseases, including those mediated by stearoyl-CoA desaturase (SCD) enzymes, preferably SCD1, especially diseases related to elevated lipid levels, cardiovascular disease, diabetes, obesity, metabolic syndrome, dermatological disorders and the like.

Acyl desaturase enzymes catalyze the formation of a double bond in fatty acids derived from either dietary sources or de novo synthesis in the liver. In mammals, at least three fatty acid desaturases exists, each with differing specificity: delta-9, delta-6, and delta-5, which introduce a double bond at the 9-10, 6-7, and 5-6 positions respectively.

Stearoyl-CoA desaturases (SCDs) act with cofactors (other agents) such as NADPH, cytochrome b5, cytochrome b5 reductase, Fe, and molecular $O_2$ to introduce a double bond into the C9-C10 position (delta 9) of saturated fatty acids, when conjugated to Coenzyme A (CoA). The preferred substrates are palmitoyl-CoA (16:0) and stearoyl-CoA (18:0), which are converted to palmitoleoyl-CoA (16:1) and oleyl-CoA (18:1), respectively. The resulting mono-unsaturated fatty acids are substrates for further metabolism by fatty acid elongases or incorporation into phospholipids, triglycerides, and cholesterol esters. A number of mammalian SCD genes have been cloned. For example, two genes have been identified in humans (hSCD1 and hSCD5) and four SCD genes have been isolated from mouse (SCD1, SCD2, SCD3, and SCD4). While the basic biochemical role of SCD has been known in rats and mice since the 1970s (Jeffcoat, R. et al., *Eur. J. Biochem.* (1979), Vol. 101, No. 2, pp. 439-445; de Antueno, R. et al., *Lipids* (1993), Vol. 28, No. 4, pp. 285-290), it has only recently been directly implicated in human disease processes.

The two human SCD genes have been previously described: hSCD1 by Brownlie et. al., PCT published patent application, WO 01/62954, and hSCD5 by Brownlie, PCT published patent application, WO 02/26944.

The present invention solves this problem by presenting new drug-like classes of compounds that are useful in modulating SCD activity and regulating lipid levels, especially plasma lipid levels, and which are useful in the treatment of SCD-mediated diseases such as diseases related to dyslipidemia and disorders of lipid metabolism, especially diseases related to elevated lipid levels, cardiovascular disease, diabetes, obesity, metabolic syndrome, dermatological disorders and the like.

The present invention provides heterocyclic derivatives that modulate the activity of stearoyl-CoA desaturase. Methods of using such derivatives to modulate the activity of stearoyl-CoA desaturase and pharmaceutical compositions comprising such derivatives are also encompassed.

Accordingly, in one aspect, the invention provides compounds of Formula (I):

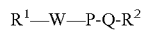
(I)

wherein P is

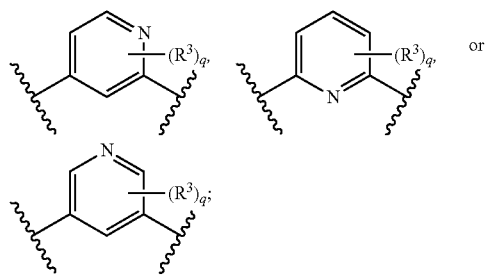

Q is

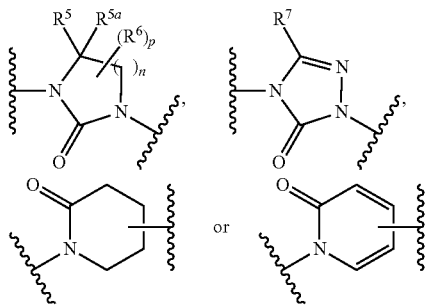

W is selected from —N(R$^8$)C(O)—, —C(O)N(R$^8$)— or a direct bond;
n is 1, 2, or 3;
p is 0, 1, 2, to 2n;
q is 0, 1, 2, or 3;
R$^1$ is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl, or heteroarylalkyl;
R$^2$ is hydrogen, alkyl, alkenyl, alkynyl, alkoxy, hydroxy, hydroxyalkyl, alkoxyalkyl, cycloalkyl, cycloalkylalkyl, aryl, haloalkyl, aralkyl, aralkyloxy, heterocyclyl, heterocyclylalkyl, heteroaryl or heteroarylalkyl;
R$^3$ is alkyl, alkenyl, alkynyl, alkoxy, hydroxyalkyl, alkoxyalkyl, cycloalkyl, cycloalkylalkyl, heterocyclyl, aryl, aralkyl, heteroaryl, halo, haloalkyl, trifluoromethoxyl, cyano, hydroxy, or —N(R$^8$)$_2$;
R$^5$ and R$^{5a}$ are independently selected from hydrogen, alkyl, haloalkyl, hydroxy, hydroxyalkyl, alkoxy, cycloalkylalkyl or aralkyl;
or R$^5$ and R$^{5a}$ are together to form an oxo (=O) group, or to form a cycloakyl;
R$^6$ is alkyl, aryl, cycloalkyl, heteroaryl, heterocyclyl, hydroxyalkyl, haloalkyl, alkoxy, cycloalkylalkyl, or aralkyl;
or R$^5$ and R$^6$ on adjacent carbons are together to form a cycloakyl, or to form an aryl;
R$^7$ is hydrogen, alkyl, haloalkyl, aryl, cycloalkyl, heteroaryl, heterocyclyl, hydroxyalkyl, cycloalkylalkyl or aralkyl; and
R$^8$ is hydrogen, alkyl, hydroxyalkyl, cycloalkylalkyl, aryl, heteroaryl, heterocyclyl or aralkyl;
a stereoisomer, enantiomer or tautomer thereof, a pharmaceutically acceptable salt thereof, a pharmaceutical composition thereof or a prodrug thereof.

In another aspect, the invention provides methods of treating an SCD-mediated disease or condition in a mammal, preferably a human, wherein the methods comprise administering to the mammal in need thereof a therapeutically effective amount of a compound of the invention as set forth above.

In another aspect, the invention provides compounds or pharmaceutical compositions useful in treating, preventing and/or diagnosing a disease or condition relating to SCD biological activity such as the diseases encompassed by cardiovascular disorders and/or metabolic syndrome (including dyslipidemia, insulin resistance and obesity).

In another aspect, the invention provides compounds or pharmaceutical compositions useful in treating, preventing and/or diagnosing a disease or condition relating to SCD biological activity such as the diseases encompassed by dermatological disorders including acne.

In another aspect, the invention provides methods of preventing or treating a disease or condition related to elevated lipid levels, such as plasma lipid levels, especially elevated triglyceride or cholesterol levels, in a patient afflicted with such elevated levels, comprising administering to said patient a therapeutically or prophylactically effective amount of a composition as disclosed herein. The present invention also relates to novel compounds having therapeutic ability to reduce lipid levels in an animal, especially triglyceride and cholesterol levels.

In another aspect, the invention provides pharmaceutical compositions comprising the compounds of the invention as set forth above, and pharmaceutically acceptable excipients. In one embodiment, the present invention relates to a pharmaceutical composition comprising a compound of the invention in a pharmaceutically acceptable carrier and in an amount effective to modulate triglyceride level, or to treat diseases related to dyslipidemia and disorders of lipid metabolism, when administered to an animal, preferably a mammal, most preferably a human patient. In an embodiment of such composition, the patient has an elevated lipid level, such as elevated plasma triglycerides or cholesterol, before administration of said compound and said compound is present in an amount effective to reduce said lipid level.

In another aspect, the invention provides methods for treating a patient for, or protecting a patient from developing, a disease or condition mediated by stearoyl-CoA desaturase (SCD), which methods comprise administering to a patient afflicted with such disease or condition, or at risk of developing such disease or condition, a therapeutically effective amount of a compound that inhibits activity of SCD in a patient when administered thereto.

In another aspect, the invention provides methods for treating a range of diseases involving lipid metabolism and/or lipid homeostasis utilizing compounds identified by the methods disclosed herein. In accordance therewith, there is disclosed herein a range of compounds having said activity, based on a screening assay for identifying, from a library of test compounds, a therapeutic agent which modulates the biological activity of said SCD and is useful in treating a human disorder or condition relating to serum levels of lipids, such as triglycerides, VLDL, HDL, LDL, and/or total cholesterol.

DEFINITIONS

Certain chemical groups named herein are preceded by a shorthand notation indicating the total number of carbon atoms that are to be found in the indicated chemical group. For example, $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

Accordingly, as used in the specification and appended claims, unless specified to the contrary, the following terms have the meaning indicated:

"Cyano" refers to the —CN radical;
"Hydroxy" refers to the —OH radical;
"Nitro" refers to the —NO$_2$ radical;
"Amino" refers to the —NR$^{14}$ or NR$^{15}$ radical;
"Mercapto" refers to the —SR radical;
"Acid" refers to the —COOH radical;
"Trifluoromethyl" refers to the —CF$_3$ radical;
"Trifluoromethoxyl" refers to the —OCF$_3$ radical;

"Alkyl" refers to a straight or branched hydrocarbon chain radical consisting solely of carbon and hydrogen atoms, containing no unsaturation, having from one to twelve carbon atoms, preferably one to eight carbon atoms, one to seven carbon atoms, one to six carbon atoms or one to four carbon atoms, and which is attached to the rest of the molecule by a single bond, e.g., methyl, ethyl, n-propyl, 1-methylethyl (isopropyl), n-butyl, n-pentyl, 1,1-dimethylethyl (t-butyl), and the like. Unless stated otherwise specifically in the specification, an alkyl group may be optionally substituted by one or more of the following groups: alkyl, alkenyl, halo, haloalkyl, cyano, aryl, cycloalkyl, heterocyclyl, heteroaryl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)(S(O)$_t$R$^{16}$), —SR$^{16}$, —S(O)$_t$R$^{16}$, —O—Si(R$^{16}$)$_3$ and —S(O)$_t$N(R$^{14}$)$_2$, where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, cycloalkyl, cycloalkylalkyl, aryl, aralkyl (e.g. tolyl), heterocyclyl, heterocyclylalkyl, heteroaryl or heteroarylalkyl; and each t is 1 to 2.

"Alkenyl" refers to a straight or branched hydrocarbon chain radical group consisting solely of carbon and hydrogen atoms, containing at least one double bond, having from two to twelve carbon atoms, preferably two to eight carbon atoms or two to six carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one or more of the following groups: alkyl, alkenyl, halo, haloalkyl, aryl, aralkyl, cycloalkyl, cycloalkylalkyl, heterocyclyl, heterocyclylalkyl, heteroaryl, heteroarylalkyl, —OR$^{14}$, —OC(O)—R$^{14}$N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)(S(O)$_t$R$^{16}$), —SR$^{16}$, —S(O)$_t$R$^{16}$, and —S(O)$_t$N(R$^{14}$)$_2$, where each R$^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; and each R$^{16}$ is alkyl, cycloalkyl, cycloalkylalkyl, aryl, aralkyl, heterocyclyl, heterocyclylalkyl, heteroaryl or heteroarylalkyl; and where each t is 1 to 2.

"Alkylene" refers to a straight or branched divalent hydrocarbon chain consisting solely of carbon and hydrogen atoms, having from one to twelve carbon atoms, and linking the rest of the molecule to a radical group, e.g., methylene, ethylene, propylene, n-butylene, and the like. The alkylene is attached to the rest of the molecule through a single bond and to the radical group through a single bond. The points of attachment of the alkeylene to the rest of the molecule and to the radical group can be through one carbon or any two carbons within the chain. Unless stated otherwise specifically in the specification, an alkylene group may be optionally substituted by one or more of the following groups: alkyl, alkenyl, halo, haloalkyl, aryl, aralkyl, cycloalkyl, cycloalkylalkyl, heterocyclyl, heterocyclylalkyl, heteroaryl, heteroarylalkyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)(S(O)$_t$R$^{16}$), —SR$^{16}$, —S(O)$_t$R$^{16}$, and —S(O)$_t$N(R$^{14}$)$_2$, where each R$^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl; and where each t is 1 to 2.

"Alkynyl" refers to a straight or branched hydrocarbon chain radical group consisting solely of carbon and hydrogen atoms, containing at least one triple bond, having from two to twelve carbon atoms, preferably two to eight carbon atoms or two to six carbon atoms and which is attached to the rest of the molecule by a single bond. Unless stated otherwise specifically in the specification, an alkynyl group may be optionally substituted by one or more of the following groups: alkyl, alkenyl, halo, haloalkyl, aryl, aralkyl, cycloalkyl, cycloalkylalkyl, heterocyclyl, heterocyclylalkyl, heteroaryl, heteroarylalkyl, —OR$^{14}$, —OC(O)—R$^{14}$N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)(S(O)$_t$R$^{16}$), —SR$^{16}$, —S(O)$_t$R$^{16}$, and —S(O)$_t$N(R$^{14}$)$_2$, where each R$^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; and each R$^{16}$ is alkyl, cycloalkyl, cycloalkylalkyl, aryl, aralkyl, heterocyclyl, heterocyclylalkyl, heteroaryl or heteroarylalkyl; and where each t is 1 to 2.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms or two to six carbon atoms, e.g., ethenylene, propenylene, n-butenylene, and the like. Unless stated otherwise specifically in the specification, an alkenylene chain may be optionally substituted by one or more of the following groups: alkyl, alkenyl, halo, cyano, aryl, cycloalkyl, heterocyclyl, heteroaryl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)(S(O)$_t$R$^{16}$), —SR$^{16}$, —S(O)$_t$R$^{16}$, and —S(O)$_t$N(R$^{14}$)$_2$, where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, cycloalkyl, cycloalkylalkyl, aryl, aralkyl, heterocyclyl, heterocyclylalkyl, heteroaryl or heteroarylalkyl; and where each t is 1 to 2.

"Alkynylene" and "alkynylene chain" refer to a straight or branched divalent hydrocarbon chain linking the rest of the molecule to a radical group, consisting solely of carbon and hydrogen, containing at least one triple bond and having from two to twelve carbon atoms or two to six carbon atoms, e.g. propynylene, n-butynylene, and the like. Unless stated otherwise specifically in the specification, an alkynylene chain may be optionally substituted by one or more of the following groups: alkyl, alkenyl, halo, cyano, aryl, cycloalkyl, heterocyclyl, heteroaryl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)(S(O)$_t$R$^{16}$), —SR$^{16}$, —S(O)$_t$R$^{16}$, and —S(O)$_t$N(R$^{14}$)$_2$, where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, cycloalkyl, cycloalkylalkyl, aryl, aralkyl, heterocyclyl, heterocyclylalkyl, heteroaryl or heteroarylalkyl; and where each t is 1 to 2.

"Alkoxy" refers to a radical of the formula —OR$_a$ where R$_a$ is an alkyl radical as generally defined above. The alkyl part of the alkoxy radical may be optionally substituted as defined above for an alkyl radical.

"Alkoxyalkyl" refers to a radical of the formula —R$_a$—O—R$_a$ where each R$_a$ is independently an alkyl radical as defined above. The oxygen atom may be bonded to any carbon in either alkyl radical. Each alkyl part of the alkoxyalkyl radical may be optionally substituted as defined above for an alkyl group.

"Aryl" refers to aromatic monocyclic or multicyclic hydrocarbon ring system consisting only of hydrogen and carbon and containing from six to nineteen carbon atoms, preferably six to ten carbon atoms, where the ring system may be partially saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents selected from the group consisting of alkyl, alkenyl, alkynyl, halo, haloalkyl, cyano, nitro, aryl, aralkyl, cycloalkyl, cycloalkylalkyl, heterocyclyl, heterocyclylalkyl, heteroaryl, heteroarylalkyl, —R$^{15}$—OR$^{14}$, —R$^{15}$—OC(O)—R$^{14}$, —R$^{15}$—N(R$^{14}$)$_2$, —R$^{15}$—C(O)R$^{14}$, —R$^{15}$—C(O)OR$^{14}$, —R$^{15}$—C(O)N(R$^{14}$)$_2$, —R$^{15}$—N(R$^{14}$)C(O)OR$^{16}$, —R$^{15}$—N(R$^{14}$)C(O)R$^{16}$, —R$^{15}$—N(R$^{14}$)(S(O)$_t$R$^{16}$), —R$^{15}$—SR$^{16}$, —R$^{15}$—S(O)$_t$R$^{16}$, and —R$^{15}$—S(O)$_t$N(R$^{14}$)$_2$, where each R$^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; each R$^{15}$ is independently a direct bond or a straight or branched alkylene or alkenylene chain; and each R$^{16}$ is alkyl, haloalkyl, cycloalkyl, cycloalkylalkyl, aryl, aralkyl, heterocyclyl, heterocyclylalkyl, heteroaryl or heteroarylalkyl; and where each t is 1 to 2.

"Aralkyl" refers to a radical of the formula —R$_a$R$_b$ where R$_a$ is an alkyl radical as defined above and R$_b$ is one or more aryl radicals as defined above, e.g., benzyl, diphenylmethyl and the like. The aryl part of the aralkyl radical may be optionally substituted as described above for an aryl group. The alkyl part of the aralkyl radical may be optionally substituted as defined above for an alkyl group.

"Aralkenyl" refers to a radical of the formula —R$_a$R$_b$ where R$_a$ is an alkenylene chain as defined above and R$_b$ is one or more aryl radicals as defined above, which may be optionally substituted as described above. The aryl part of the aralkenyl radical may be optionally substituted as described above for an aryl group. The alkenylene chain of the aralkenyl radical may be optionally substituted as defined above for an alkenyl group.

"Aryloxy" refers to a radical of the formula —OR$_b$ where R$_b$ is an aryl group as defined above. The aryl part of the aryloxy radical may be optionally substituted as defined above.

"Aralkyloxy" refers to a radical of the formula —OR$_b$ where R$_b$ is an aralkyl group as defined above. The aralkyl part of the aralkyloxy radical may be optionally substituted as defined above.

"Cycloalkyl" refers to a stable non-aromatic monocyclic or bicyclic hydrocarbon radical consisting solely of carbon and hydrogen atoms, having from three to fifteen carbon atoms, preferably having from three to twelve carbon atoms or from three to seven atoms, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents selected from the group consisting of alkyl, alkenyl, alkynyl, halo, haloalkyl, cyano, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_tR^{16})$, —$R^{15}$—$SR^{16}$, —$R^{15}$—$S(O)_tR^{16}$, and —$R^{15}$—$S(O)_tN(R^{14})_2$, where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl; and where each t is 1 to 2.

"Cycloalkylalkyl" refers to a radical of the formula —$R_aR_d$ where $R_a$ is an alkyl radical as defined above and $R_d$ is a cycloalkyl radical as defined above. The cycloalkyl part of the cycloalkyl radical may be optionally substituted as defined above for a cycloalkyl radical. The alkyl part of the cycloalkyl radical may be optionally substituted as defined above for an alkyl radical.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heterocyclyl" refers to a stable 3- to 18-membered non-aromatic ring radical which consists of carbon atoms and from one to five heteroatoms selected from the group consisting of nitrogen, oxygen and sulfur, preferably having from two to ten carbon atoms. For purposes of this invention, the heterocyclyl radical may be a monocyclic, bicyclic or tricyclic ring system, which may include fused or bridged ring systems, which may be partially unsaturated; and the nitrogen, carbon or sulfur atoms in the heterocyclyl radical may be optionally oxidized; the nitrogen atom may be optionally alkylated/substituted; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl, homopiperidinyl, homopiperazinyl, and quinuclidinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, cyano, oxo, thioxo, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_tR^{16})$, $R^{15}$—$SR^{16}$, —$R^{15}$—$S(O)_tR^{16}$, and —$R^{15}$—$S(O)_tN(R^{14})_2$, where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl; and where each t is 1 to 2; and where each of the above substituents is unsubstituted.

"Heterocyclylalkyl" refers to a radical of the formula —$R_aR_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"Heteroaryl" refers to a 5- to 18-membered aromatic ring radical which consists of carbon atoms and from one to five heteroatoms selected from the group consisting of nitrogen, oxygen and sulfur, preferably having from one to ten carbon atoms. For purposes of this invention, the heteroaryl radical may be a monocyclic, bicyclic or tricyclic ring system, which may include fused or bridged ring systems, which may be partially saturated; and the nitrogen, carbon or sulfur atoms in the heteroaryl radical may be optionally oxidized; the nitrogen atom may be optionally alkylated/substituted. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl, benzo[b]thiophenyl, benzothiophenyl, benzotriazolyl, benzo[4,6]imidazo[1,2-a]pyridinyl, benzo[c][1,2,5]oxadiazolyl, benzo[c][1,2,5]thiadiazolyl, carbazolyl, cinnolinyl, dibenzofuranyl, furanyl, furanonyl, isoquinolinyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl, alkenyl, alkynyl, halo, haloalkyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_tR^{16})$, $R^{15}$—$SR^{16}$, —$R^{15}$—$S(O)_tR^{16}$, and —$R^{15}$—$S(O)_tN(R^{14})_2$, where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl and where t is 1 to 2.

"Heteroarylalkyl" refers to a radical of the formula —$R_aR_f$ where $R_a$ is an alkylene chain as defined above and $R_f$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"Hydroxyalkyl" refers to a radical of the formula —$R_a$—OH where $R_a$ is an alkyl radical as defined above. The hydroxy group may be attached to the alkyl radical on any carbon within the alkyl radical. The alkyl part of the hydroxyalkyl group may be optionally substituted as defined above for an alkyl group.

"A multi-ring structure" refers to a multicyclic ring system comprised of two to four rings wherein the rings are independently selected from cycloalkyl, aryl, heterocyclyl or heteroaryl as defined above. Each cycloalkyl may be optionally substituted as defined above for a cycloalkyl group. Each aryl may be optionally substituted as defined above for an aryl group. Each heterocyclyl may be optionally substituted as defined above for a heterocyclyl group. Each heteroaryl may be optionally substituted as defined above for a heteroaryl group. The rings may be attached to each other through direct bonds or some or all of the rings may be fused to each other.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood or conversion in the gut or liver. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, Anglican Pharmaceutical Association arid Pergamon Press, 1987.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto or acid group is bonded to any group that, when the prodrug of the compound of the invention is administered to a mammalian subject, cleaves to form a free hydroxy, free amino or free mercapto or acid group, respectively. Examples of prodrugs include, but are not limited to, acetate, formate and benzoate derivatives of alcohol or amides of amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent. A skilled artisan will recognize unstable combinations of substituents.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxoglutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients thereof.

"Therapeutically effective amount" refers to that amount of a compound of the invention which, when administered to a mammal, preferably a human, is sufficient to effect treatment, as defined below, of an SCD-mediated disease or condition in the mammal, preferably a human. The amount of a compound of the invention which constitutes a "therapeutically effective amount" will vary depending on the compound, the condition and its severity, and the age and body weight of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or disorder of interest, and includes: (i) preventing the disease or condition from occurring in a mammal, in particular, when such mammal is predisposed to the condition but has not yet been diagnosed as having it; (ii) inhibiting the disease or condition, i.e., arresting its development; (iii) relieving the disease or condition, i.e., causing regression of the disease or condition; or (iv) reducing the risk of developing the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

The present invention includes all pharmaceutically acceptable isotopically-labeled compounds of the invention wherein one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{31}P$ and $^{32}P$, and sulphur, such as $^{35}S$.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Isotopically-labeled compounds of the invention can generally be prepared by conventional techniques known to those skilled in the art or by processes analogous to those described in the accompanying Examples and Preparations Sections using an appropriate isotopically-labeled reagent in place of the non-labeled reagent previously employed.

The chemical naming protocol and structure diagrams used herein employ and rely on the chemical naming features as utilized by Chemdraw versions 10.0 or 11.0 (available from Cambridgesoft Corp., Cambridge, Mass.) or ISIS draw version 2.5 (available from MDL information systems).

EMBODIMENTS OF THE INVENTION

Throughout this specification and in the claims that follow, unless the context requires otherwise, the word "comprise", or variations such as "comprises", "comprised of", "comprising" or "comprising of", will be understood to imply the inclusion of a stated integer or step or group of integers or steps but not the exclusion of any other integer or step or group of integers or steps and therefore inclusive and open-ended in that additional elements.

Various embodiments of the invention are described below. It will be appreciated that the features specified in each embodiment may be combined with other specified features, to provide further embodiments.

One embodiment of the invention is the compounds of Formula (I)

$$R^1-W-P-Q-R^2 \quad (I)$$

wherein P is

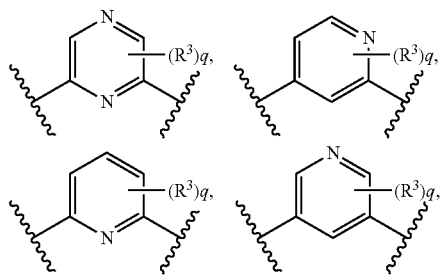

-continued

[chemical structures: pyridazine with (R³)q, pyrimidine with (R³)q, or pyrimidine with (R³)q]

Q is

[chemical structures showing heterocyclic groups with R⁵, R⁵ᵃ, (R⁶)p, R⁷ substituents; urea-type, imidazolone-type]

[triazolone structure with R⁷, or piperidinone structure]

[pyridinone structure]

W is selected from —N(R⁸)C(O)—, —C(O)N(R⁸)— or a direct bond;
n is 1, 2, or 3;
p is 0, 1, 2, to 2n;
q is 0, 1, 2, or 3;
R¹ is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl, or heteroarylalkyl;
R² is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl or heteroarylalkyl;
R³ is alkyl, alkenyl, alkynyl, alkoxy, hydroxyalkyl, alkoxyalkyl, cycloalkyl, cycloalkylalkyl, heterocyclyl, aryl, aralkyl, heteroaryl, halo, haloalkyl, trifluoromethoxyl, cyano, hydroxyl, or —N(R⁸)₂;
R⁵ and R⁵ᵃ are independently selected from hydrogen, alkyl, haloalkyl, hydroxyl, hydroxyalkyl, alkoxy, cycloalkylalkyl or aralkyl;
or R⁵ and R⁵ᵃ are together to form an oxo (═O) group, or to form a cycloaklyl;
R⁶ is alkyl, aryl, cycloalkyl, heteroaryl, heterocyclyl, hydroxyalkyl, haloalkyl, alkoxy, cycloalkylalkyl, or aralkyl;
or R⁵ and R⁶ on adjacent carbon are together to form a cycloaklyl, or to form an aryl;
R⁷ is hydrogen, alkyl, haloalkyl, aryl, cycloalkyl, heteroaryl, heterocyclyl, hydroxyalkyl, cycloalkylalkyl or aralkyl; and R⁸ is hydrogen, alkyl, hydroxyalkyl, cycloalkylalkyl, aryl, heteroaryl, heterocyclyl or aralkyl;
a stereoisomer, enantiomer or tautomer thereof, a pharmaceutically acceptable salt thereof, a pharmaceutical composition thereof or a prodrug thereof.

One embodiment of the invention are the compounds of Formula (I)

$$R^1—W—P-Q-R^2 \quad (I)$$

wherein P is

[chemical structures: pyridine with (R³)q variants, or]

[pyridine structure with (R³)q]

Q is

[chemical structures showing R⁵, R⁵ᵃ, (R⁶)p group and R⁷ triazolone]

[piperidinone structure, or pyridinone structure]

W is —N(R⁸)C(O)—, —C(O)N(R⁸)— or a direct bond;
n is 1, 2, or 3;
p is 0, 1, 2, to 2n;
q is 0, 1, 2, or 3;
R¹ is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl, or heteroarylalkyl;
R² is hydrogen, alkyl, alkenyl, alkynyl, alkoxy, hydroxy, hydroxyalkyl, alkoxyalkyl, cycloalkyl, cycloalkylalkyl, aryl, haloalkyl, aralkyl, aralkyloxy, heterocyclyl, heterocyclylalkyl, heteroaryl or heteroarylalkyl;
R³ is alkyl, alkenyl, alkynyl, alkoxy, hydroxyalkyl, alkoxyalkyl, cycloalkyl, cycloalkylalkyl, heterocyclyl, aryl, aralkyl, heteroaryl, halo, haloalkyl, trifluoromethoxyl, cyano, hydroxy, or —N(R⁸)₂;
R⁵ and R⁵ᵃ are independently selected from hydrogen, alkyl, haloalkyl, hydroxy, hydroxyalkyl, alkoxy, cycloalkylalkyl or aralkyl;
or R⁵ and R⁵ᵃ are together to form an oxo (═O) group, or to form a cycloaklyl;
R⁶ is alkyl, aryl, cycloalkyl, heteroaryl, heterocyclyl, hydroxyalkyl, haloalkyl, alkoxy, cycloalkylalkyl, or aralkyl;
or R⁵ and R⁶ on adjacent carbons are together to form a cycloaklyl, or to form an aryl;

R⁷ is hydrogen, alkyl, haloalkyl, aryl, cycloalkyl, heteroaryl, heterocyclyl, hydroxyalkyl, cycloalkylalkyl or aralkyl; and R⁸ is hydrogen, alkyl, hydroxyalkyl, cycloalkylalkyl, aryl, heteroaryl, heterocyclyl or aralkyl;

a stereoisomer, enantiomer or tautomer thereof, a pharmaceutically acceptable salt thereof, a pharmaceutical composition thereof or a prodrug thereof.

In another embodiment of the invention are the compounds of Formula (I), wherein W is —N(R⁸)C(O)—, and R¹ is hydrogen, alkyl, aryl, aralkyl or heteroarylalkyl.

In another embodiment of the invention are the compounds of Formula (I), wherein W is a direct bond and R¹ is aryl or heteroaryl.

In another embodiment of the invention are the compounds of Formula (I), wherein R¹ is hydrogen, C₁-C₇alkyl, C₂-C₆alkenyl, C₂-C₆alkynyl, C₁-C₇alkoxy, hydroxyC₁-C₄alkyl, alkoxyC₁-C₄alkyl, C₃-C₇cycloalkyl, C₃-C₇cycloalkylC₁-C₄alkyl, C₆-C₁₀aryl, haloC₁-C₄alkyl, aralkyl, C₂-C₁₀heterocyclyl, C₂-C₁₀heterocyclylC₁-C₄alkyl, C₁-C₁₀heteroaryl, or C₁-C₁₀heteroarylC₁-C₄alkyl;

R² is hydrogen, C₁-C₇alkyl, C₂-C₆alkenyl, C₂-C₆alkynyl, C₁-C₇alkoxy, hydroxy, hydroxyC₁-C₄alkyl, alkoxyC₁-C₄alkyl, C₃-C₇cycloalkyl, C₃-C₇cycloalkylC₁-C₄alkyl, C₆-C₁₀aryl, haloC₁-C₄alkyl, aralkyl, aralkyloxy, C₂-C₁₀heterocyclyl, C₂-C₁₀heterocyclylC₁-C₄alkyl, C₁-C₁₀heteroaryl, or C₁-C₁₀heteroarylC₁-C₄alkyl;

R³ is C₁-C₇alkyl, C₂-C₆alkenyl, C₂-C₆alkynyl, C₁-C₇alkoxy, hydroxyC₁-C₄alkyl, alkoxyC₁-C₄alkyl, C₃-C₇cycloalkyl, C₃-C₇cycloalkylC₁-C₄alkyl, C₂-C₁₀heterocyclyl, C₆-C₁₀aryl, aralkyl, C₁-C₁₀heteroaryl, halo, haloC₁-C₄alkyl, trifluoromethoxyl, cyano, hydroxy, or —N(R⁸)₂;

R⁵ and R⁵ᵃ are independently selected from hydrogen, C₁-C₇alkyl, haloC₁-C₄alkyl, hydroxy, hydroxyC₁-C₄alkyl, C₁-C₇alkoxy, C₃-C₇cycloalkylC₁-C₄alkyl or aralkyl;

or R⁵ and R⁵ᵃ are together to form an oxo (=O) group, or to form a C₃-C₇cycloalkyl;

R⁶ is C₁-C₇alkyl, C₆-C₁₀aryl, C₃-C₇cycloalkyl, C₁-C₁₀heteroaryl, C₂-C₁₀heterocyclyl, hydroxyC₁-C₄alkyl, haloC₁-C₄alkyl, C₁-C₇alkoxy, C₃-C₇cycloalkylC₁-C₄alkyl, or aralkyl;

or R⁵ and R⁶ on adjacent carbons are together to form a C₃-C₇cycloalkyl, or to form an C₆-C₁₀aryl;

R⁷ is hydrogen, C₁-C₇alkyl, haloC₁-C₄alkyl, C₆-C₁₀aryl, C₃-C₇cycloalkyl, C₁-C₁₀heteroaryl, C₂-C₁₀heterocyclyl, hydroxyC₁-C₄alkyl, C₃-C₇cycloalkylC₁-C₄alkyl or aralkyl; and R⁸ is hydrogen, C₁-C₇alkyl, hydroxyC₁-C₄alkyl, C₃-C₇cycloalkylC₁-C₄alkyl, C₆-C₁₀aryl, C₁-C₁₀heteroaryl, C₂-C₁₀heterocyclyl or aralkyl;

a stereoisomer, enantiomer or tautomer thereof, a pharmaceutically acceptable salt thereof, a pharmaceutical composition thereof or a prodrug thereof.

A subgroup of P for the compounds represented by Formula (I) is

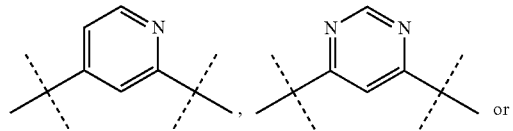

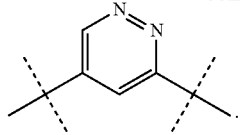

A subgroup of P for the compounds represented by Formula (I) is

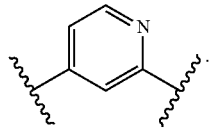 [SMILES: *c1ccnc(*)c1]

A subgroup of R¹ for the compounds represented by Formula (I), wherein W is —N(R⁸)C(O)—, and R¹ is hydrogen, alkyl,

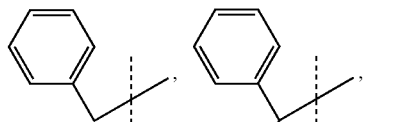

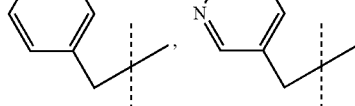

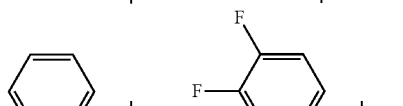

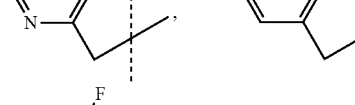

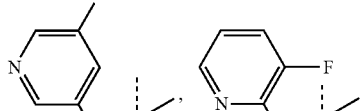

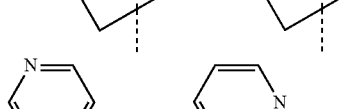

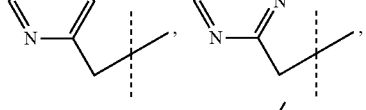

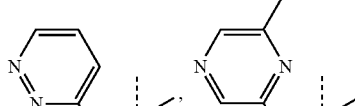

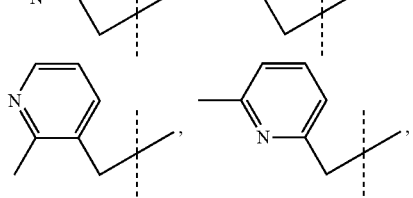

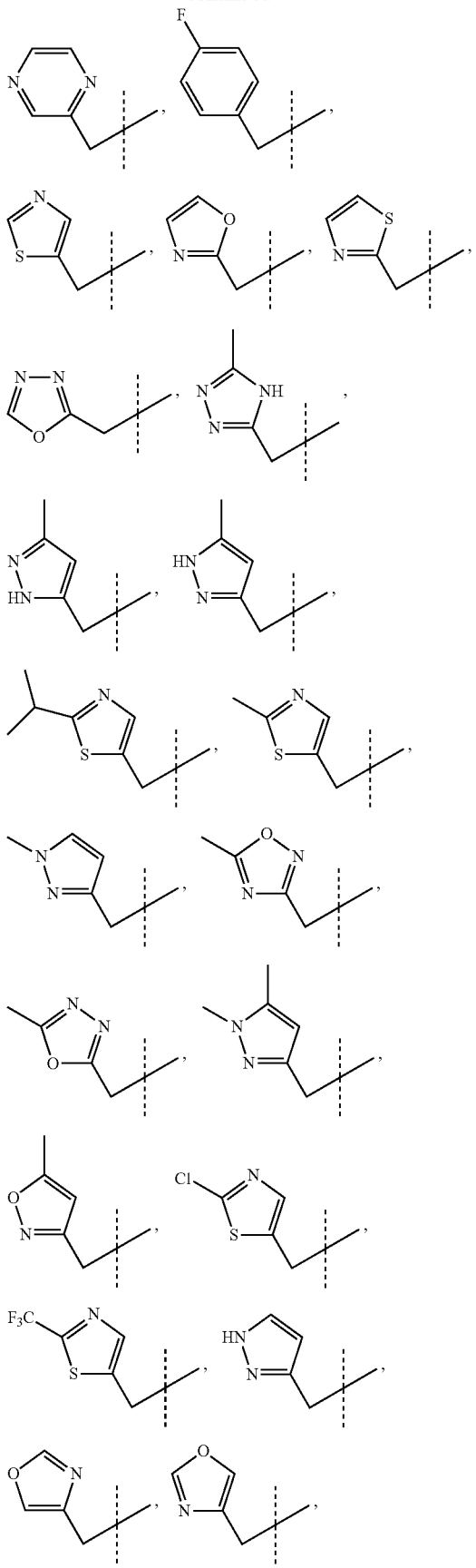
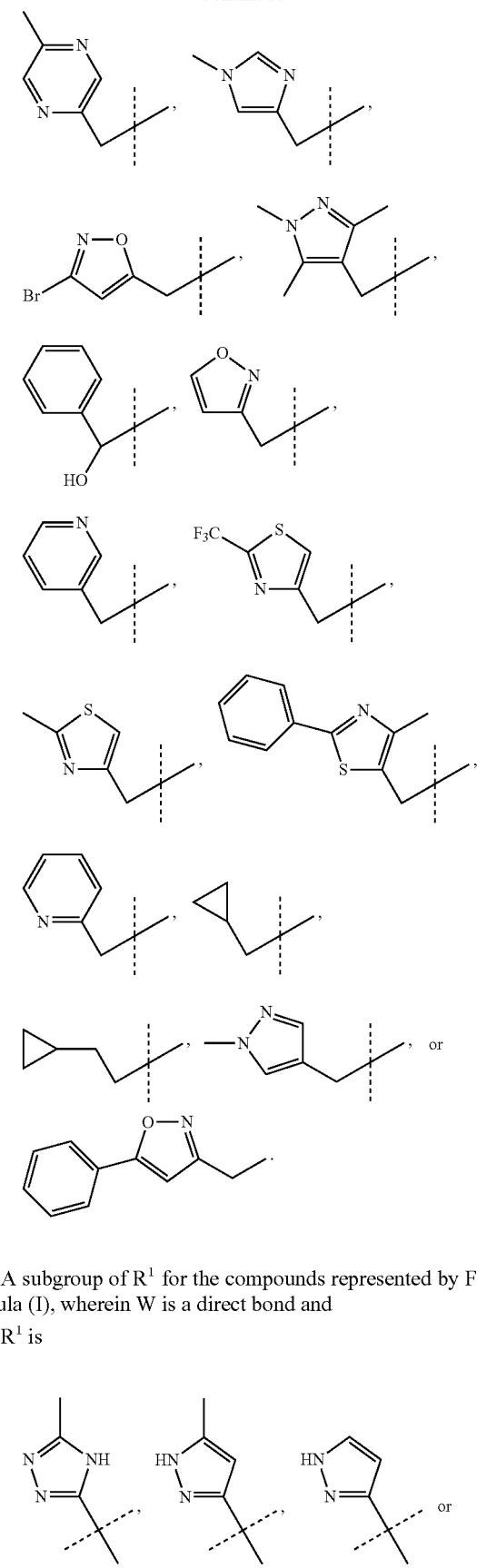
A subgroup of $R^1$ for the compounds represented by Formula (I), wherein W is a direct bond and $R^1$ is -continued
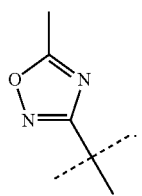
A subgroup of R² for the compounds represented by Formula (I) is hydroxy, $C_1$-$C_4$ alkyl, cycloalkylalkyl, haloalkyl, aralkyl, aralkyloxy or heteroarylalkyl, wherein the cycloalkylalkyl is
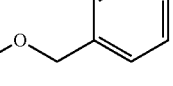
wherein the aralkyloxy is
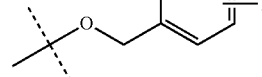
-continued
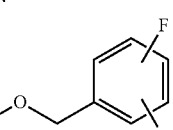
wherein the aralkyl is
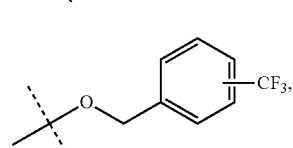

-continued

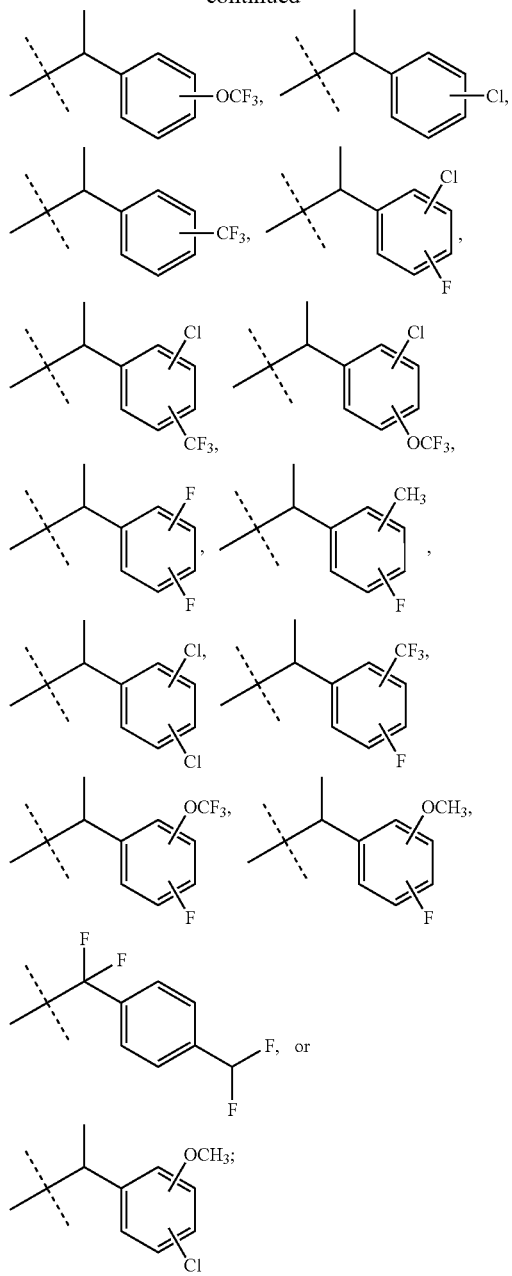

wherein the $C_1$-$C_4$ alkyl is

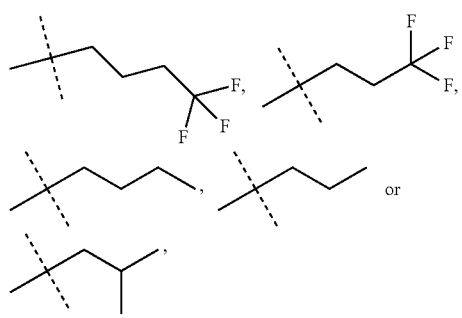

wherein the haloalkyl is

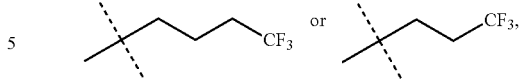

and
wherein the heteroarylalkyl is

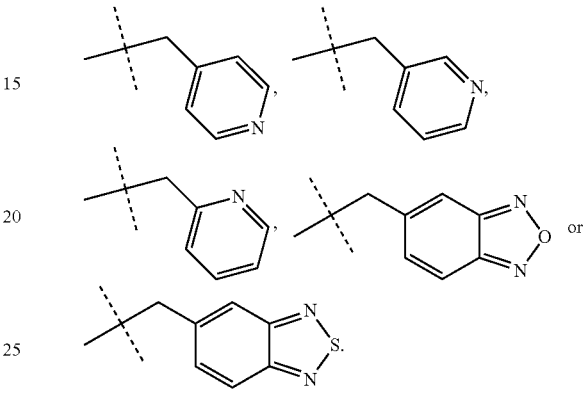

In another embodiment of the invention are the compounds of Formula (I), wherein Q is

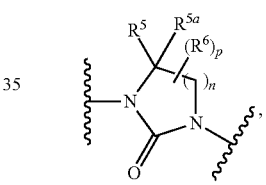

n is 1; p is 0; W is —N(H)C(O)—; $R^1$ is hydrogen, alkyl or aralkyl; $R^2$ is aralkyl; and each of $R^5$ and $R^{5a}$ is hydrogen.

In another subgroup for the compounds represented by Formula (I), a set of compounds are those compounds where W is —N($R^8$)C(O)—; $R^1$ is cycloalkylalkyl, heterocyclylalkyl, aralkyl or heteroarylalkyl; and $R^2$ is alkyl, alkoxy, hydroxyalkyl, alkoxyalkyl, cycloalkylalkyl, haloalkyl, aralkyl or heteroarylalkyl.

Of this set of compounds, a subset of compounds are those compounds where W is —N(H)C(O)—, $R^1$ is heteroarylalkyl; and $R^2$ is aralkyl.

Of this set of compounds, a subset of compounds are those compounds where W is —N(H)C(O)—, $R^1$ is heteroarylalkyl; and $R^2$ is heteroarylalkyl.

Of this set of compounds, another subset of compounds are those compounds where W is —N(H)C(O)—; $R^1$ is heteroarylalkyl; and $R^2$ is alkyl or cycloalkylalkyl.

Of this set of compounds, another subset of compounds are those compounds where W is —N(H)C(O)—; $R^1$ is aralkyl or heterocyclylalkyl; and $R^2$ is aralkyl.

Of this set of compounds, another subset of compounds are those compounds where W is —N(H)C(O)—; $R^1$ is aralkyl or heterocyclylalkyl; and $R^2$ is heteroarylalkyl.

Of this set of compounds, another subset of compounds are those compounds where W is —N(H)C(O)—; $R^1$ is aralkyl or heterocyclylalkyl; and $R^2$ is alkyl or cycloalkylalkyl.

Of this set of compounds, another subset of compounds are those compounds where W is —N(H)C(O)—; $R^1$ is aryl or heterocyclylalkyl; and $R^2$ is heteroarylalkyl.

Of this set of compounds, another subset of compounds are those compounds where W is —N(H)C(O)—; $R^1$ is cycloalkylalkyl; and $R^2$ is aralkyl.

Of this set of compounds, another subset of compounds are those compounds where W is —N(H)C(O)—; $R^1$ is cycloalkylalkyl; and $R^2$ is heteroarylalkyl.

Of this set of compounds, another subset of compounds are those compounds where W is —N(H)C(O)—; $R^1$ is cycloalkylalkyl; and $R^2$ is alkyl or cycloalkylalkyl.

In yet another embodiment of the invention are the compounds of Formula (I, wherein Q is

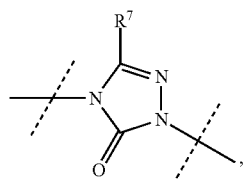

and P, W, $R^1$, $R^2$, $R^3$ and $R^7$ are as defined above.

Of this group of compounds, a subgroup of compounds are those compounds wherein W is —N($R^8$)C(O)—; $R^1$ is hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl or heteroarylalkyl; $R^2$ is hydrogen, alkyl, alkenyl, alkynyl, alkoxy, hydroxy, hydroxyalkyl, alkoxyalkyl, cycloalkyl, cycloalkylalkyl, aryl, haloalkyl, aralkyl, aralkyloxy, heterocyclyl, heterocyclylalkyl, heteroaryl or heteroarylalkyl; $R^3$ is hydrogen or alkyl; and $R^7$ is independently hydrogen, alkyl, haloalkyl or aryl.

Of this set of compounds, another subset of compounds are those compounds where $R^1$ is aralkyl; and $R^2$ is aralkyl.

Of this set of compounds, another subset of compounds are those compounds where $R^1$ is aralkyl; and $R^2$ is heteroarylalkyl or cycloalkylalkyl.

Of this set of compounds, another subset of compounds are those compounds where $R^1$ is hydrogen; and $R^2$ is aralkyl.

Of this set of compounds, another subset of compounds are those compounds where $R^1$ is hydrogen; and $R^2$ is alkyl or haloalkyl.

In another embodiment of the invention are the compounds of Formula (I), wherein Q is

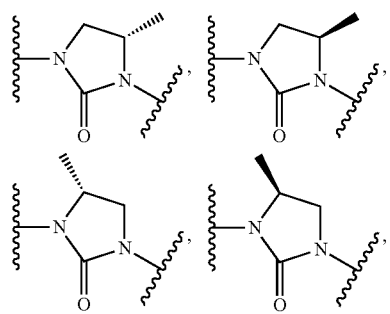

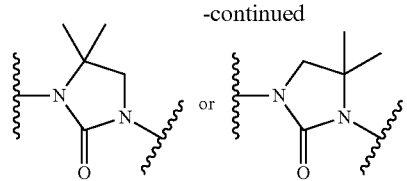

In another embodiment of the invention are the compounds of Formula (II) wherein, $$R^1\text{—}W\text{—}P\text{-}Q'\text{-}R^2 \qquad (II)$$

wherein P is

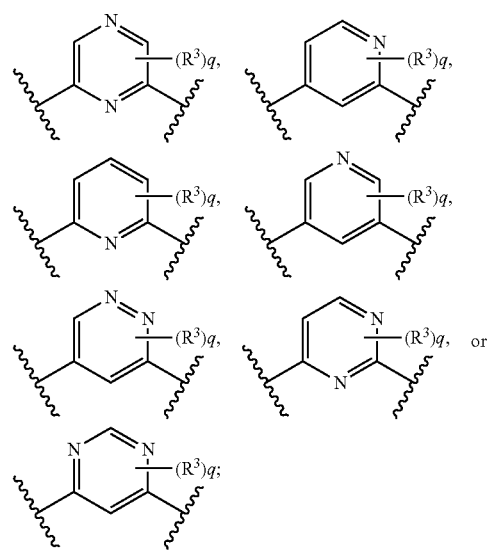

Q' is —N($R^8$)C(O)—,

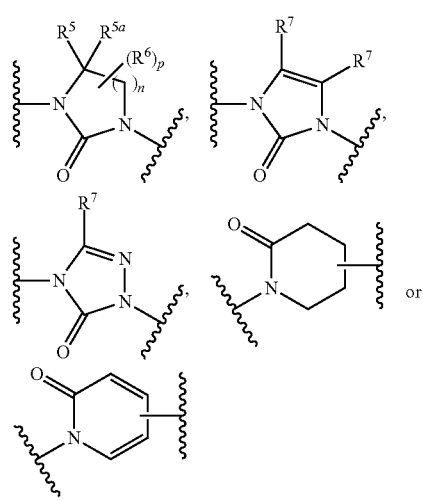

W is —N($R^8$)C(O)—, —C(O)N($R^8$)— or a direct bond;
V is a direct bond;
n is 1, 2, or 3;
p is 0, 1, 2, to 2n;
q is 0, 1, 2, or 3;

R¹ is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl, or heteroarylalkyl;

R² is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl or heteroarylalkyl;

R³ is alkyl, alkenyl, alkynyl, alkoxy, hydroxyalkyl, alkoxyalkyl, cycloalkyl, cycloalkylalkyl, heterocyclyl, aryl, aralkyl, heteroaryl, halo, haloalkyl, trifluoromethoxyl, cyano, hydroxyl, or —N(R⁸)₂;

R⁵ and R⁵ᵃ are independently selected from hydrogen, alkyl, haloalkyl, hydroxyl, hydroxyalkyl, alkoxy, cycloalkylalkyl or aralkyl;

or R⁵ and R⁵ᵃ are together to form an oxo (=O) group, or to form a cycloaklyl;

R⁶ is alkyl, aryl, cycloalkyl, heteroaryl, heterocyclyl, hydroxyalkyl, haloalkyl, alkoxy, cycloalkylalkyl, or aralkyl;

or R⁵ and R⁶ on adjacent carbon are together to form a cycloaklyl, or to form an aryl;

R⁷ is hydrogen, alkyl, trifluoromethyl, aryl, cycloalkyl, heteroaryl, heterocyclyl, hydroxyalkyl, haloalkyl, cycloalkylalkyl or aralkyl; and R⁸ is hydrogen, alkyl, hydroxyalkyl, cycloalkylalkyl, aryl, heteroaryl, heterocyclyl or aralkyl;

a stereoisomer, enantiomer or tautomer thereof, a pharmaceutically acceptable salt thereof, a pharmaceutical composition thereof or a prodrug thereof.

In another embodiment of the invention are the compounds of Formula (II) wherein,

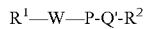

(II)

wherein P is

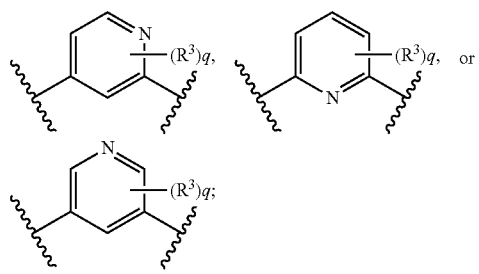

Q' is —N(R⁸)C(O)—,

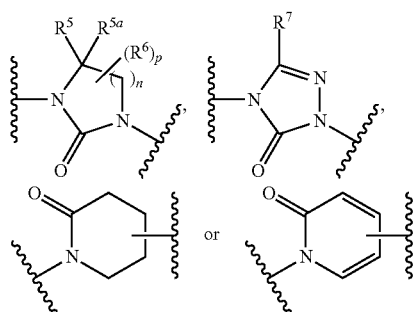

W is —N(R⁸)C(O)—, —C(O)N(R⁸)— or a direct bond;
n is 1, 2, or 3;

p is 0, 1, 2, to 2n;
q is 0, 1, 2, or 3;

R¹ is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl, or heteroarylalkyl;

R² is hydrogen, alkyl, alkenyl, alkynyl, alkoxy, hydroxy, hydroxyalkyl, alkoxyalkyl, cycloalkyl, cycloalkylalkyl, aryl, haloalkyl, aralkyl, aralkyloxy, heterocyclyl, heterocyclylalkyl, heteroaryl or heteroarylalkyl;

R³ is alkyl, alkenyl, alkynyl, alkoxy, hydroxyalkyl, alkoxyalkyl, cycloalkyl, cycloalkylalkyl, heterocyclyl, aryl, aralkyl, heteroaryl, halo, haloalkyl, trifluoromethoxyl, cyano, hydroxy, or —N(R⁸)₂;

R⁵ and R⁵ᵃ are independently selected from hydrogen, alkyl, haloalkyl, hydroxy, hydroxyalkyl, alkoxy, cycloalkylalkyl or aralkyl;

or R⁵ and R⁵ᵃ are together to form an oxo (=O) group, or to form a cycloaklyl;

R⁶ is alkyl, aryl, cycloalkyl, heteroaryl, heterocyclyl, hydroxyalkyl, haloalkyl, alkoxy, cycloalkylalkyl, or aralkyl;

or R⁵ and R⁶ on adjacent carbons are together to form a cycloaklyl, or to form an aryl;

R⁷ is hydrogen, alkyl, haloalkyl, aryl, cycloalkyl, heteroaryl, heterocyclyl, hydroxyalkyl, cycloalkylalkyl or aralkyl; and R⁸ is hydrogen, alkyl, hydroxyalkyl, cycloalkylalkyl, aryl, heteroaryl, heterocyclyl or aralkyl;

a stereoisomer, enantiomer or tautomer thereof, a pharmaceutically acceptable salt thereof, a pharmaceutical composition thereof or a prodrug thereof.

In another embodiment of Formula (II)

R¹ is hydrogen, C₁-C₇alkyl, C₂-C₆alkenyl, C₂-C₆alkynyl, C₁-C₇alkoxy, hydroxyC₁-C₄alkyl, alkoxyC₁-C₄alkyl, C₃-C₇cycloalkyl, C₃-C₇cycloalkylC₁-C₄alkyl, C₆-C₁₀aryl, haloC₁-C₄alkyl, aralkyl, C₂-C₁₀heterocyclyl, C₂-C₁₀heterocyclylC₁-C₄alkyl, C₁-C₁₀heteroaryl, or C₁-C₁₀heteroarylC₁-C₄alkyl;

R² is hydrogen, C₁-C₇alkyl, C₂-C₆alkenyl, C₂-C₆alkynyl, C₁-C₇alkoxy, hydroxy, hydroxyC₁-C₄alkyl, alkoxyC₁-C₄alkyl, C₃-C₇cycloalkyl, C₃-C₇cycloalkylC₁-C₄alkyl, C₆-C₁₀aryl, haloC₁-C₄alkyl, aralkyl, aralkyloxy, C₂-C₁₀heterocyclyl, C₂-C₁₀heterocyclylC₁-C₄alkyl, C₁-C₁₀heteroaryl, or C₁-C₁₀heteroarylC₁-C₄alkyl;

R³ is C₁-C₇alkyl, C₂-C₆alkenyl, C₂-C₆alkynyl, C₁-C₇alkoxy, hydroxyC₁-C₄alkyl, alkoxyC₁-C₄alkyl, C₃-C₇cycloalkyl, C₃-C₇cycloalkylC₁-C₄alkyl, C₂-C₁₀heterocyclyl, C₆-C₁₀aryl, aralkyl, C₁-C₁₀heteroaryl, halo, haloC₁-C₄alkyl, trifluoromethoxyl, cyano, hydroxy, or —N(R⁸)₂;

R⁵ and R⁵ᵃ are independently selected from hydrogen, C₁-C₇alkyl, haloC₁-C₄alkyl, hydroxy, hydroxyC₁-C₄alkyl, C₁-C₇alkoxy, C₃-C₇cycloalkylC₁-C₄alkyl or aralkyl;

or R⁵ and R⁵ᵃ are together to form an oxo (=O) group, or to form a C₃-C₇cycloalkyl;

R⁶ is C₁-C₇alkyl, C₆-C₁₀aryl, C₃-C₇cycloalkyl, C₁-C₁₀heteroaryl, C₂-C₁₀heterocyclyl, hydroxyC₁-C₄alkyl, haloC₁-C₄alkyl, C₁-C₇alkoxy, C₃-C₇cycloalkylC₁-C₄alkyl, or aralkyl;

or R⁵ and R⁶ on adjacent carbons are together to form a C₃-C₇cycloalkyl, or to form an C₆-C₁₀aryl;

R⁷ is hydrogen, C₁-C₇alkyl, haloC₁-C₄alkyl, C₆-C₁₀aryl, C₃-C₇cycloalkyl, C₁-C₁₀heteroaryl, C₂-C₁₀heterocyclyl, hydroxyC₁-C₄alkyl, C₃-C₇cycloalkylC₁-C₄alkyl or aralkyl; and R$^8$ is hydrogen, C$_1$-C$_7$alkyl, hydroxyC$_1$-C$_4$alkyl, C$_3$-C$_7$cycloalkylC$_1$-C$_4$alkyl, C$_6$-C$_{10}$aryl, C$_1$-C$_{10}$heteroaryl, C$_2$-C$_{10}$heterocyclyl or aralkyl;

a stereoisomer, enantiomer or tautomer thereof, a pharmaceutically acceptable salt thereof, a pharmaceutical composition thereof or a prodrug thereof.

In another embodiment of the invention are the compounds as follows:

N-benzyl-2-(3-methoxybenzamido)isonicotinamide;
N-benzyl-2-(3,5-difluorobenzamido)isonicotinamide;
N-benzyl-2-(4-(dimethylamino)benzamido)isonicotinamide;
N-(4-(4-benzyl-1H-imidazol-2-yl)pyridin-2-yl)benzamide;
2-(3-(4-fluorobenzyl)-2-oxoimidazolidin-1-yl)-N-(oxazol-4-ylmethyl)isonicotinamide;
2-(3-(4-fluorobenzyl)-2-oxoimidazolidin-1-yl)-N-((5-methylpyrazin-2-yl)methyl)isonicotinamide;
2-(3-(4-fluorobenzyl)-2-oxoimidazolidin-1-yl)-N-((1-methyl-1H-imidazol-4-yl)methyl)isonicotinamide;
2-(3-(4-fluorobenzyl)-2-oxoimidazolidin-1-yl)-N-((5-methylisoxazol-3-yl)methyl)isonicotinamide;
of 2-(3-(4-fluorobenzyl)-2-oxoimidazolidin-1-yl)-N-(pyridin-2-ylmethyl)isonicotinamide dihydrochloride;
N-(4-fluorobenzyl)-2-(3-(4-fluorobenzyl)-2-oxoimidazolidin-1-yl)isonicotinamide;
2-(3-(cyclopropylmethyl)-2-oxoimidazolidin-1-yl)-N-(pyridin-4-ylmethyl)isonicotinamide;
N-(3,4-difluorobenzyl)-2-(2-oxo-3-(pyridin-3-ylmethyl)imidazolidin-1-yl)isonicotinamide;
2-(3-(3,4-Difluorobenzyl)-2-oxoimidazolidin-1-yl)-N-(pyridin-2-ylmethyl)-isonicotinamide;
2-(2-oxo-3-(4-(trifluoromethyl)benzyl)imidazolidin-1-yl)-N-(pyridin-2-ylmethyl)-isonicotinamide;
N-((5-Methylisoxazol-3-yl)methyl)-2-(2-oxo-3-(4-(trifluoromethoxy)-benzyl)imidazolidin-1-yl)isonicotinamide;
2-(2-oxo-3-(4-(trifluoromethoxy)benzyl)imidazolidin-1-yl)-N-(pyridin-2-ylmethyl)-isonicotinamide;
N-((5-Methylisoxazol-3-yl)methyl)-2-(2-oxo-3-(4-(trifluoromethyl)-benzyl)imidazolidin-1-yl)isonicotinamide;
2-(1-(4-Fluorobenzyl)-5-oxo-1H-1,2,4-triazol-4(5H)-yl)-N-((5-methylisoxazol-3-yl)methyl)-isonicotinamide;
2-(3-(3,4-Difluorobenzyl)-2-oxoimidazolidin-1-yl)-N-((5-methylisoxazol-3-yl)methyl)-isonicotinamide;
2-(1-(4-Fluorobenzyl)-5-oxo-1H-1,2,4-triazol-4(5H)-yl)-N-(pyridin-2-ylmethyl)-isonicotinamide;
2-(1-(3,4-Difluorobenzyl)-5-oxo-1H-1,2,4-triazol-4(5H)-yl)-N-((5-methylisoxazol-3-yl)methyl)-isonicotinamide;
2-(1-(3,4-Difluorobenzyl)-5-oxo-1H-1,2,4-triazol-4(5H)-yl)-N-(pyridin-2-ylmethyl)-isonicotinamide;
2-(3-(3,4-Difluorobenzyl)-2-oxoimidazolidin-1-yl)isonicotinamide;
2-(2-Oxo-3-(4-(Trifluoromethyl)-benzyl)imidazolidin-1-yl)isonicotinamide; or
2-(2-Oxo-3-(4-(trifluoromethoxy)-benzyl)imidazolidin-1-yl)isonicotinamide.

In another embodiment P, Q, W, R$^1$, R$^2$, R$^3$, R$^5$, R$^{5a}$, R$^6$, R$^7$ and R$^8$ groups are those defined by the P, Q, W, R$^1$, R$^2$, R$^3$, R$^5$, R$^{5a}$, R$^6$, R$^7$ and R$^8$ groups, respectively, in Examples 1 to 26.34 in the Examples section below.

In another embodiment individual compounds according to the invention are those listed in Examples 1 to 26.34 in the Examples section below.

In one embodiment, the methods of the invention are directed towards the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, cardiovascular disease, diabetes, obesity, metabolic syndrome, dermatological disorders and the like by administering an effective amount of a compound of the invention.

The present invention also relates to pharmaceutical composition containing the compounds of the invention. In one embodiment, the invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

Utility and Testing of the Compounds of the Invention

The present invention relates to compounds, pharmaceutical compositions and methods of using the compounds and pharmaceutical compositions for the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, especially cardiovascular disease, diabetes, obesity, metabolic syndrome, dermatological disorders and the like, by administering to a patient in need of such treatment an effective amount of an SCD modulating, especially inhibiting, agent.

In general, the present invention provides a method for treating a patient for, or protecting a patient from developing, a disease related to dyslipidemia and/or a disorder of lipid metabolism, wherein lipid levels in an animal, especially a human being, are outside the normal range (i.e., abnormal lipid level, such as elevated plasma lipid levels), especially levels higher than normal, preferably where said lipid is a fatty acid, such as a free or complexed fatty acid, triglycerides, phospholipids, or cholesterol, such as where LDL-cholesterol levels are elevated or HDL-cholesterol levels are reduced, or any combination of these, where said lipid-related condition or disease is an SCD-mediated disease or condition, comprising administering to an animal, such as a mammal, especially a human patient, a therapeutically effective amount of a compound of the invention or a pharmaceutical composition comprising a compound of the invention wherein the compound modulates the activity of SCD, preferably human SCD1.

The compounds of the invention modulate, preferably inhibit, the activity of human SCD enzymes, especially human SCD1.

The general value of the compounds of the invention in modulating, especially inhibiting, the activity of SCD can be determined using the assay described below in Example 27.

Alternatively, the general value of the compounds in treating disorders and diseases may be established in industry standard animal models for demonstrating the efficacy of compounds in treating obesity, diabetes or elevated triglyceride or cholesterol levels or for improving glucose tolerance. Such models include Zucker obese fa/fa rats (available from Harlan Sprague Dawley, Inc. (Indianapolis, Ind.)), or the Zucker diabetic fatty rat (ZDF/GmiCrl-fa/fa) (available from Charles River Laboratories (Montreal, Quebec)), and Sprague Dawley rats (Charles Rivers), as used in models for diet-induced obesity (Ghibaudi, L. et al., (2002), *Obes. Res.* Vol. 10, pp. 956-963). Similar models have also been developed for mice and Lewis rat.

The compounds of the instant invention are inhibitors of delta-9 desaturases and are useful for treating diseases and disorders in humans and other organisms, including all those human diseases and disorders which are the result of aberrant delta-9 desaturase biological activity or which may be ameliorated by modulation of delta-9 desaturase biological activity.

As defined herein, an SCD-mediated disease or condition is defined as any disease or condition in which the activity of SCD is elevated and/or where inhibition of SCD activity can be demonstrated to bring about symptomatic improvements for the individual so treated. As defined herein, an SCD-mediated disease or condition includes, but is not limited to, a disease or condition which is, or is related to, cardiovascular disease, dyslipidemias (including but not limited to disorders of serum levels of triglycerides, hypertriglyceridemia, VLDL, HDL, LDL, fatty acid Desaturation Index (e.g. the ratio of 18:1/18:0 fatty acids, or other fatty acids, as defined elsewhere herein), cholesterol, and total cholesterol, hypercholesterolemia, as well as cholesterol disorders (including disorders characterized by defective reverse cholesterol transport)), familial combined hyperlipidemia, coronary artery disease, arteriosclerosis, atherosclerosis, heart disease, cerebrovascular disease (including but not limited to stroke, ischemic stroke and transient ischemic attack (TIA)), peripheral vascular disease, and ischemic retinopathy.

An SCD-mediated disease or condition also includes metabolic syndrome (including but not limited to dyslipidemia, obesity and insulin resistance, hypertension, microalbuminemia, hyperuricaemia, and hypercoagulability), Syndrome X, diabetes, insulin resistance, decreased glucose tolerance, non-insulin-dependent diabetes mellitus, Type II diabetes, Type I diabetes, diabetic complications, body weight disorders (including but not limited to obesity, overweight, cachexia, bulimia and anorexia), weight loss, wasting disorders, body mass index and leptin-related diseases. In a preferred embodiment, compounds of the invention will be used to treat diabetes mellitus and/or obesity.

An SCD-mediated disease also includes obesity related syndromes, disorders and diseases that include, but not limited to, obesity as a result of (i) genetics, (ii) diet, (iii) food intake volume, (iv) a metabolic disorder, (v) a hypothalamic disorder, (vi) age, (vii) abnormal adipose distribution, (viii) abnormal adipose compartment distribution, (ix) compulsive eating disorders, and (x) motivational disorders which include the desire to consume sugars, carbohydrates, alcohols or drugs. Symptoms associates with obesity related syndromes, disorders and diseases include, but not limited to, reduced activity. Obesity also increases the likelihood of sleep apnea, gallstones, osteoporosis and certain cancers.

As used herein, the term "metabolic syndrome" is a recognized clinical term used to describe a condition comprising combinations of Type II diabetes, impaired glucose tolerance, insulin resistance, hypertension, obesity, increased abdominal girth, hypertriglyceridemia, low HDL, hyperuricaernia, hypercoagulability and/or microalbuminemia. The American Heart Association has published guidelines for the diagnosis of metabolic syndrome, Grundy, S., et. al., (2006) *Cardiol. Rev.* Vol. 13, No. 6, pp. 322-327.

An SCD-mediated disease or condition also includes fatty liver, hepatic steatosis, vascular restenosis, hepatitis, non-alcoholic hepatitis, non-alcoholic steatohepatitis (NASH), alcoholic hepatitis, acute fatty liver, fatty liver of pregnancy, drug-induced hepatitis, erythrohepatic protoporphyria, iron overload disorders, hereditary hemochromatosis, hepatic fibrosis, hepatic cirrhosis, hepatoma, hepatomegaly and conditions related thereto.

An SCD-mediated disease or condition also includes biliary cholesterol crystallization and related conditions, such as but not limited to, gallstones, primary sclerosing cholangitis (PSC), progressive familial intrahepatic cholestasis (PFIC), high serum gamma-glutamyl transferase (GGT) PFIC, low-GGT PFIC (i.e. Byler disease, Byler syndrome), Caroli's disease, biliary helminthiasis, biliary strictures, choledocholithiasis, obstructive cholestasis, chronic cholestatic disease, presence of biliary sludge, and cholesterolosis of gallbladder.

An SCD-mediated disease or condition also includes but is not limited to a disease or condition which is, or is related to primary hypertriglyceridemia, or hypertriglyceridemia secondary to another disorder or disease, such as hyperlipoproteinemias, familial histiocytic reticulosis, lipoprotein lipase deficiency, apolipoprotein deficiency (such as ApoCII deficiency or ApoE deficiency), and the like, or hypertriglyceridemia of unknown or unspecified etiology.

An SCD-mediated disease or condition also includes a disorder of polyunsaturated fatty acid (PUFA) disorder, or a dermatological or skin disorder, including but not limited to eczema, acne, rosacea, skin ageing, seborrheic skin, psoriasis, keloid scar formation or prevention, diseases related to production or secretions from mucous membranes, such as monounsaturated fatty acids, wax esters, and the like. Preferably, the compounds of the invention will prevent or attenuate keloid scar formation by reduction of excessive sebum production that typically results in their formation. The investigation of the role of SCD inhibitors in the treatment of acne was advanced by the discovery that rodents lacking a functional SCD1 gene had changes to the condition of their eyes, skin, coat (Zheng Y., et al. "SCD1 is expressed in sebaceous glands and is disrupted in the asebia mouse", *Nat. Genet.* (1999) 23:268-270. Miyazaki, M., "Targeted Disruption of Stearoyl-CoA Desaturase1 Gene in Mice Causes Atrophy of Sebaceous and Meibomian Glands and Depletion of Wax Esters in the Eyelid", *J. Nutr.* (2001), Vol. 131, pp 2260-68., Binczek, E. et al., "Obesity resistance of the stearoyl-CoA desaturase-deficient mouse results from disruption of the epidermal lipid barrier and adaptive thermoregulation", *Biol. Chem.* (2007) Vol. 388 No. 4, pp 405-18).

An SCD-mediated disease or condition also includes inflammation, sinusitis, asthma, bronchitis, pancreatitis, osteoarthritis, rheumatoid arthritis, cystic fibrosis, and premenstrual syndrome.

An SCD-mediated disease or condition also includes but is not limited to a disease or condition which is, or is related to cancer, polycystic ovary syndrome, neoplasia, malignancy, metastases, tumours (benign or malignant), carcinogenesis, hepatomas and the like.

An SCD-mediated disease or condition also includes a condition where increasing lean body mass or lean muscle mass is desired, such as is desirable in enhancing performance through muscle building. Myopathies and lipid myopathies such as carnitine palmitoyltransferase deficiency (CPT I or CPT II) are also included herein. Such treatments are useful in humans and in animal husbandry, including for administration to bovine, porcine or avian domestic animals or any other animal to reduce triglyceride production and/or provide leaner meat products and/or healthier animals.

An SCD-mediated disease or condition also includes a disease or condition that is, or is related to, neurological diseases, psychiatric disorders, multiple sclerosis, eye diseases, polycystic ovary syndrome, sleep-disordered (e.g. disturbances of breathing or circadian rhythm, dysomnia, insomnia, sleep apnea, and narcolepsy), abnormal alanine transferase levels, respiratory disorders and immune disorders.

An SCD-mediated disease or condition also includes neurological diseases, including mild cognitive impairment (MCI), cerebral amyloid angipathy (CAA), down syndrome (DS), depression, schizophrenia, obsessive-compulsive disorder, and biopolar disorder.

An SCD-mediated disease or condition also includes neurodegenerative diseases, including Alzheimer's disease, Parkinson's disease, dementia with Lewy bodies, amyotrophic lateral sclerosis or Lou Gehrig's disease, Alpers' disease, Leigh's disease, Pelizaeus-Merzbacher disease, Olivopontocerebellar atrophy, Friedreich's ataxia, leukodystrophies, Rett syndrome, Ramsay Hunt syndrome type II, and Down's syndrome.

An SCD-mediated disease or condition also includes a disease or condition which is, or is related to, viral diseases or infections including but not limited to all positive strand RNA viruses, coronaviruses, SARS virus, SARS-associated coronavirus, Togaviruses, Picornaviruses, Coxsackievirus, Yellow Fever virus, Flaviviridae, ALPHAVIRUS (TOGAVIRIDAE) including Rubella virus, Eastern equine encephalitis virus, Western equine encephalitis virus, Venezuelan equine encephalitis virus, Sindbis virus, Semliki forest virus, Chikungunya virus, O'nyong'nyong virus, Ross river virus, Mayaro virus, Alphaviruses; ASTROVIRIDAE including Astrovirus, Human Astroviruses; CALICIVIRIDAE including Vesicular exanthema of swine virus, Norwalk virus, Calicivirus, Bovine calicivirus, Pig calcivirus, Hepatitis E; CORONAVIRIDAE including Coronavirus, SARS virus, Avian infectious bronchitis virus, Bovine coronavirus, Canine coronavirus, Feline infectious peritonitis virus, Human coronavirus 299E, Human coronavirus OC43, Murine hepatitis virus, Porcine epidemic diarrhea virus, Porcine hemagglutinating encephalomyelitis virus, Porcine transmissible gastroenteritis virus, Rat coronavirus, Turkey coronavirus, Rabbit coronavirus, Berne virus, Breda virus; FLAVIVIRIDAE including Hepatitis C virus, West Nile virus, Yellow Fever virus, St. Louis encephalitis virus, Dengue Group, Hepatitis G virus, Japanese B encephalitis virus, Murray Valley encephalitis virus, Central European tick-borne encephalitis virus, Far Eastern tick-borne encephalitis virus, Kyasanur forest virus, Louping ill virus, Powassan virus, Omsk hemorrhagic fever virus, Kumilinge virus, Absetarov anzalova hypr virus, ITheus virus, Rocio encephalitis virus, Langat virus, Pestivirus, Bovine viral diarrhea, Hog cholera virus, Rio Bravo Group, Tyuleniy Group, Ntaya Group, Uganda S Group, Modoc Group; PICORNAVIRIDAE including Coxsackie A virus, Rhinovirus, Hepatitis A virus, Encephalomyocarditis virus, Mengovirus, ME virus, Human poliovirus 1, Coxsackie B; POCYVIRIDAE including Potyvirus, Rymovirus, Bymovirus. Additionally it can be a disease or infection caused by or linked to Hepatitis viruses, Hepatitis B virus, Hepatitis C virus, human immunodeficiency virus (HIV) and the like. Treatable viral infections include those where the virus employs an RNA intermediate as part of the replicative cycle (hepatitis or HIV); additionally it can be a disease or infection caused by or linked to RNA negative strand viruses such as influenza and parainfluenza viruses.

The compounds identified in the instant specification inhibit the desaturation of various fatty acids (such as the $C_9$-$C_{10}$ desaturation of stearoyl-CoA), which is accomplished by delta-9 desaturases, such as stearoyl-CoA desaturase 1 (SCD1). As such, these compounds inhibit the formation of various fatty acids and downstream metabolites thereof. This may lead to an accumulation of stearoyl-CoA or palmitoyl-CoA and other upstream precursors of various fatty acids; which may possibly result in a negative feedback loop causing an overall change in fatty acid metabolism. Any of these consequences may ultimately be responsible for the overall therapeutic benefit provided by these compounds.

Typically, a successful SCD inhibitory therapeutic agent will meet some or all of the following criteria. Oral availability should be at or above 20%. Animal model efficacy is less than about 20 mg/Kg, 2 mg/Kg, 1 mg/Kg, or 0.5 mg/Kg and the target human dose is between 10 and 250 mg/70 Kg, although doses outside of this range may be acceptable. ("mg/Kg" means milligrams of compound per kilogram of body mass of the subject to whom it is being administered). The required dosage should preferably be no more than about once or twice a day or at meal times. The therapeutic index (or ratio of toxic dose to therapeutic dose) should be greater than 10. The $IC_{50}$ ("Inhibitory Concentration—50%") is a measure of the amount of compound required to achieve 50% inhibition of SCD activity, over a specific time period, in an SCD biological activity assay. Any process for measuring the activity of SCD enzymes, preferably mouse or human SCD enzymes, may be utilized to assay the activity of the compounds useful in the methods of the invention in inhibiting said SCD activity. Compounds of the invention demonstrate an $IC_{50}$ ("Inhibitory Concentration of 50%") in a 15 minute microsomal assay of preferably less than 10 mM, less than 5 µM, less than 2.5 µM, less than 1 µM, less than 750 nM, less than 500 nM, less than 250 nM, less than 100 nM, less than 50 nM, and most preferably less than 20 nM. Compounds of the invention may show reversible inhibition (i.e., competitive inhibition) and preferably do not inhibit other iron binding proteins.

The identification of compounds of the invention as SCD inhibitors was readily accomplished using the SCD enzyme and microsomal assay procedure described in Shanklin J. and Summerville C., Proc. Natl. Acad. Sci. USA (1991), Vol. 88, pp. 2510-2514. When tested in this assay, compounds of the invention had less than 50% remaining SCD activity at 10 µM concentration of the test compound, preferably less than 40% remaining SCD activity at 10 µM concentration of the test compound, more preferably less than 30% remaining SCD activity at 10 µM concentration of the test compound, and even more preferably less than 20% remaining SCD activity at 10 µM concentration of the test compound, thereby demonstrating that the compounds of the invention are potent inhibitors of SCD activity.

These results provide the basis for analysis of the structure-activity relationship (SAR) between test compounds and SCD. Certain-groups tend to provide more potent inhibitory compounds. SAR analysis is one of the tools those skilled in the art may employ to identify preferred embodiments of the compounds of the invention for use as therapeutic agents. Other methods of testing the compounds disclosed herein are also readily available to those skilled in the art. Thus, in addition, the determination of the ability of a compound to inhibit SCD may be accomplished in vivo. In one such embodiment this is accomplished by administering said chemical agent to an animal afflicted with a triglyceride (TG)- or very low density lipoprotein (VLDL)-related disorder and subsequently detecting a change in plasma triglyceride level in said animal thereby identifying a therapeutic agent useful in treating a triglyceride (-TG)- or very low density lipoprotein (VLDL)-related disorder. In such embodiment, the animal may be a human, such as a human patient afflicted with such a disorder and in need of treatment of said disorder.

In specific embodiments of such in vivo processes, said change in SCD1 activity in said animal is a decrease in activity, preferably wherein said SCD1 modulating agent does not substantially inhibit the biological activity of a delta-5 desaturase, delta-6 desaturase or fatty acid synthetase or other enzymes containing iron at the active site.

The model systems useful for compound evaluation may include, but are not limited to, the use of liver microsomes, such as from mice that have been maintained on a high carbohydrate diet, or from human donors, including persons suffering from obesity. Immortalized cell lines, such as HepG2 (from human liver), MCF-7 (from human breast cancer) and 3T3-L1 (from mouse adipocytes) may also be used. Primary cell lines, such as mouse primary hepatocytes, are also useful in testing the compounds of the invention. Where whole animals are used, mice used as a source of primary hepatocyte cells may also be used wherein the mice have been maintained on a high carbohydrate diet to increase SCD activity in mirocrosomes and/or to elevate plasma triglyceride levels (i.e., the 18:1/18:0 ratio); alternatively mice on a normal diet or mice with normal triglyceride levels may be used. Mouse models employing transgenic mice designed for hypertriglyceridemia are also available. Rabbits and hamsters are also useful as animal models, especially those expressing CETP (cholesterol ester transfer protein).

Another suitable method for determining the in vivo efficacy of the compounds of the invention is to indirectly measure their impact on inhibition of SCD enzyme by measuring a subject's Desaturation Index after administration of the compound.

"Desaturation Index" as employed in this specification means the ratio of the product over the substrate for the SCD enzyme as measured from a given tissue sample. This may be calculated using three different equations 18:1n–9/18:0 (oleic acid over stearic acid); 16:1n–7/16:0 (palmitoleic acid over palmitic acid); and/or 16:1n–7+18:1n–7/16:0 (measuring all reaction products of 16:0 desaturation over 16:0 substrate).

Desaturation Index is primarily measured in liver or plasma triglycerides, but may also be measured in other selected lipid fractions from a variety of tissues. Desaturation Index, generally speaking, is a tool for plasma lipid profiling.

A number of human diseases and disorders are the result of aberrant SCD1 biological activity and may be ameliorated by modulation of SCD1 biological activity using the therapeutic agents of the invention.

Inhibition of SCD expression may also affect the fatty acid composition of membrane phospholipids, as well as production or levels of triglycerides and cholesterol esters. The fatty acid composition of phospholipids ultimately determines membrane fluidity, with a subsequent modulation of the activity of multiple enzymes present within the membrane, while the effects on the composition of triglycerides and cholesterol esters can affect lipoprotein metabolism and adiposity.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented.

For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

Alternatively, another format can be used to measure the effect of SCD inhibition on sebaceous gland function. In a typical study using ridnets, oral, intravenous or topical formulations of the SCD inhibitor are administered to a rodent for a period of 1 to 8 days. Skin samples are taken and prepared for histological assessment to determine sebaceous gland number, size, or lipid content. A reduction of sebaceous gland size, number or function would indicate that the SCD inhibitor would have a beneficial impact on acne vulgaris, (Clark, S. B. et al. "Pharmacological modulation of sebaceous gland activity: mechanisms and clinical applications", *Dermatol. Clin.* (2007) Vol. 25, No. 2, pp 137-46. Geiger, J. M., "Retinoids and sebaceous gland activity" *Dermatology* (1995), Vol. 191, No. 4, pp 305-10).

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

Those skilled in the art are familiar with how to determine suitable doses of the compounds for use in treating the diseases and disorders contemplated herein.

Therapeutic doses are generally identified through a dose ranging study in humans based on preliminary evidence derived from animal studies. Doses must be sufficient to result in a desired therapeutic benefit without causing unwanted side effects for the patient. The preferred dosage range for an animal is 0.001 mg/Kg to 10,000 mg/Kg, including 0.5 mg/Kg, 1.0 mg/Kg, 2.0 mg/Kg, 5.0 mg/Kg, 10 mg/Kg and 20 mg/Kg, though doses outside this range may be acceptable. The dosing schedule may be once or twice per day, although more often or less often may be satisfactory.

Those skilled in the art are also familiar with determining administration methods (oral, intravenous, inhalation, subcutaneous, transdermal, topical, etc.), dosage forms, suitable pharmaceutical excipients and other matters relevant to the delivery of the compounds to a subject in need thereof.

In an alternative use of the invention, the compounds of the invention can be used in in vitro or in vivo studies as exemplary agents for comparative purposes to find other compounds also useful in treatment of, or protection from, the various diseases disclosed herein.

The pharmaceutical compositions according to the invention are those suitable for enteral, such as oral or rectal, transdermal, intravenous, intradermal, subcutaneous, intramuscular, colonical, ophthalmic, intraurethral, nasal (e.g. inhalation), intraperitoneal and parenteral administration to mammals, including man, to inhibit stearoyl-CoA desaturase, and for the treatment of conditions associated with stearoyl desaturase activity. In general, the pharmaceutical compositions comprise a therapeutically effective amount of a pharmacologically active compound of the instant invention, alone or in combination with one or more pharmaceutically acceptable carriers.

The pharmacologically active compounds of the invention are useful in the manufacture of pharmaceutical compositions comprising a therapeutically effective amount thereof in conjunction or admixture with excipients or carriers suitable for either enteral or parenteral application. For enteral or parenteral application, it is preferred to administer an effective amount of a pharmaceutical composition according to the invention as tablets or gelatin capsules. Such pharmaceutical compositions may comprise, for example, the active ingredient together with diluents (e.g., lactose, dextrose, sucrose, mannitol, sorbitol, cellulose and/or glycine), lubricants (e.g., silica, talcum, stearic acid, its magnesium or calcium salt and/or polyethyleneglycol), and for tablets also comprises binders (e.g., magnesium aluminum silicate, starch paste, gelatin, tragacanth, methylcellulose, sodium carboxymethylcellulose and/or polyvinylpyrrolidone) and disintegrants (e.g., starches, agar, alginic acid or its sodium salt) or effervescent mixtures and absorbants, colorants, flavors and sweeteners.

In another aspect of the present invention the compounds may be in the form of injectable compositions, e.g. preferably aqueous isotonic solutions or suspensions, and suppositories, which can be advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions may be prepared according to conventional mixing, granulating or coating methods, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate-controlling barrier to deliver the compound of the skin of the host at a controlled and pre-determined rate over a prolonged period of time, and means to secure the device to the skin.

The most suitable route will depend on the nature and severity of the condition being treated. Those skilled in the art are also familiar with determining administration methods, dosage forms, suitable pharmaceutical excipients and other matters relevant to the delivery of the compounds to a subject in need thereof.

The compounds of the invention may be usefully combined with one or more other therapeutic agents for the treatment of SCD-mediated diseases and conditions. Preferably, the other therapeutic agent is selected from antidiabetics, hypolipidemic agents, anti-obesity agents, anti-hypertensive agents or inotropic agents.

Thus, an additional aspect of the present invention concerns a pharmaceutical composition comprising a therapeutically effective amount of a compound of the invention in combination with one or more other therapeutic or diagnostic agents. For example, the composition can be formulated to comprise a therapeutically effective amount of a compound of the invention as defined above, in combination with another therapeutic agent, each at an effective therapeutic dose as reported in the art. Such therapeutic agents may, for example, include insulin, insulin derivatives and mimetics; insulin secretagogues, such as the sulfonylureas, e.g., Glipizide, glyburide and Amaryl; insulinotropic sulfonylurea receptor ligands, such as meglitinides, e.g., nateglinide and repaglinide; PPARγ and/or PPARα (peroxisome proliferator-activated receptor) ligands such as MCC-555, MK767, L-165041, GW7282 or thiazolidinediones such as rosiglitazone, pioglitazone, balaglitazone, troglitazone and the like; insulin sensitizers, such as protein tyrosine phosphatase-1B (PTP-1B) inhibitors such as PTP-112; GSK3 (glycogen synthase kinase-3) inhibitors such as SB-517955, SB-4195052, SB-216763, N,N-57-05441, N,N-57-05445 or RXR ligands such as GW-0791, AGN-194204; sodium-dependent glucose cotransporter inhibitors, such as T-1095, glycogen phosphorylase A inhibitors, such as BAY R3401; biguanides, such as metformin; alpha-glucosidase inhibitors, such as acarbose; GLP-1 (glucagon like peptide-1), GLP-1 analogs, such as Exendin-4, and GLP-1 mimetics; DPPIV (dipeptidyl peptidase IV) inhibitors such as LAF237 (Vildagliptin) or sitagliptin; GIP and GIP mimetics such as those disclosed in WO 00/58360; PACAP and PACAP mimetics, such as those disclosed in WO 01/23420; hypolipidemic agents, such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin, fluindostatin and rivastatin, squalene synthase inhibitors or FXR (farnesoid X receptor) and LXR (liver X receptor) ligands, cholestyramine, fibrates, nicotinic acid and aspirin; anti-obesity agents, such as orlistat, anti-hypertensive agents, inotropic agents and hypolipidemic agents, e.g., loop diuretics, such as ethacrynic acid, furosemide and torsemide; angiotensin converting enzyme (ACE) inhibitors, such as benazepril, captopril, enalapril, fosinopril, lisinopril, moexipril, perinodopril, quinapril, ramipril and trandolapril; inhibitors of the Na-K-ATPase membrane pump, such as digoxin; neutralendopeptidase (NEP) inhibitors; ACE/NEP inhibitors, such as omapatrilat, sampatrilat and fasidotril; angiotensin II antagonists, such as candesartan, eprosartan, irbesartan, losartan, telmisartan and valsartan, in particular valsartan; β-adrenergic receptor blockers, such as acebutolol, atenolol, betaxolol, bisoprolol, metoprolol, nadolol, propranolol, sotalol and timolol; inotropic agents, such as digoxin, dobutamine and milrinone; calcium channel blockers, such as amlodipine, bepridil, diltiazem, felodipine, nicardipine, nimodipine, nifedipine, nisoldipine and verapamil. Other specific antidiabetic compounds are described by Patel Mona (*Expert Opin Investig Drugs*. (2003) April; 12(4):623-33) in the FIGS. 1 to 7. A compound of the present invention may be administered either simultaneously, before or after the other active ingredient, either separately by the same or different route of administration or together in the same pharmaceutical formulation.

The structure of the active agents identified by code numbers (nos.), generic or trade names may be taken from the actual edition of the standard compendium "The Merck Index" or from databases, e.g. Patents International (e.g. IMS World Publications).

In another aspect is the use of the pharmaceutical composition as described above for production of a medicament for the treatment of SCD-mediated disease or condition.

In another aspect is the use of a pharmaceutical composition or combination as described above for the preparation of a medicament for the treatment of conditions associated with stearoyl-CoA desatruase activity.

In another aspect is a pharmaceutical composition as described above for the treatment of conditions associated with the inhibition of stearoyl-CoA desaturase.

Preparations of Compounds

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are well-known to those skilled in the art and as described herein. The use of protecting groups is described in detail in Green, T. W. and P. G. M. Wuts, *Protective Groups in Organic Synthesis* (2006), 4th Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The following reaction schemes illustrate methods to make compounds of this invention. It is understood that one skilled in the art would be able to make these compounds by similar methods or by methods known to one skilled in the art. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described in this invention. $R^1$, $R^2$, $R^3$, $R^4$, $R^{4a}$, $R^5$, $R^{5a}$, and W are defined as in the Specification unless specifically defined. R' is a protecting group.

In general, the compounds of Formula (I) of the invention where W is —N(R$^8$)C(O)—, P is

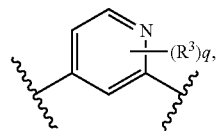

q is 0, Q is

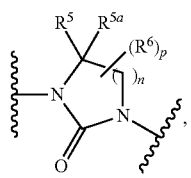

$R^5$ and $R^{5a}$ are hydrogen, n is 1, and p is 0, can be synthesized following the general procedure as described in REACTION SCHEME 1.

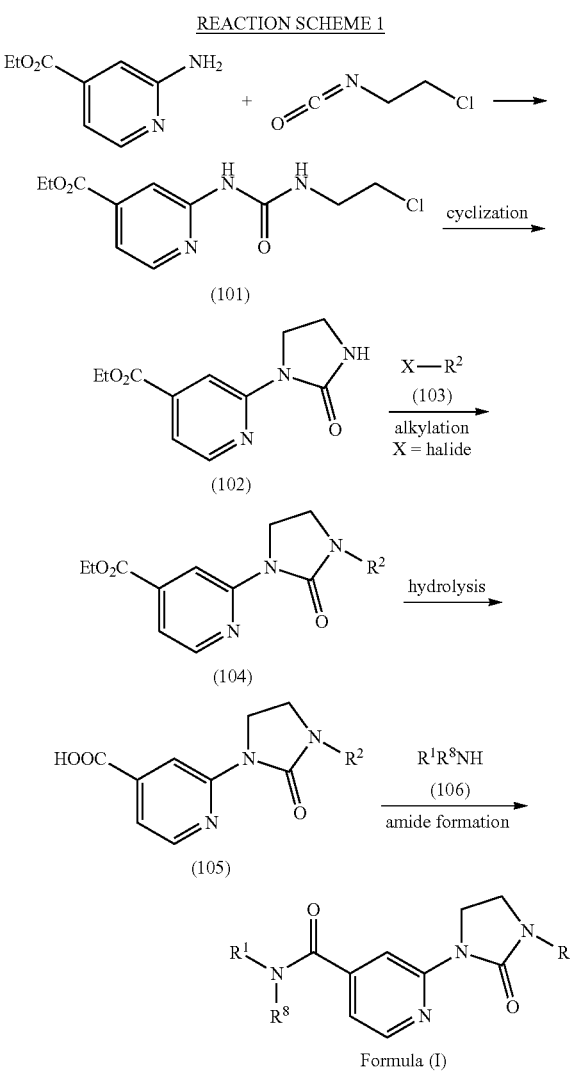

The starting materials for the above reaction scheme are commercially available or can be prepared according to methods known to one skilled in the art or by methods disclosed herein. In general, the compounds of the invention are prepared in the above reaction scheme as follows:

Ethyl 2-aminoisonicotinate reacts with 2-chloroethyl isocyanate to afford compound (101) which undergoes intramolecular cyclization in the presence of a base, such as, but not limited to, potassium carbonate, to afford the cyclized urea compound (102). Compound (102) reacts with a halide (X—R$^2$) compound (103) under alkylation conditions to afford compound (104), which undergoes standard hydrolysis known to one skilled in the art to afford carboxylic acid (105). Compound (105) then undergoes standard amide formation reaction with an amine compound (106) to afford the compound of Formula (I) of the invention where W is —N(R$^8$)C(O)—, P is

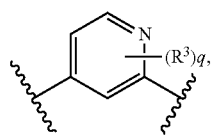

q is 0, Q is

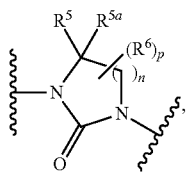

R$^5$ and R$^{5a}$ are hydrogen, n is 1, and p is 0.

Alternatively, the compounds of Formula (I) of this invention where W is —N(R$^8$)C(O)—, P is

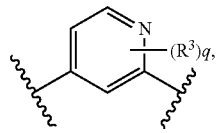

R$^3$ is hydrogen, q is 0, Q is

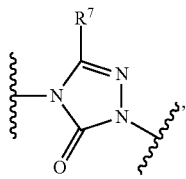

and R$^7$ is hydrogen, can be synthesized following the general procedure as described in REACTION SCHEME 2.

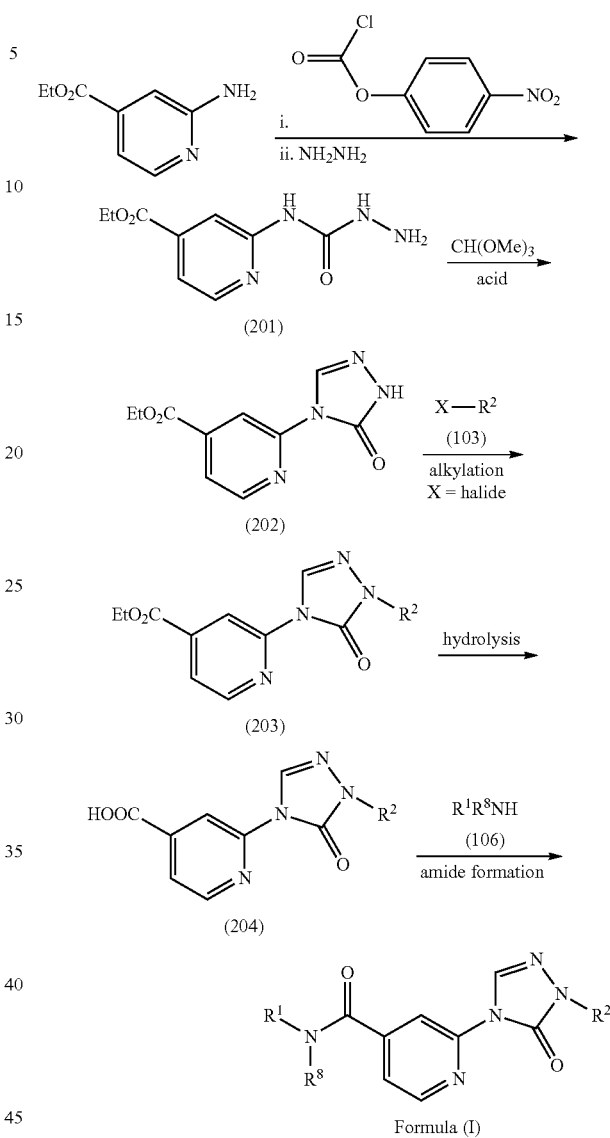

The starting materials for the above reaction scheme are commercially available or can be prepared according to methods known to one skilled in the art or by methods disclosed herein. In general, the compounds of the invention are prepared in the above reaction scheme as follows:

Ethyl 2-aminoisonicotinate reacts with 4-nitrophenyl chloroformate and then with hydrazine to afford compound (201) which undergoes intramolecular cyclization in the presence of trimethyl orthoformate and p-toluenesulfonic acid to afford the triazolone compound (202). Compound (202) reacts with an alkyl halide (X—R$^2$) compound (103) under alkylation conditions to afford compound (203) which undergoes standard hydrolysis known to one skilled in the art to afford carboxylic acid compound (204). Compound (204) then undergoes standard amide formation reaction with an amine compound (106) to afford the compound of Formula (I) of the invention where W is —N(R$^8$)C(O)—, P is

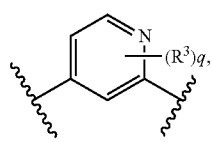

q is 0, Q is

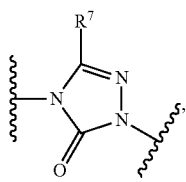

and R⁷ is hydrogen.

Alternatively, the compounds of Formula (II) of this invention where W is —N(R⁸)C(O)—, P is

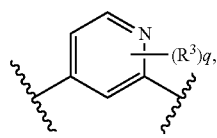

q is 0, Q' is —N(R⁸)C(O)— and R⁸ is hydrogen, can be synthesized following the general procedure as described in REACTION SCHEME 3.

REACTION SCHEME 3

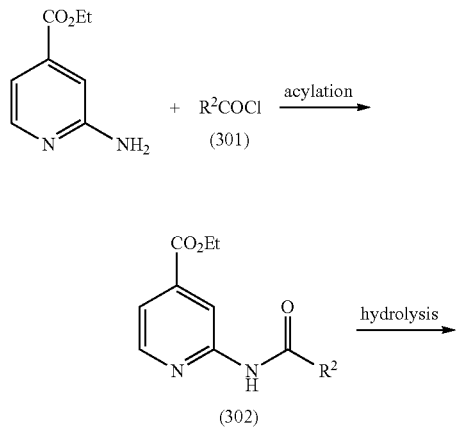

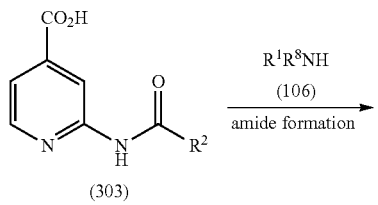

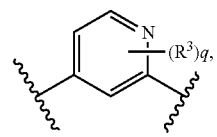

Formula (II)

The starting materials for the above reaction scheme are commercially available or can be prepared according to methods known to one skilled in the art or by methods disclosed herein. In general, the compounds of the invention are prepared in the above reaction scheme as follows:

Ethyl 2-aminoisonicotinate reacts with acid chloride (301) in the presence of a base, such as, but not limited to, pyridine, to afford the compound (302) which undergoes hydrolysis under standard conditions known to one skilled in the art to afford compound (303). Compound (303) reacts with amine compound (106) under standard amide formation reaction conditions known to one skilled in the art to afford the compound of Formula (II) of the invention where W is —N(R⁸)C(O)—, P is

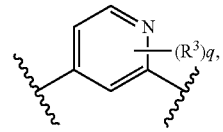

q is 0, Q' is —N(R⁸)C(O)—, and R⁸ is hydrogen.

Alternatively, the compounds of Formula (II) of this invention where W is —N(R⁸)C(O)—, R⁸ is hydrogen, P is

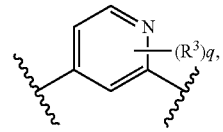

q is 0, Q' is —N(R⁸)C(O)—, and R⁸ is hydrogen, can be synthesized following the general procedure as described in REACTION SCHEME 4.

REACTION SCHEME 4

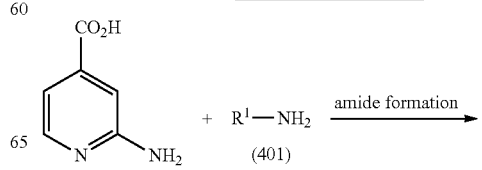

-continued

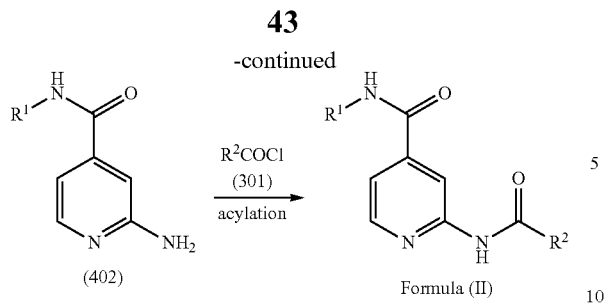

The starting materials for the above reaction scheme are commercially available or can be prepared according to methods known to one skilled in the art or by methods disclosed herein. In general, the compounds of the invention are prepared in the above reaction scheme as follows:

2-Aminoisonicotinic acid reacts with amine compound (401) under standard amide formation reaction conditions known to one skilled in the art to afford compound (402). Compound (402) reacts with acid chloride compound (301) in the presence of a base, such as, but not limited to, pyridine, to afford compound of Formula (II) of the invention where W is —N(R$^8$)C(O)—, R$^8$ is hydrogen, P is

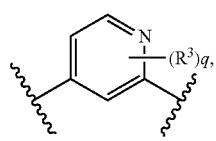

q is 0, Q' is —N(R$^8$)C(O)—, and R$^8$ is hydrogen.

Alternatively, the compounds of Formula (I) of this invention where W is —N(R$^8$)C(O)—, R$^8$ is hydrogen, P is

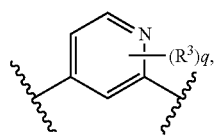

q is 0, and Q is

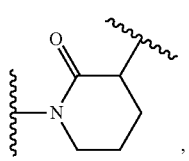 [SMILES: *C1CCCN(*)C1=O]

can be synthesized following the general procedure as described in REACTION SCHEME 5.

REACTION SCHEME 5

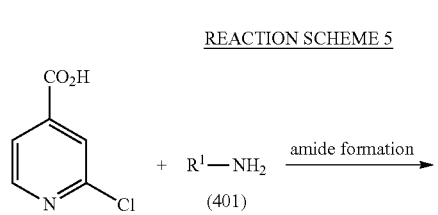

-continued

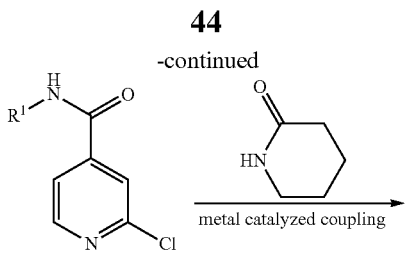

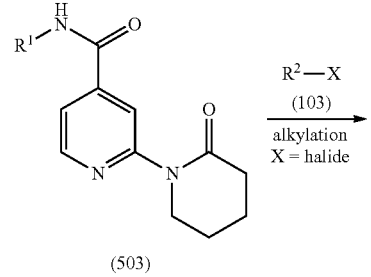

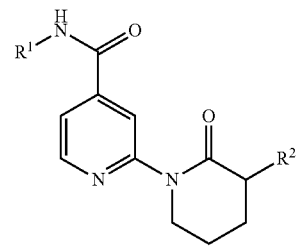

Formula (I)

The starting materials for the above reaction scheme are commercially available or can be prepared according to methods known to one skilled in the art or by methods disclosed herein. In general, the compounds of the invention are prepared in the above reaction scheme as follows:

2-Chloroisonicotinic acid reacts with amine compound (401) under standard amide formation reaction conditions known to one skilled in the art to afford compound (502). Compound (502) reacts with piperidin-2-one under metal catalyzed coupling reaction conditions known to one skilled in the art to afford compound (503). Compound (503) reacts with halide compound (103) in the presence of a base, such as, but not limited to, bis(triethylsilyl)amide, to afford the compound of Formula (I) of the invention where W is —N(R$^8$)C(O)—, R$^8$ is hydrogen, P is

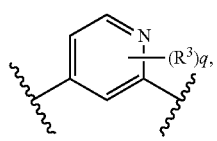

q is 0, and Q is

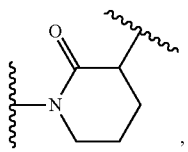 [SMILES: *C1CCCN(*)C1=O]

Alternatively, the compounds of Formula (II) where W is —N(R$^8$)C(O)—, R$^8$ is hydrogen, P is

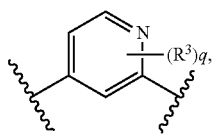

q is 1, $R^3$ is 2-hydroxyl, Q' is —N($R^8$)C(O)—, and $R^8$ is hydrogen of this invention can be synthesized following the general procedure as described in REACTION SCHEME 6.

REACTION SCHEME 6

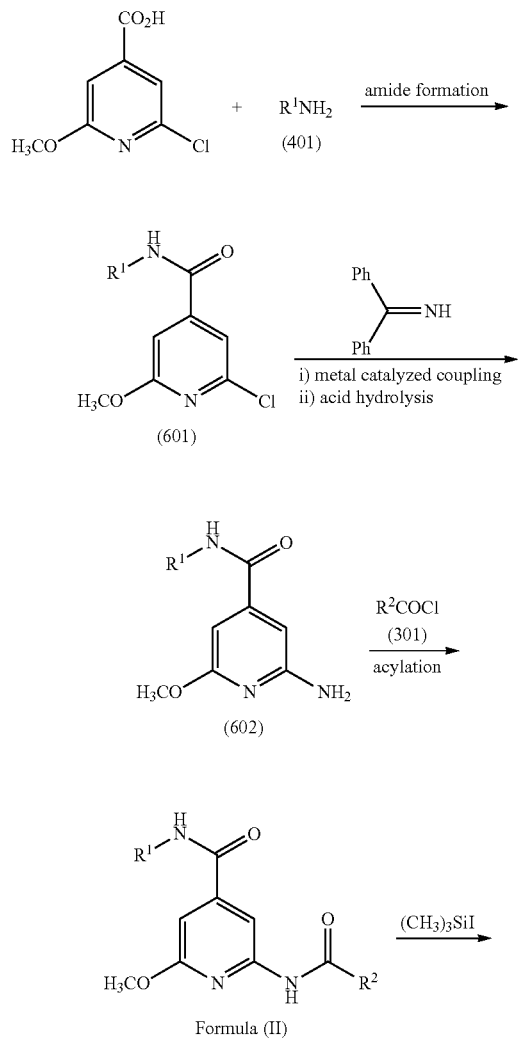

The starting materials for the above reaction scheme are commercially available or can be prepared according to methods known to one skilled in the art or by methods disclosed herein. In general, the compounds of the invention are prepared in the above reaction scheme as follows:

2-Chloro-6-methoxyisonicotinic acid reacts with amine compound (401) under standard amide formation reaction conditions known to one skilled in the art to afford compound (601). Compound (601) reacts with benzophenone imine under metal catalyzed coupling reaction conditions known to one skilled in the art followed by hydrolysis in the presence of acid to afford compound (602). Acylation of compound (602) with acid chloride (301) in the presence of a base, such as, but not limited to, pyridine, affords the compound of Formula (II) of the invention where W is —N($R^8$)C(O)—, $R^8$ is hydrogen, P is

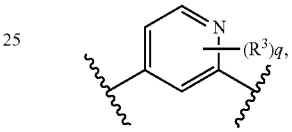

q is 1, $R^3$ is 2-methoxyl, and Q' is —N($R^8$)C(O)—, and $R^8$ is hydrogen. Removal of the methyl group of this compound with iodotrimethylsilane affords the compound of Formula (II) of the invention where W is —N($R^8$)C(O)—, $R^8$ is hydrogen, P is

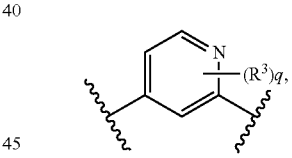

q is 1, $R^3$ is 2-hydroxyl, Q' is —N($R^8$)C(O)—, and $R^8$ is hydrogen.

Alternatively, the compounds of Formula (II) of this invention where W is a direct bond, P is

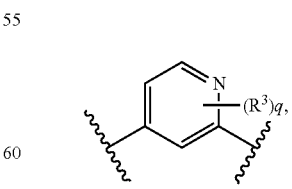

q is 0, Q' is —N($R^8$)C(O)—, and $R^8$ is hydrogen, can be synthesized following the general procedure as described in REACTION SCHEME 7.

REACTION SCHEME 7

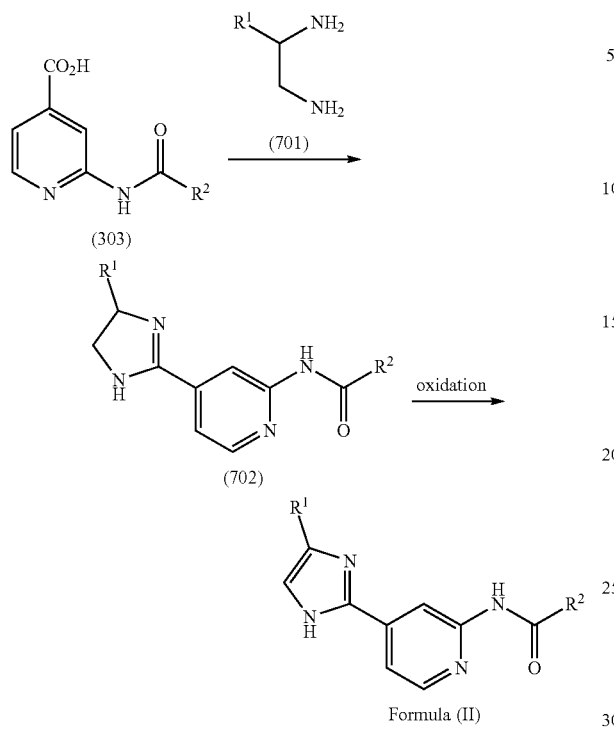

The starting materials for the above reaction scheme are commercially available or can be prepared according to methods known to one skilled in the art or by methods disclosed herein. In general, the compounds of the invention are prepared in the above reaction scheme as follows:

The carboxylic acid compound (303) reacts with diamine compound (701) in the presence of phorous oxychloride to afford compound (702) which undergoes oxidation reaction in the presence of an oxidizing agent, such as, but not limited to, oxalyl chloride and dimethyl sulfoxide, to afford the compound of Formula (II) of the invention where W is a direct bond, P is

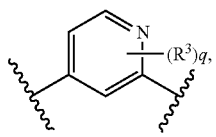

q is 0, Q' is —N(R$^8$)C(O)—, and R$^8$ is hydrogen.

Alternatively, the compounds of Formula (II) of this invention where W is a direct bond, P is

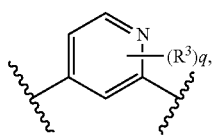

q is 0, Q' is —N(R$^8$)C(O)—, and R$^8$ is hydrogen can be synthesized following the general procedure as described in REACTION SCHEME 8.

REACTION SCHEME 8

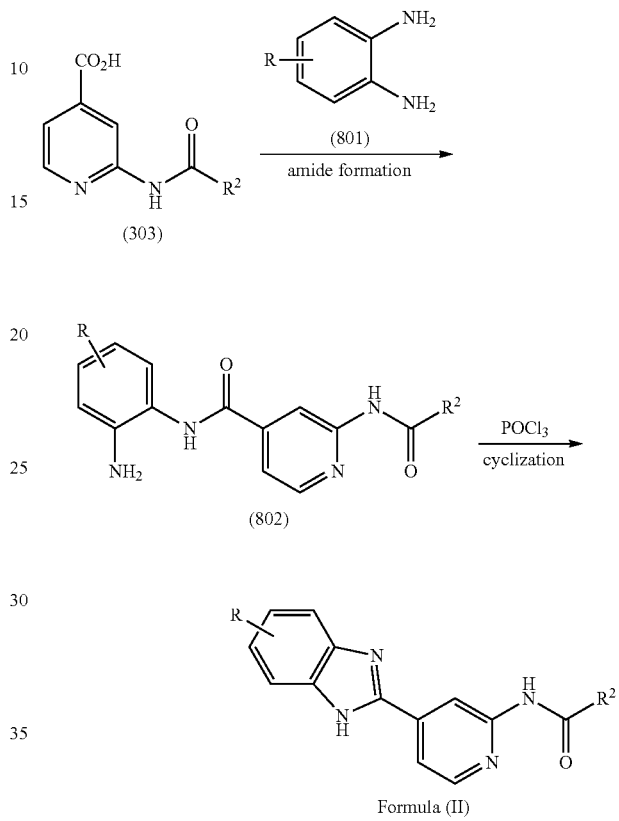

The starting materials for the above reaction scheme are commercially available or can be prepared according to methods known to one skilled in the art or by methods disclosed herein. In general, the compounds of the invention are prepared in the above reaction scheme as follows:

The carboxylic acid (303) reacts with a substituted 1,2-diaminobenzene (801) under standard amide formation conditions known to one skilled in the art to afford compound (802) which undergoes cyclization in the presence of phosphorous oxychloride to afford compound of Formula (II) of the invention where W is a direct bond, P is

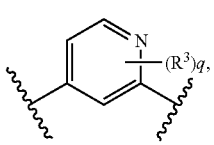

q is 0, Q' is —N(R$^8$)C(O)—, and R$^8$ is hydrogen.

Alternatively, the compounds of Formula (II) of this invention can be synthesized following the general procedure as described in REACTION SCHEME 9.

REACTION SCHEME 9

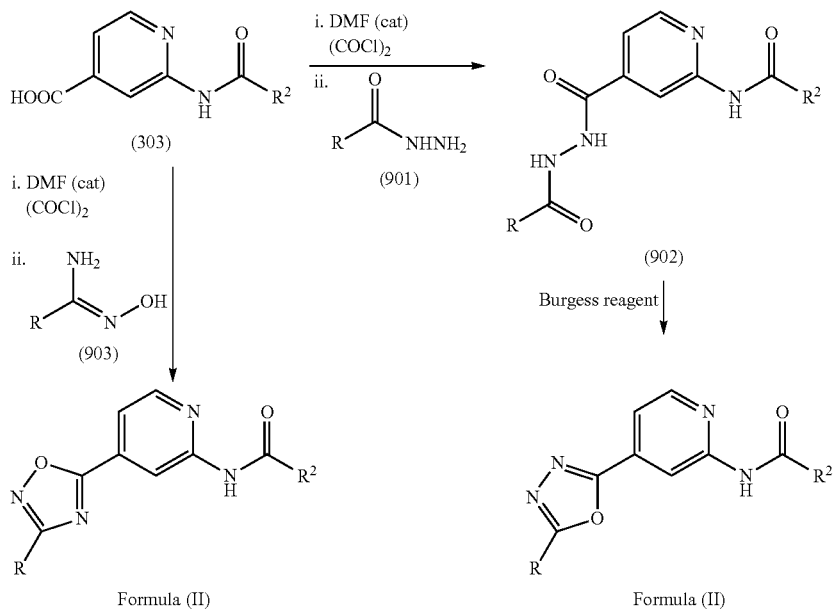

Formula (II)                  Formula (II)

The starting materials for the above reaction scheme are commercially available or can be prepared according to methods known to one skilled in the art or by methods disclosed herein. In general, the compounds of the invention are prepared in the above reaction scheme as follows:

The carboxylic acid (303) reacts with oxalyl chloride followed by the reaction with hydrazide compound (901) to afford compound (902). Compound (902) is dehydrated by Burgess reagent to afford the compound of Formula (II) of the invention where $R^1$ is substituted 1,3,4-oxadiazole, W is a direct bond, P is

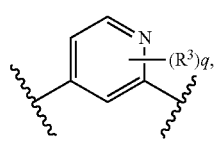

q is 0, Q' is —N($R^8$)C(O)—, and $R^8$ is hydrogen. Alternatively, the carboxylic acid (303) reacts with oxalyl chloride followed by the reaction with N'-hydroxyacetimidamide (903). The intermediate obtained is dehydrated by Burgess reagent to afford the compound of Formula (II) of the invention where $R^1$ is substituted 1,2,4-oxadiazole, W is a direct bond, P is

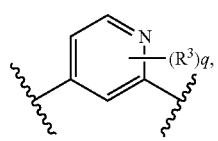

q is 0, Q' is —N($R^8$)C(O)—, and $R^8$ is hydrogen.

Alternatively, the compounds of Formula (I) of this invention can be synthesized following the general procedure as described in REACTION SCHEME 10.

REACTION SCHEME 10

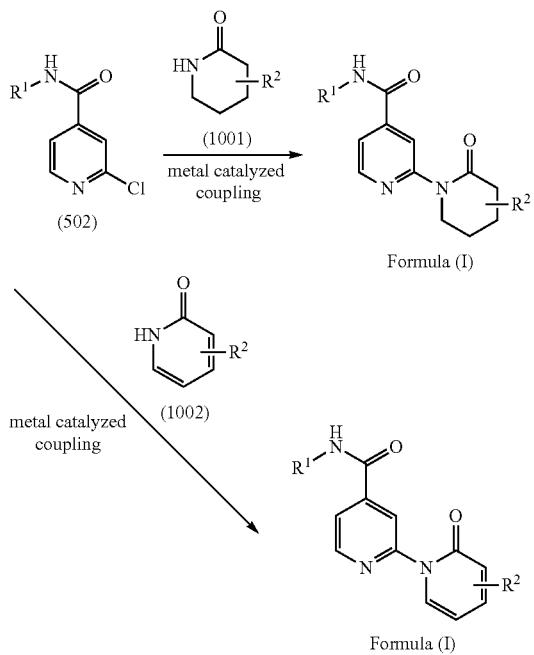

The starting materials for the above reaction scheme are commercially available or can be prepared according to methods known to one skilled in the art or by methods disclosed herein. In general, the compounds of the invention are prepared in the above reaction scheme as follows:

The chloroisonicotinamide compound (502) is coupled with piperidinone compound (1001) under metal catalyzed coupling reaction conditions known to one skilled in the art to afford compound of Formula (I) of the invention where W is —N($R^8$)C(O)—, $R^8$ is hydrogen, P is

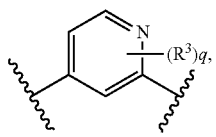

q is 0, and Q is

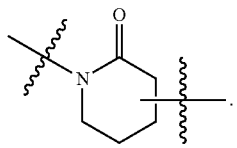

Alternatively, chloroisonicotinamide compound (502) is coupled with pyridinone compound (1002) under metal catalyzed coupling reaction conditions known to one skilled in the art to afford the compound of Formula (I) of the invention where W is —N(R$^8$)C(O)—, R$^8$ is hydrogen, P is

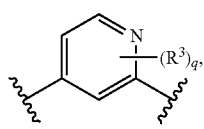

q is 0, and Q is

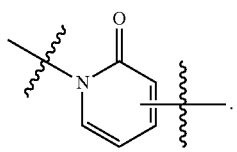

Preparation 1

Preparation of ethyl 2-benzamidoisonicotinate

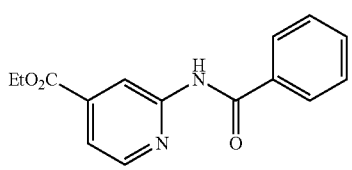 [SMILES: CCOC(=O)c1ccnc(NC(=O)c2ccccc2)c1]

To a solution of ethyl 2-aminoisonicotinate (1.00 g, 6.02 mmol) in anhydrous pyridine (13 mL) was added benzoyl chloride (0.77 mL, 6.63 mmol) dropwise at 0° C. under nitrogen atmosphere. The resulting solution was warmed to ambient temperature, stirred for 18 hours and concentrated in vacuo. The residue was dissolved in ethyl acetate (75 mL), washed with 2 M aqueous hydrochloric acid solution (20 mL) and saturated aqueous sodium bicarbonate solution (20 mL). The organic solution was dried over anhydrous sodium sulphate, filtered and concentrated in vacuo. The residue was purified by column chromatography eluted with 10-50% ethyl acetate in hexanes to give ethyl 2-benzamidoisonicotinate as a colorless solid (1.35 g, 83%): $^1$H NMR (300 MHz, CDCl$_3$) δ 8.94 (s, 1H), 8.84 (br s, 1H), 8.43 (d, J=5.1 Hz, 1H), 7.98-7.93 (m, 2H), 7.70-7.47 (m, 4H), 4.44 (q, J=7.1 Hz, 2H), 1.43 (t, J=7.1 Hz, 3H); MS (ES+) m/z 271.5 (M+1).

Preparation 2

Preparation of 2-benzamidoisonicotinic acid

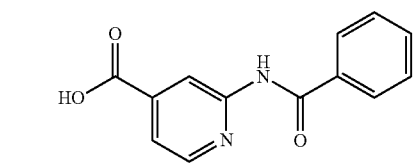 [SMILES: O=C(O)c1ccnc(NC(=O)c2ccccc2)c1]

A solution of ethyl 2-benzamidoisonicotinate (1.38 g, 5.09 mmol) and lithium hydroxide monohydrate (1.07 g, 24.45 mmol) in a mixture of tetrahydrofuran (30 mL) and water (15 mL) was stirred at ambient temperature for 4 hours and the organic solvent was removed in vacuo. The aqueous solution was acidified with 10% aqueous hydrochloric acid solution until pH 7. The colorless solid was collected and dried in vacuo to give 2-benzamidoisonicotinic acid as a colorless solid (1.10 g, 89%): $^1$H NMR (300 MHz, DMSO-d$_6$) δ 13.69 (s, 1H), 11.95 (s, 1H), 8.71 (s, 1H), 8.57-8.56 (m, 1H), 8.05-8.03 (m, 2H), 7.61-7.50 (m, 4H); MS (ES+) m/z 243.1 (M+1).

Preparation 3

Preparation of 2-benzamidoisonicotinic (isobutyl carbonic) anhydride

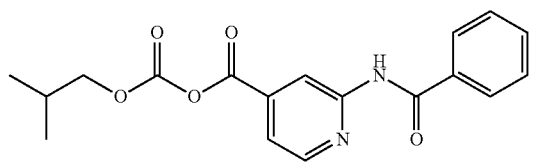 [SMILES: CC(C)COC(=O)OC(=O)c1ccnc(NC(=O)c2ccccc2)c1]

To a solution of 2-benzamidoisonicotinic acid (0.20 g, 0.83 mmol) in anhydrous N,N-dimethylformamide (12 mL) and N-methylmorpholine (0.09 mL, 0.83 mmol) was added isobutyl chloroformate (0.11 mL, 0.83 mmol) dropwise at 0° C. under nitrogen atmosphere. The resulting solution was stirred for 1 hour at 0° C. and 3 hours at ambient temperature. The resulting stock solution was used for further reactions.

Preparation 4

Preparation of N-benzyl-2-chloroisonicotinamide

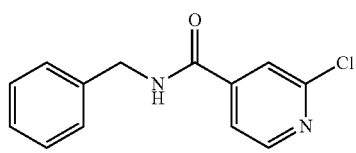 [SMILES: O=C(NCc1ccccc1)c1ccnc(Cl)c1]

A solution of 2-chloroisonicotinic acid (5.00 g, 31.7 mmol) in thionyl chloride (25 mL) was refluxed for 30 minutes and concentrated in vacuo to dryness. The residue was dissolved in dichloromethane (100 mL) and added to a mixture of benzylamine (3.40 g, 31.7 mmol) and triethylamine (6.64 mL, 47.6 mmol) in dichloromethane (40 mL). The resulting solution was stirred at ambient temperature for 16 hours, washed with saturated sodium bicarbonate solution (30 mL), water (30 mL) and brine (30 mL). The separated organic solution was dried over anhydrous sodium sulphate, filtered and concentrated in vacuo. The residue was purified by column chromatography and eluted with 60-80% ethyl acetate in hexanes to give N-benzyl-2-chloroisonicotinamide as a colorless solid (5.35 g, 49%): $^1$H NMR (300 MHz, DMSO-d$_6$) δ 9.44-9.40 (m, 1H), 8.56 (d, J=5.1 Hz, 1H), 7.91 (s, 1H), 7.82-7.80 (m, 1H), 7.34-7.25 (m, 5H), 4.49 (d, J=5.1 Hz, 2H), MS (ES+) m/z 247.2 (M+1).

Preparation 5

Preparation of
N-benzyl-2-(2-oxopiperidin-1-yl)isonicotinamide

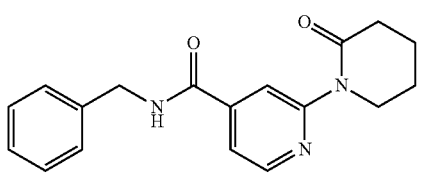 [SMILES: O=C(NCc1ccccc1)c1ccnc(N2CCCCC2=O)c1]

A mixture of N-benzyl-2-chloroisonicotinamide (0.30 g, 1.22 mmol), piperidin-2-one (0.12 g, 1.22 mmol), 1,1'-bis(diphenylphosphino)ferrocene (0.03 g, 0.05 mmol), palladium acetate (0.01 g, 0.05 mmol) and sodium tert-butoxide (0.12 g, 1.22 mmol) in toluene (10 mL) was heated at 130° C. for 36 hours under nitrogen atmosphere and concentrated in vacuo to dryness. The residue was dissolved in dichloromethane (50 mL) and washed with water (30 mL). The separated organic solution was dried over anhydrous sodium sulphate, filtered and concentrated in vacuo. The residue was purified by column chromatography and eluted with 65-75% ethyl acetate in petroleum ether to give N-benzyl-2-(2-oxopiperidin-1-yl)isonicotinamide as a colorless solid (0.08 g, 21%): MS (ES+) m/z 310.1 (M+1).

Preparation 6

Preparation of 2-amino-N-benzylisonicotinamide

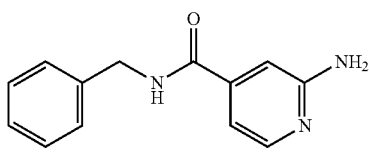 [SMILES: Nc1cc(C(=O)NCc2ccccc2)ccn1]

To a solution of 2-aminoisonicotinic acid (2.76 g, 20.0 mmol) in N,N-dimethylformamide (60 mL) was added 1-(3-dimethylaminopropyl)-3-ethylcarbodiimide hydrochloride (5.00 g, 26.0 mmol) and N,N-diisopropylethylamine (10 mL, 57.7 mmol). The resulting solution was stirred for 30 minutes at ambient temperature followed by the addition of 1-hydroxybenzotriazole (3.24 g, 24.0 mmol) and benzylamine (3.2 mL, 29.3 mmol). The reaction mixture was stirred for 72 hours at ambient temperature, diluted with water (30 mL) and extracted with ethyl acetate (200 mL×4). The combined organic layers were washed with brine (30 mL), dried over anhydrous sulphate, filtered and concentrated in vacuo. The residue was triturated with ethyl acetate and hexanes (in a 1:10 ratio), filtered and dried in vacuo to give 2-amino-N-benzylisonicotinamide as a colorless solid (1.97 g, 43%): NMR (300 MHz, CDCl$_3$) δ 8.11-8.09 (m, 1H), 7.37-7.27 (m, 5H), 6.88-6.82 (m, 2H), 6.42 (br s, 1H), 4.60 (d, J=5.7 Hz, 2H); MS (ES+) m/z 228.5 (M+1).

Preparation 7

Preparation of
N-benzyl-2-chloro-6-methoxyisonicotinamide

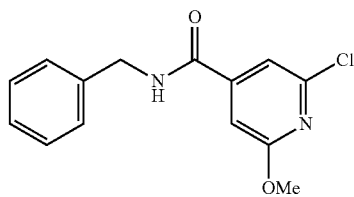 [SMILES: COc1cc(C(=O)NCc2ccccc2)cc(Cl)n1]

To a solution of 2-chloro-6-methoxyisonicotinic acid (4.90 g, 26.00 mmol, prepared according to Okajima S., *Yakugaku Zasshi*, (1953), 73, 845-847) and 4-methylmorpholine (3.3 mL, 30.00 mmol) in tetrahydrofuran (100 mL) was added isobutyl chloroformate (3.8 mL, 28.00 mmol) at 0° C. The resulting solution was stirred at ambient temperature for 1 hour, followed by the addition of benzylamine (4.2 mL, 38.00 mmol). The reaction mixture was stirred at ambient temperature for 20 hours, diluted with ethyl acetate (100 mL), washed with water (30 mL) and brine (30 mL). The organic solution was dried over anhydrous sulphate, filtered and concentrated in vacuo. The residue was recrystallized from ethyl acetate and hexanes to give N-benzyl-2-chloro-6-methoxyisonicotinamide (6.20 g, 86%): $^1$H NMR (300 MHz, CDCl$_3$) δ 7.37-7.27 (m, 5H), 7.18 (s, 1H), 6.94 (s, 1H), 6.43 (br s, 1H), 4.58 (d, J=5.7 Hz, 2H), 3.94 (s, 3H); MS (ES+) m/z 277.4 (M+1).

Preparation 8

Synthesis of
2-amino-N-benzyl-6-methoxyisonicotinamide

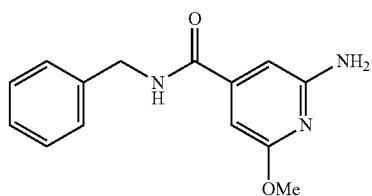 [SMILES: COc1cc(C(=O)NCc2ccccc2)cc(N)n1]

To a degassed mixture of N-benzyl-2-chloro-6-methoxyisonicotinamide (1.38 g, 5.00 mmol), benzophenone imine (1.0 mL, 5.78 mmol), sodium t-butoxide (1.20 g, 12.0 mmol) and rac-2,2'-bis(diphenylphosphino)-1,1'-binaphthyl (0.02 g, 0.03 mmol) in toluene (40 mL) was added tris(dibenzylideneacetone)dipalladium (0.01 g, 0.01 mmol). The resulting solution was heated at 90° C. for 18 hours and concentrated in vacuo. The residue was dissolved in a mixture of tetrahydrofuran (20 mL) and 10% hydrochloric acid solution (20 mL) and stirred for 20 hours at ambient temperature. The resulting solution was neutralized with saturated sodium bicarbonate solution until pH 8-9 and extracted with ethyl acetate (3×50 mL). The combined organic layers were washed with brine (30 mL), dried over anhydrous sodium sulfate, filtered and concentrated in vacuo. The residue was purified by column chromatography to give 2-amino-N-benzyl-6-methoxyisonicotinamide (0.80 g, 62%): MS (ES+) m/z 258.5 (M+1).

Preparation 9

Preparation of methyl 2-amino-3-(3,5-difluorophenyl)propanoate hydrochloride

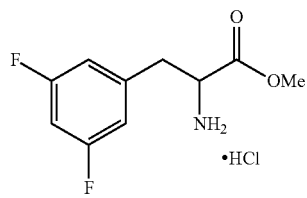 [SMILES: COC(=O)C(N)Cc1cc(F)cc(F)c1 ; Cl]

To a stirred suspension of DL-3,5-difluorophenylalanine (3.00 g, 14.9 mmol) in anhydrous methanol (30 mL) was added dropwise thionyl chloride (1.64 mL, 22.5 mmol) at 0° C. The resulting solution was refluxed for 18 hours, cooled to ambient temperature and concentrated in vacuo to dryness. The residue was triturated with diethyl ether to give methyl 2-amino-3-(3,5-difluorophenyl)propanoate hydrochloride as a colorless crystalline solid (3.68 g, 98%): $^1$H NMR (300 MHz, CD$_3$OD) δ 6.93-6.84 (m, 3H), 4.34 (dd, J=7.4, 6.3 Hz, 1H), 3.78 (s, 3H), 3.30-3.09 (m, 2H).

Preparation 10

Preparation of 2-amino-3-(3,5-difluorophenyl)propanamide

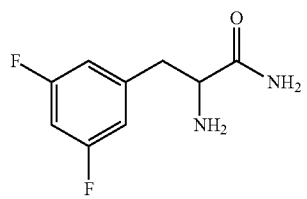 [SMILES: NC(=O)C(N)Cc1cc(F)cc(F)c1]

A solution of methyl 2-amino-3-(3,5-difluorophenyl)propanoate hydrochloride (3.67 g, 14.6 mmol) in aqueous ammonium hydroxide (5.5 mL) and water (22 mL) was stirred at ambient temperature for 18 hours and extracted with dichloromethane (4×50 mL). The combined organic layers were dried over anhydrous sodium sulphate, filtered and concentrated in vacuo to dryness to give 2-amino-3-(3,5-difluorophenyl)propanamide as a colorless solid (1.50 g, 51%): $^1$H NMR (300 MHz, CD$_3$OD) δ 6.92-6.75 (m, 3H), 3.56 (dd, J=7.3, 6.3 Hz, 1H), 3.00 (dd, J=13.4, 6.3 Hz, 1H), 2.83 (dd, J=13.4, 7.4 Hz, 1H).

Preparation 11

Preparation of pentane-1,2-diamine

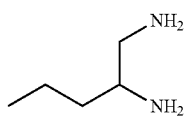

To a solution of 2-aminopentanenitrile (1.18 g, 12.02 mmol, prepared according to Deng et al, Synthesis, (2001), 16, 2445-2449) in anhydrous tetrahydrofuran (10 mL) was added dropwise lithium aluminum hydride (7.2 mL of 2 M solution in tetrahydrofuran, 14.4 mmol) at 0° C. The resulting reaction mixture was refluxed for 2 hours, cooled to 0° C. and quenched with sodium sulfate decahydrate. The resulting precipitate was filtered and washed with ethyl acetate (200 mL). The filtrate was dried over anhydrous sodium sulphate and concentrated in vacuo to dryness to give pentane-1,2-diamine as a light yellow oil (0.62 g, 50%): $^1$H NMR (300 MHz, CDCl$_3$) δ 2.88-1.65 (m, 3H), 1.59-1.08 (m, 4H), 0.98-0.77 (m, 3H).

Preparation 11.1

Preparation of (S)-3-phenylpropane-1,2-diamine

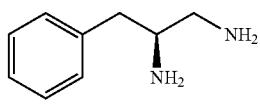 [SMILES: NC[C@@H](N)Cc1ccccc1]

Following the procedure as described in Preparation 11, making variations as required to replace 2-aminopentanenitrile with L-phenylalanineamide to react with lithium aluminum hydride, (S)-3-phenylpropane-1,2-diamine was obtained as a colorless solid in 35% yield: MS (ES+) m/z 151.2 (M+1).

Preparation 11.2

Preparation of (S)-4-methylpentane-1,2-diamine

Following the procedure as described in Preparation 11, making variations as required to replace 2-aminopentanenitrile with L-leucinamide to react with lithium aluminum hydride, (S)-4-methylpentane-1,2-diamine was obtained as a colorless solid in 75% yield: $^1$H NMR (300 MHz, CDCl$_3$) δ

2.80-2.64 (m, 2H), 2.49-2.34 (m, 1H), 1.81-1.58 (m, 1H), 1.40 (br s, 4H), 1.23-1.11 (m, 2H), 1.00-0.80 (m, 6H).

Preparation 11.3

Preparation of 3-(3,5-difluorophenyl)propane-1,2-diamine

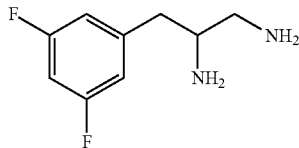 [SMILES: NCC(N)Cc1cc(F)cc(F)c1]

Following the procedure as described in Preparation 11, making variations as required to replace 2-aminopentanenitrile with 2-amino-3-(3,5-difluorophenyl)-propanamide to react with lithium aluminum hydride, 3-(3,5-difluorophenyl)propane-1,2-diamine was obtained as a colorless solid in 75% yield: The crude product was used for the next step.

Preparation 11.4

Preparation of 1-phenylethane-1,2-diamine

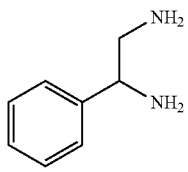

Following the procedure as described in Preparation 11, making variations as required to replace 2-aminopentanenitrile with 2-amino-2-phenylacetonitrile, (Crossley et al., *J. Chem., Perkin Trans.* 1, (1974), 2327-2330) to react with lithium aluminum hydride, 1-phenylethane-1,2-diamine was obtained as a colorless solid in 35% yield. The crude product was used for the next reaction.

Preparation 12

Preparation of methyl 2-(3-((4-(difluoromethyl)phenyl)difluoromethyl)-2-oxoimidazolidin-1-yl)isonicotinate

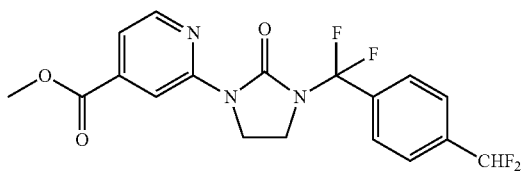 [SMILES: COC(=O)c1ccnc(N2CCN(C(F)(F)c3ccc(C(F)F)cc3)C2=O)c1]

To a solution of 2-(2-oxoimidazolidin-1-yl)isonicotinate (0.50 g, 2.26 mmol) in N,N-dimethylformamide (15 mL) was added sodium hydride (0.10 g, 60% dispersion in mineral oil, 2.5 mmol) at 0° C. The resulting solution was stirred at 0° C. for 30 minutes, followed by the addition of 1-(bromodifluoromethyl)-4-(difluoromethyl)benzene (0.58 g, 2.26 mmol). The mixture was warmed to ambient temperature and stirred for 55 hours. 1-(Bromodifluoromethyl)-4-(difluoromethyl)benzene (0.13 g, 0.5 mmol) was again added and the reaction was stirred at 60° C. for 5 hours then concentrated in vacuo to dryness. The residue was purified by column chromatography eluting with hexanes and ethyl acetate (from 10:1 to 1:1) to give methyl 2-(3-((4-(difluoromethyl)phenyl)-difluoromethyl)-2-oxoimidazolidin-1-yl)isonicotinate as a colorless solid (0.09 g, 13%): MS (ES+) m/z 397.8 (M+1).

Preparation 13

Preparation of N-(4-(2-benzoylhydrazinecarbonyl)pyridin-2-yl)benzamide

To a solution of 2-benzamidoisonicotinic acid (0.30 g, 1.23 mmol) and N,N-dimethylformamide (0.1 mL) in dichloromethane (5 mL) was added oxalyl chloride (0.13 mL, 1.48 mmol) at ambient temperature. The reaction mixture was stirred for 1 hour and concentrated in vacuo. The residue was dissolved in N,N-dimethylformamide (2 mL) and added to a solution of benzohydrazide (0.20 g, 1.48 mmol) and pyridine (0.3 mL, 3.70 mmol) in N,N-dimethylformamide (1 mL) at 0° C. The reaction mixture was warmed to ambient temperature, stirred for 3 hours, diluted with ethyl acetate (30 mL), and washed with water (25 mL) and brine (25 mL). The organic solution was dried over anhydrous sodium sulfate, filtered and concentrated in vacuo. The residue was recrystallized from ethyl acetate to give N-(4-(2-benzoylhydrazinecarbonyl)pyridin-2-yl)benzamide (0.30 g, 67%): $^1$H NMR (300 MHz, DMSO-$d_6$) δ 11.01 (s, 1H), 10.80 (s, 1H), 10.59 (s, 1H), 8.61 (s, 1H), 8.02-7.88 (m, 5H), 7.65-7.49 (m, 7H); MS (ES+) m/z 361.4 (M+1).

Preparation 13.1

Preparation of N-(4-(2-(2-phenylacetyl)hydrazinecarbonyl)pyridin-2-yl)benzamide

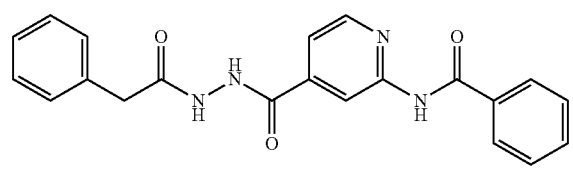 [SMILES: O=C(Cc1ccccc1)NNC(=O)c1ccnc(NC(=O)c2ccccc2)c1]

Following the procedure as described in Preparation 13, making variations as required to replace benzohydrazide with 2-phenylacetohydrazide to react with 2-benzamidoisonicotinic acid, N-(4-(2-(2-phenylacetyl)hydrazinecarbonyl)pyridin-2-yl)benzamide was obtained in 65% yield: MS (ES+) m/z 374.9 (M+1).

Preparation 14

Preparation of methyl 2-(2-oxoimidazolidin-1-yl)isonicotinate

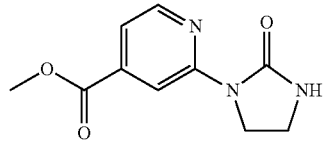 [SMILES: COC(=O)c1ccnc(N2CCNC2=O)c1]

A solution of methyl 2-aminoisonicotinate (5.00 g, 32.9 mmol) and 2-chloroethyl isocyanate (4.51 g, 42.7 mmol) in anhydrous tetrahydrofuran (85 mL) was stirred at ambient temperature for 17 hours and refluxed for 3 hours, followed by the addition of triethylamine (10 mL) and potassium carbonate (9.60 g, 69.50 mmol). The reaction mixture was refluxed for 23 hours, cooled to ambient temperature and filtered. The solid residue was washed with water (2×20 mL) hexanes (2×20 mL) and dried in vacuo to give methyl 2-(2-oxoimidazolidin-1-yl)isonicotinate as a colorless solid (4.22 g, 58%): $^1$H NMR (300 MHz, DMSO-d$_6$) δ 8.67 (s, 1H), 8.40 (d, J=5.1 Hz, 1H), 7.35-7.33 (m, 2H), 2.97 (t, J=7.5 Hz, 2H), 3.85 (s, 3H), 3.41-3.36 (m, 2H); MS (ES+) m/z 222.1.

Preparation 15

Preparation of methyl 2-(hydrazinecarboxamido)isonicotinate

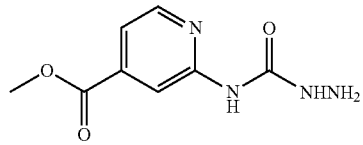

To a solution of methyl 2-aminoisonicotinate (5.00 g, 32.9 mmol) and pyridine (3.90 g, 49.3 mmol) in anhydrous tetrahydrofuran (100 mL) and dichloromethane (100 mL) was added 4-nitrophenyl chloroformate (7.95 g, 39.4 mmol) at 0° C. The resulting solution was stirred for 1 hour at ambient temperature and filtered. The solid was washed with tetrahydrofuran (30 mL) and concentrated in vacuo to dryness. The residue was dissolved in tetrahydrofuran (40 mL), followed by the addition of hydrazine monohydrate (6.50 mL, 134.00 mmol). The mixture was stirred for 17 hours at ambient temperature and filtered. The solid was washed with water (20 mL) and ethyl acetate (20 mL) then dried in vacuo to give methyl 2-(hydrazinecarboxamido)isonicotinate as a yellowish solid (4.05 g, 59%): MS (ES+) m/z 211.1 (M+1).

Preparation 16

Preparation of methyl 2-(5-oxo-1H-1,2,4-triazol-4(5H)-yl)isonicotinate

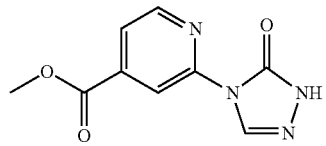 [SMILES: COC(=O)c1ccnc(-n2cn[nH]c2=O)c1]

To a solution of 2-(hydrazinecarboxamido)isonicotinate (2.10 g, 10.0 mmol) in ethanol (140 mL) was added trimethyl orthoformate (2.43 g, 22.9 mmol) and p-toluenesulfonic acid monohydrate (0.70 g, 3.68 mmol) at ambient temperature. The reaction mixture was refluxed for 4 hours, cooled to ambient temperature and concentrated in vacuo to a minimum amount of volume. The solid was filtered, washed with cold methanol (20 mL) and dried in vacuo to give methyl 2-(5-oxo-1H-1,2,4-triazol-4(5H)-yl)isonicotinate as a colorless solid (1.68 g, 76%): MS (ES+) m/z 221.1 (M+1).

Preparation 17

Preparation of methyl 2-(3-(4-fluorobenzyl)-2-oxoimidazolidin-1-yl)isonicotinate

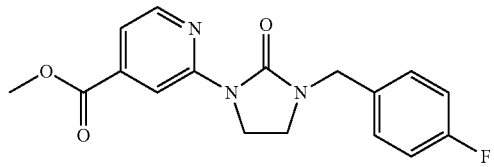

To a solution of 2-(2-oxoimidazolidin-1-yl)isonicotinate (10.00 g, 45.20 mmol) in N,N-dimethylformamide (300 mL) was added sodium hydride (60% dispersion in mineral oil, 1.90 g, 45.20 mmol) at 0° C. The resulting solution was stirred for 30 minutes at 0° C., followed by the addition of 1-(bromomethyl)-4-fluorobenzene (8.54 g, 45.20 mmol). The reaction mixture was warmed to ambient temperature, stirred for 17 hours and concentrated in vacuo to dryness. The residue was purified by column chromatography eluted with dichloromethane and ethyl acetate to give methyl 2-(3-(4-fluorobenzyl)-2-oxoimidazolidin-1-yl)isonicotinate as a colorless solid (10.03 g, 67%): mp 119-121° C.; $^1$H NMR (300 MHz, CDCl$_3$) δ 8.87 (d, J=0.6 Hz, 1H), 8.35 (d, J=5.4 Hz, 1H), 7.45-7.43 (m, 1H), 7.29-7.25 (m, 2H), 7.04-6.98 (m, 2H), 4.44 (s, 2H), 4.20 (t, J=7.8 Hz, 2H), 3.91 (s, 3H), 3.35 (t, J=7.8 Hz, 2H); $^{13}$C NMR (75 MHz, CDCl$_3$) δ 165.9, 164.0, 160.7, 156.8, 153.4, 148.0, 138.7, 132.3, 130.0, 116.7, 115.8, 115.5, 112.5, 52.6, 47.8, 41.3, 41.0; MS (ES+) m/z 330.2 (M+1).

Preparation 17.1

Preparation of methyl 2-(3-(cyclopropylmethyl)-2-oxoimidazolidin-1-yl)isonicotinate

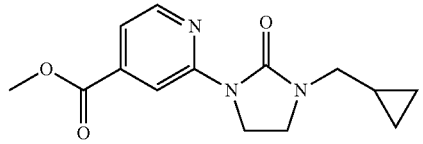 [SMILES: COC(=O)c1ccnc(N2CCN(CC3CC3)C2=O)c1]

Following the procedure as described in Preparation 17, making variations as required to replace 1-(bromomethyl)-4-fluorobenzene with (bromomethyl)cyclopropane to react with 2-(2-oxoimidazolidin-1-yl)isonicotinate, methyl 2-(3-(cyclopropylmethyl)-2-oxoimidazolidin-1-yl)isonicotinate was obtained as a colorless solid in 69% yield: mp 75-77° C.; $^1$H NMR (300 MHz, DMSO-d$_6$) δ 8.69 (s, 1H), 8.42 (d, J=5.1 Hz, 1H), 7.35 (d, J=5.1 Hz, 1H), 3.94 (t, J=8.0 Hz, 2H), 3.85 (s, 3H), 3.54 (t, J=8.0 Hz, 2H), 3.06 (d, J=6.9 Hz, 2H), 0.97-0.87 (m, 1H), 0.49-0.43 (m, 2H), 0.22-0.15 (m, 2H); $^{13}$C NMR (75 MHz, DMSO-d$_6$) δ 165.8, 156.5, 153.8, 149.1, 138.4, 116.1, 111.4, 53.2, 48.2, 41.7, 41.5, 9.4, 3.6; MS (ES+) m/z 276.3 (M+1).

Preparation 17.2

Preparation of methyl 2-(2-oxo-3-(pyridin-2-ylmethyl)imidazolidin-1-yl)isonicotinate

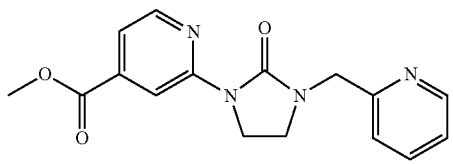 [SMILES: COC(=O)c1ccnc(N2CCN(Cc3ccccn3)C2=O)c1]

Following the procedure as described in Preparation 17, making variations as required to replace 1-(bromomethyl)-4-fluorobenzene with 2-(bromomethyl)pyridine hydrobromide to react with 2-(2-oxoimidazolidin-1-yl)isonicotinate, methyl 2-(2-oxo-3-(pyridin-2-ylmethyl)imidazolidin-1-yl)isonicotinate was obtained as a colorless solid in 66% yield: mp 100-102° C.; $^1$H NMR (300 MHz, CDCl$_3$) δ 8.88 (d, J=0.9 Hz, 1H), 8.55 (d, J=4.8 Hz, 1H), 8.36 (d, J=5.1 Hz, 1H), 7.70-7.64 (m, 1H), 7.46-7.44 (m, 1H), 7.34 (d, J=7.8 Hz, 1H), 7.22-7.18 (m, 1H), 4.62 (s, 2H), 4.07 (t, J=8.1 Hz, 2H), 3.90 (s, 3H), 3.54 (t, J=8.1 Hz, 2H); $^{13}$C NMR (75 MHz, CDCl$_3$) δ 165.9, 157.0, 156.6, 153.4, 149.3, 148.0, 138.7, 137.2, 122.7, 122.4, 116.7, 112.5, 52.6, 49.6, 41.9, 41.5; MS (ES+) m/z 312.9 (M+1).

Preparation 17.3

Preparation of methyl 2-(2-oxo-3-(pyridin-4-ylmethyl)imidazolidin-1-yl)isonicotinate

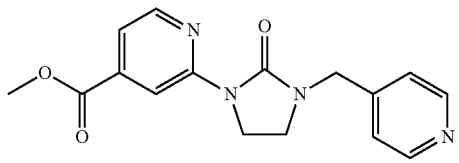 [SMILES: COC(=O)c1ccnc(N2CCN(Cc3ccncc3)C2=O)c1]

Following the procedure as described in Preparation 17, making variations as required to replace 1-(bromomethyl)-4-fluorobenzene with 4-(bromomethyl)pyridine hydrobromide to react with 2-(2-oxoimidazolidin-1-yl)isonicotinate, methyl 2-(2-oxo-3-(pyridin-4-ylmethyl)imidazolidin-1-yl)isonicotinate was obtained as a colorless solid in 43% yield: mp 111-113° C.; $^1$H NMR (300 MHz, DMSO-d$_6$) δ 8.73 (s, 1H), 8.51 (d, J=5.7 Hz, 2H), 8.45-8.44 (m, 1H), 7.40-7.38 (m, 1H), 7.30 (d, J=6.0 Hz, 2H), 4.44 (s, 2H), 3.99 (t, J=7.9 Hz, 2H), 3.86 (s, 3H), 3.42 (t, J=7.9 Hz, 2H); $^{13}$C NMR (75 MHz, DMSO-d$_6$) δ 165.7, 156.9, 153.7, 150.3, 149.1, 146.6, 138.5, 123.0, 116.4, 111.5, 53.2, 46.4, 41.7, 39.1; MS (ES+) m/z 312.9 (M+1).

Preparation 17.4

Preparation of methyl 2-(2-oxo-3-(pyridin-3-ylmethyl)imidazolidin-1-yl)isonicotinate

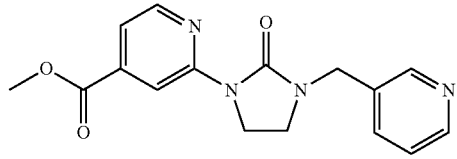 [SMILES: COC(=O)c1ccnc(N2CCN(Cc3cccnc3)C2=O)c1]

Following the procedure as described in Preparation 17, making variations as required to replace 1-(bromomethyl)-4-fluorobenzene with 3-(bromomethyl)pyridine hydrobromide to react with 2-(2-oxoimidazolidin-1-yl)isonicotinate, methyl 2-(2-oxo-3-(pyridin-3-ylmethyl)imidazolidin-1-yl)isonicotinate was obtained as a colorless solid in 47% yield: mp 165-167° C.; $^1$H NMR (300 MHz, CDCl$_3$) δ 8.86 (s, 1H), 8.56-8.54 (m, 2H), 8.36 (d, J=5.1 Hz, 1H), 7.69-7.66 (m, 1H), 7.46 (dd, J=5.4 Hz, 1.5 Hz, 1H), 7.30-7.26 (m, 1H), 4.50 (s, 2H), 4.05 (t, J=8.1 Hz, 2H), 3.92 (s, 3H), 3.39 (t, J=8.1 Hz, 2H); $^{13}$C NMR (75 MHz, CDCl$_3$) δ 165.8, 156.9, 153.2, 149.6, 149.4, 148.0, 138.8, 136.0, 132.1, 123.8, 116.9, 112.5, 52.6, 45.5, 41.3, 41.2; MS (ES+) m/z 312.9 (M+1).

Preparation 17.5

Preparation of methyl 2-(1-(cyclopropylmethyl)-5-oxo-1H-1,2,4-triazol-4(5H)-yl)isonicotinate

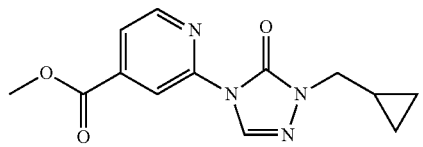 [SMILES: COC(=O)c1ccnc(-n2cnn(CC3CC3)c2=O)c1]

Following the procedure as described in Preparation 17, making variations as required to replace 1-(bromomethyl)-4-fluorobenzene with (bromomethyl)cyclopropane to react with methyl 2-(5-oxo-1H-1,2,4-triazol-4(5H)-yl)isonicotinate, methyl 2-(1-(cyclopropylmethyl)-5-oxo-1H-1,2,4-triazol-4(5H)-yl)isonicotinate was obtained as a colorless solid in 65% yield: MS (ES+) m/z 275.1 (M+1).

Preparation 17.6

Preparation of methyl 2-(1-(4-fluorobenzyl)-5-oxo-1H-1,2,4-triazol-4(5H)-yl)isonicotinate

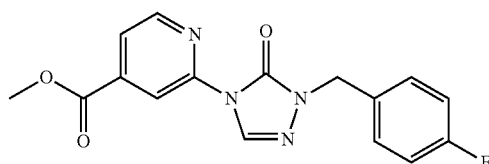

Following the procedure as described in Preparation 17, making variations as required to replace 2-(2-oxoimidazolidin-1-yl)isonicotinate with methyl 2-(5-oxo-1H-1,2,4-triazol-4(5H)-yl)isonicotinate to react with 1-(bromomethyl)-4-fluorobenzene, methyl 2-(1-(4-fluorobenzyl)-5-oxo-1H-1,2,4-triazol-4(5H)-yl)isonicotinate was obtained as a colorless solid in 65% yield: MS (ES+) m/z 328.9 (M+1).

Preparation 17.7

Preparation of methyl 2-(3-(3,4-difluorobenzyl)-2-oxoimidazolidin-1-yl)isonicotinate

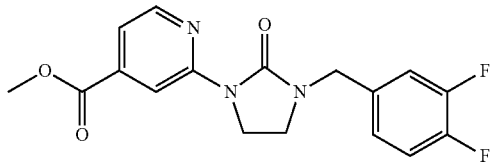 [SMILES: COC(=O)c1ccnc(N2CCN(Cc3ccc(F)c(F)c3)C2=O)c1]

Following the procedure as described in Preparation 17, making variations as required to replace 1-(bromomethyl)-4-fluorobenzene with 4-(bromomethyl)-1,2-difluorobenzene to react with 2-(2-oxoimidazolidin-1-yl)isonicotinate, methyl 2-(3-(3,4-difluorobenzyl)-2-oxoimidazolidin-1-yl)isonicotinate was obtained as a colorless solid in 66% yield: $^1$H NMR (300 MHz, CDCl$_3$) δ 8.86-8.85 (m, 1H), 8.37 (dd, J=5.1, 0.6 Hz, 1H), 7.47-7.45 (m, 1H), 7.16-7.01 (m, 3H), 4.43 (s, 2H), 4.05 (t, J=8.0 Hz, 2H), 3.92 (s, 3H), 3.38 (t, J=8.0 Hz, 2H); MS (ES+) m/z 348.0 (M+1).

Preparation 17.8

Preparation of methyl 2-(3-(2,4-difluorobenzyl)-2-oxoimidazolidin-1-yl)isonicotinate

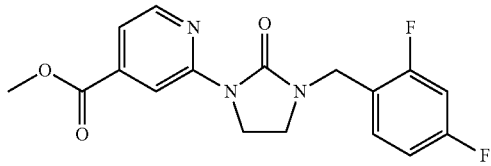 [SMILES: COC(=O)c1ccnc(N2CCN(Cc3ccc(F)cc3F)C2=O)c1]

Following the procedure as described in Preparation 17, making variations as required to replace 1-(bromomethyl)-4-fluorobenzene with 1-(bromomethyl)-2,4-difluorobenzene to react with 2-(2-oxoimidazolidin-1-yl)isonicotinate, methyl 2-(3-(2,4-difluorobenzyl)-2-oxoimidazolidin-1-yl)isonicotinate was obtained as a colorless solid in 64% yield: $^1$H NMR (300 MHz, CDCl$_3$) δ 8.85 (s, 1H), 8.36 (d, J=5.1 Hz, 1H), 7.46-7.31 (m, 2H), 6.89-6.79 (m, 2H), 4.51 (s, 2H), 4.04 (t, J=8.1 Hz, 2H), 3.92 (s, 3H), 3.44 (t, J=8.1 Hz, 2H); MS (ES+) m/z 347.9 (M+1).

Preparation 18

Preparation of 2-(3-(4-fluorobenzyl)-2-oxoimidazolidin-1-yl)isonicotinic acid

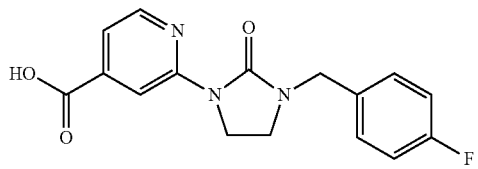 [SMILES: O=C(O)c1ccnc(N2CCN(Cc3ccc(F)cc3)C2=O)c1]

A solution of methyl 2-(3-(4-fluorobenzyl)-2-oxoimidazolidin-1-yl)isonicotinate (4.57 g, 13.90 mmol) and lithium hydroxide monohydrate (4.05 g, 96.52 mmol) in tetrahydrofuran (170 mL) and water (85 mL) was stirred for 19 hours. The organic solvent was removed in vacuo. The aqueous solution was acidified with 12 M hydrochloric acid solution until pH 3. The solid was filtered, washed with water (30 mL), hexanes (20 mL) and dried in vacuo to give 2-(3-(4-fluorobenzyl)-2-oxoimidazolidin-1-yl)isonicotinic acid as a colorless solid (4.15 g, 95%). $^1$H NMR (300 MHz, DMSO-d$_6$) δ 8.71 (s, 1H), 8.40 (d, J=5.1 Hz, 1H), 7.37-7.31 (m, 3H), 7.18-7.13 (m, 2H), 4.39 (s, 2H), 3.94 (t, J=8.1 Hz, 2H), 3.35 (t, J=8.1 Hz, 2H); MS (ES+) m/z 316.2 (M+1).

Example 1

Synthesis of 2-benzamido-N-(4-(trifluoromethyl)benzyl)isonicotinamide

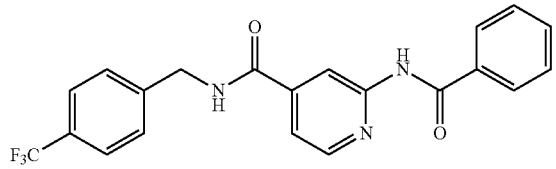 [SMILES: O=C(NCc1ccc(C(F)(F)F)cc1)c1ccnc(NC(=O)c2ccccc2)c1]

A solution of 2-benzamidoisonicotinic acid (0.18 g, 0.74 mmol) in thionyl chloride (10 mL) was refluxed for 30 minutes and concentrated in vacuo to dryness. The residue was dissolved in dichloromethane (25 mL) and added to a mixture of (4-(trifluoromethyl)phenyl)methanamine (0.13 g, 0.74 mmol) and triethylamine (0.31 mL, 2.23 mmol) in dichloromethane (20 mL). The reaction mixture was stirred at ambient temperature for 30 minutes, washed with saturated sodium bicarbonate solution (30 mL), water (30 mL) and brine (30 mL), then dried over anhydrous sodium sulfate, filtered and concentrated in vacuo. The residue was purified by column chromatography eluted with 30-45% ethyl acetate in hexanes to give 2-benzamido-N-(4-(trifluoromethyl)benzyl)-isonicotinamide as a colorless solid (0.02 g, 8%): mp 165-168° C. (dichloromethane/hexanes); $^1$H NMR (300 MHz, CDCl$_3$) δ 8.79 (br s, 2H), 8.66 (s, 1H), 7.89-7.86 (m, 2H), 7.59-7.44 (m, 8H), 7.05-7.03 (m, 1H), 4.69 (d, J=6.0 Hz, 2H); $^{13}$C NMR (75 MHz, CDCl$_3$) δ 166.0, 165.4, 152.1, 149.1, 143.7, 141.7, 133.6, 132.7, 129.0 (2 peaks), 128.1 (2 peaks), 127.2 (2 peaks), 125.8, 125.7, 118.7, 110.3, 43.7; MS (ES+) m/z 400.4 (M+1).

Example 1.1

Synthesis of
2-benzamido-N-(3,5-dichlorobenzyl)isonicotinamide

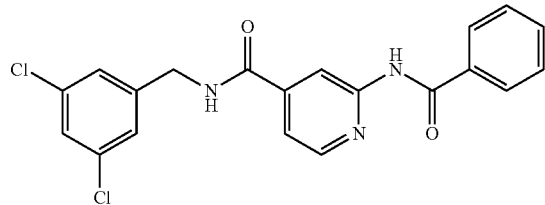 [SMILES: O=C(NCc1cc(Cl)cc(Cl)c1)c1ccnc(NC(=O)c2ccccc2)c1]

Following the procedure as described in Example 1, making variations as required to replace (4-(trifluoromethyl)phenyl)methanamine with (3,5-dichlorophenyl)-methanamine to react with 2-benzamidoisonicotinic acid, 2-benzamido-N-(3,5-dichlorobenzyl)isonicotinamide was obtained as a colorless solid in 41% yield: mp 248-251° C. (dichloromethane/hexanes); $^1$H NMR (300 MHz, DMSO-$d_6$) δ 11.01 (br s, 1H), 9.42 (br s, 1H), 8.63-8.54 (m, 2H), 8.06 (s, 2H), 7.60-7.39 (m, 7H), 4.53-4.51 (d, J=4.5 Hz, 2H).

Example 1.2

Synthesis of
2-benzamido-N-(4-methylbenzyl)isonicotinamide

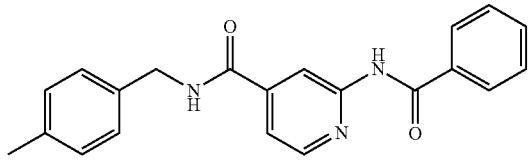 [SMILES: Cc1ccc(CNC(=O)c2ccnc(NC(=O)c3ccccc3)c2)cc1]

Following the procedure as described in Example 1, making variations as required to replace (4-(trifluoromethyl)phenyl)methanamine with p-tolylmethanamine to react with 2-benzamidoisonicotinic acid, 2-benzamido-N-(4-methylbenzyl)-isonicotinamide was obtained as a colorless solid in 35% yield: mp 135-138° C. (dichloromethane/hexanes); $^1$H NMR (300 MHz, DMSO-$d_6$) δ 11.02 (s, 1H), 9.33-9.30 (m, 1H), 8.60-8.51 (m, 2H), 8.06-8.03 (m, 2H), 7.63-7.50 (m, 4H), 6.25-7.03 (m, 4H), 4.45 (d, J=6.0 Hz, 2H), 2.28 (s, 3H); $^{13}$C NMR (75 MHz, DMSO-$d_6$) δ 166.0, 164.7, 152.8, 148.4, 143.6, 136.1, 135.9, 133.8, 131.9, 128.8, 128.3, 127.9, 127.3, 117.2, 112.7, 42.4, 20.6; MS (ES+) m/z 346.5 (M+1).

Example 1.3

Synthesis of 2-benzamido-N-[2-(2-chlorophenyl)ethyl]isonicotinamide

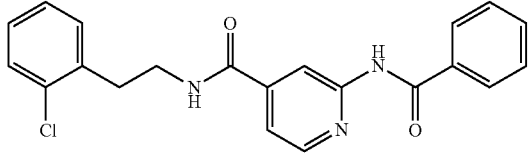 [SMILES: O=C(NCCc1ccccc1Cl)c1ccnc(NC(=O)c2ccccc2)c1]

Following the procedure as described in Example 1, making variations as required to replace (4-(trifluoromethyl)phenyl)methanamine with 2-(2-chlorophenyl)ethanamine to react with 2-benzamidoisonicotinic acid, 2-benzamido-N-[2-(2-chlorophenyl)ethyl]-isonicotinamide was obtained as a colorless solid in 27% yield: $^1$H NMR (300 MHz, DMSO-$d_6$) δ 10.91-10.82 (m, 1H), 8.91-8.85 (m, 1H), 8.56-8.44 (m, 2H), 8.06-7.98 (m, 2H), 7.63-7.17 (m, 8H), 3.55-3.48 (m, 2H), 3.03-2.92 (m, 2H); MS (ES+) m/z 380.5 (M+1), 382.3 (M+2).

Example 1.4

Synthesis of
2-benzamido-N-phenethylisonicotinamide

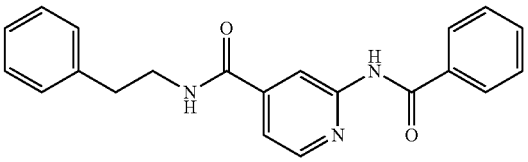 [SMILES: O=C(NCCc1ccccc1)c1ccnc(NC(=O)c2ccccc2)c1]

Following the procedure as described in Example 1, making variations as required to replace (4-(trifluoromethyl)phenyl)methanamine with 2-phenylethanamine to react with 2-benzamidoisonicotinic acid, 2-benzamido-N-phenethylisonicotinamide was obtained as a colorless solid in 67% yield: $^1$H NMR (300 MHz, DMSO-$d_6$) δ 10.97 (s, 1H), 8.90-8.86 (m, 1H), 8.55-8.50 (m, 2H), 8.06-8.03 (m, 2H), 7.64-7.47 (m, 4H), 7.34-7.18 (m, 5H), 3.54-3.48 (m, 2H), 2.87 (t, J=7.4 Hz, 2H); MS (ES+) m/z 346.5 (M+1).

Example 1.5

Synthesis of
2-benzamido-N-(3-phenylpropyl)isonicotinamide

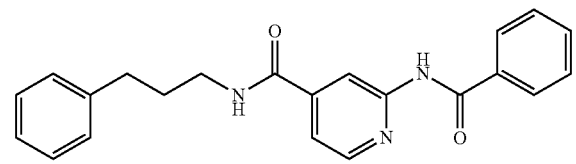 [SMILES: O=C(NCCCc1ccccc1)c1ccnc(NC(=O)c2ccccc2)c1]

Following the procedure as described in Example 1, making variations as required to replace (4-(trifluoromethyl)phenyl)methanamine with 3-phenylpropan-1-amine to react with 2-benzamidoisonicotinic acid, 2-benzamido-N-(3-phenylpropyl)-isonicotinamide was obtained as a colorless solid in 72% yield: $^1$H NMR (300 MHz, DMSO-$d_6$) δ 10.97 (s, 1H), 8.82-8.78 (m, 1H), 8.56-8.50 (m, 2H), 8.05-8.03 (m, 2H), 7.64-7.50 (m, 4H), 7.32-7.16 (m, 5H), 3.31-3.27 (m, 2H), 2.67-2.62 (m, 2H), 1.90-1.80 (m, 2H); MS (ES+) m/z 360.5 (M+1).

Example 1.6

Synthesis of 2-benzamido-N-[2-(2-fluorophenyl)ethyl]isonicotinamide

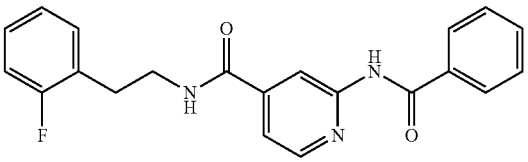 [SMILES: O=C(NCCc1ccccc1F)c1ccnc(NC(=O)c2ccccc2)c1]

Following the procedure as described in Example 1, making variations as required to replace (4-(trifluoromethyl)phenyl)methanamine with 2-(2-fluorophenyl)ethanamine to react with 2-benzamidoisonicotinic acid, 2-benzamido-N-[2-(2-fluorophenyl)ethyl]-isonicotinamide was obtained as a colorless 2H), 3.00 (t, J=7.0 Hz, 2H); MS (ES+) m/z 364.6 (M+1).

Example 1.7

Synthesis of 2-benzamido-N-[2-(3-methoxyphenyl)ethyl]isonicotinamide

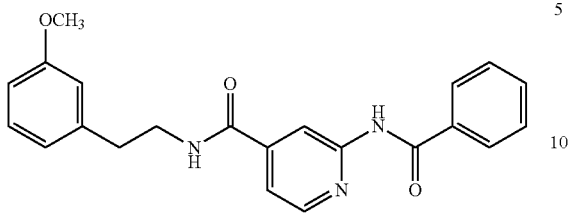

Following the procedure as described in Example 1, making variations as required to replace (4-(trifluoromethyl)phenyl)methanamine with 2-(3-methoxyphenyl)ethanamine to react with 2-benzamidoisonicotinic acid, 2-benzamido-N-[2-(3-methoxyphenyl)ethyl]isonicotinamide was obtained as a colorless solid in 45% yield: $^1$H NMR (300 MHz, DMSO-$d_6$) δ 10.98 (s, 1H), 8.88 (t, J=5.5 Hz, 1H), 8.57 (s, 1H), 8.52-8.49 (m, 1H), 8.07-8.04 (m, 2H), 7.63-7.48 (m, 4H), 7.24-7.17 (m, 1H), 6.84-6.76 (m, 3H), 3.73 (s, 3H), 3.55-3.48 (m, 2H), 2.85 (t, J=7.3 Hz, 2H); MS (ES+) m/z 376.5 (M+1).

Example 1.8

Synthesis of 2-benzamido-N-[2-(4-methoxyphenyl)ethyl]isonicotinamide

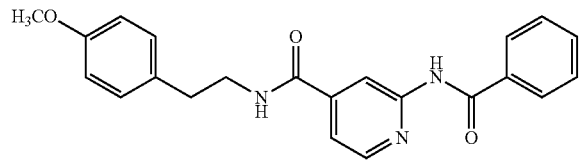 [SMILES: COc1ccc(CCNC(=O)c2ccnc(NC(=O)c3ccccc3)c2)cc1]

Following the procedure as described in Example 1, making variations as required to replace (4-(trifluoromethyl)phenyl)methanamine with 2-(4-methoxyphenyl)ethanamine to react with 2-benzamidoisonicotinic acid, 2-benzamido-N-[2-(4-methoxyphenyl)ethyl]isonicotinamide was obtained as a colorless solid in 48% yield: $^1$H NMR (300 MHz, CDCl$_3$) δ 8.79 (s, 1H), 7.91 (d, J=5.6 Hz, 2H), 7.62-7.43 (m, 4H), 7.19-7.15 (m, 4H), 6.90-6.87 (m, 2H), 6.45-6.43 (m, 1H), 3.79 (s, 3H), 3.71-3.65 (m, 2H), 2.89 (t, J=7.2 Hz, 2H); MS (ES+) m/z 376.5 (M+1).

Example 1.9

Synthesis of 2-benzamido-N-[2-(4-chlorophenyl)ethyl]isonicotinamide

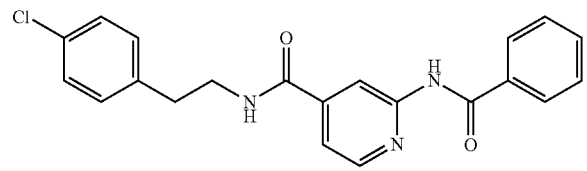 [SMILES: O=C(NCCc1ccc(Cl)cc1)c1ccnc(NC(=O)c2ccccc2)c1]

Following the procedure as described in Example 1, making variations as required to replace (4-(trifluoromethyl)phenyl)methanamine with 2-(4-chlorophenyl)ethanamine to react with 2-benzamidoisonicotinic acid, 2-benzamido-N-[2-(4-chlorophenyl)ethyl]isonicotinamide was obtained as a colorless solid in 52% yield: $^1$H NMR (300 MHz, DMSO-$d_6$) δ 10.97 (s, 1H), 8.82-8.05 (m, 1H), 8.54-8.49 (m, 2H), 8.06-8.04 (m, 2H), 7.63-7.46 (m, 4H), 7.38-7.27 (m, 4H), 3.51-3.49 (m, 2H), 2.86 (t, J=7.1 Hz, 2H); MS (ES+) m/z 380.4 (M+1), 382.3 (M+2).

Example 2

Synthesis of 2-benzamido-N-(3-chlorobenzyl)isonicotinamide

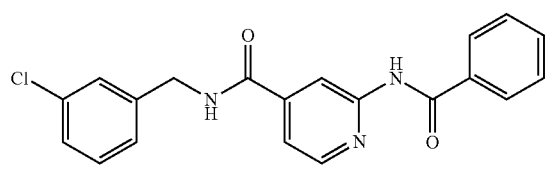 [SMILES: O=C(NCc1cccc(Cl)c1)c1ccnc(NC(=O)c2ccccc2)c1]

A solution of 2-benzamidoisonicotinic (isobutyl carbonic) anhydride (6.25 mL, 0.07 M N,N'-dimethyl formamide solution, 0.41 mmol) was added to a solution of 3-chlorobenzylamine (0.06 g, 0.41 mmol) in N,N'-dimethylformamide (0.8 mL) at ambient temperature. The resulting solution was stirred for 44 hours, diluted with ethyl acetate (20 mL), washed with saturated aqueous sodium bicarbonate solution (3×20 mL) and water (20 mL). The organic solution was dried over anhydrous sodium sulphate, filtered and concentrated in vacuo. The residue was purified by column chromatography eluted with 20-60% ethyl acetate in hexanes, triturated with diethyl ether to give 2-benzamido-N-(3-chlorobenzyl)isonicotinamide as a colorless solid (0.03 g, 22%): $^1$H NMR (300 MHz, DMSO-$d_6$) δ 11.00 (s, 1H), 9.40 (t, J=5.9 Hz, 1H), 8.61 (s, 1H), 8.53 (d, J=5.1 Hz, 1H), 8.07-8.02 (m, 2H), 7.65-7.48 (m, 4H), 7.43-7.27 (m, 4H), 4.50 (d, J=5.9 Hz, 2H); MS (ES+) m/z 366.4 (M+1), 368.5 (M+2).

Example 2.1

Synthesis of 2-benzamido-N-(4-chlorobenzyl)isonicotinamide

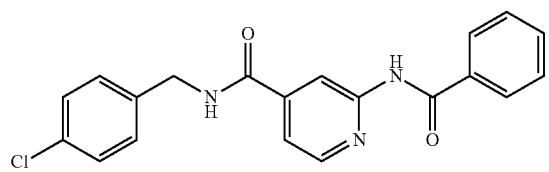 [SMILES: O=C(NCc1ccc(Cl)cc1)c1ccnc(NC(=O)c2ccccc2)c1]

Following the procedure as described in Example 2, making variations as required to replace 3-chlorobenzylamine with 4-chlorobenzylamine to react with 2-benzamidoisonicotinic (isobutyl carbonic) anhydride, 2-benzamido-N-(4-chlorobenzyl)isonicotinamide was obtained as a colorless solid in 26% yield: $^1$H NMR (300 MHz, DMSO-$d_6$) δ 10.99 (s, 1H), 9.38 (t, J=5.9 Hz, 1H), 8.61 (d, J=0.5 Hz, 1H), 8.53 (dd, J=5.1, 0.5 Hz, 1H), 8.07-8.02 (m, 2H), 7.65-7.48 (m, 4H), 7.44-7.34 (m, 4H), 4.48 (d, J=5.9 Hz, 2H); MS (ES+) m/z 366.4 (M+1), 368.5 (M+2).

Example 2.2

Synthesis of
2-benzamido-N-(4-methoxybenzyl)isonicotinamide

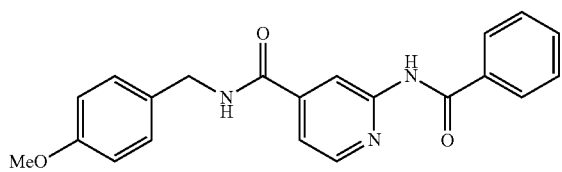 [SMILES: COc1ccc(CNC(=O)c2ccnc(NC(=O)c3ccccc3)c2)cc1]

Following the procedure as described in Example 2, making variations as required to replace 3-chlorobenzylamine with 4-methoxybenzylamine to react with 2-benzamidoisonicotinic (isobutylcarbonic) anhydride, 2-benzamido-N-(4-methoxybenzyl)isonicotinamide was obtained as a colorless solid in 26% yield: $^1$H NMR (300 MHz, DMSO-$d_6$) δ 11.08 (s, 1H), 9.34 (s, 1H), 8.58 (s, 1H), 8.52 (d, J=5.5 Hz, 1H), 8.05 (d, J=7.1 Hz, 2H), 7.65-7.49 (m, 4H), 7.27 (d, J=8.6 Hz, 2H), 6.90 (d, J=8.6 Hz, 2H), 4.42 (d, J=5.5 Hz, 2H), 3.73 (s, 3H); MS (ES+) m/z 362.5 (M+1).

Example 2.3

Synthesis of
2-benzamido-N-(3-fluorobenzyl)isonicotinamide

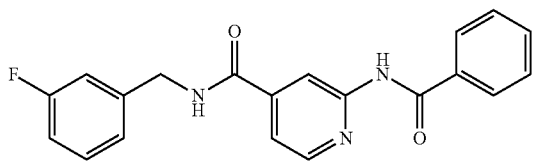 [SMILES: O=C(NCc1cccc(F)c1)c1ccnc(NC(=O)c2ccccc2)c1]

Following the procedure as described in Example 2, making variations as required to replace 3-chlorobenzylamine with 3-fluorobenzylamine to react with 2-benzamidoisonicotinic (isobutylcarbonic) anhydride, 2-benzamido-N-(3-fluorobenzyl)isonicotinamide was obtained as a colorless solid in 17% yield: $^1$H NMR (300 MHz, DMSO-$d_6$) δ 11.00 (s, 1H), 9.40 (t, J=6.0 Hz, 1H), 8.61 (s, 1H), 8.53 (dd, J=5.1, 0.6 Hz, 1H), 8.05 (d, J=7.1 Hz, 2H), 7.65-7.48 (m, 4H), 7.44-7.35 (m, 1H), 7.21-7.04 (m, 3H), 4.51 (d, J=6.0 Hz, 2H); MS (ES+) m/z 350.6 (M+1).

Example 2.4

Synthesis of
2-benzamido-N-(2-methoxybenzyl)isonicotinamide

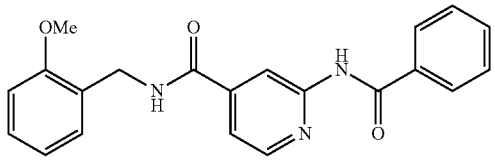 [SMILES: COc1ccccc1CNC(=O)c1ccnc(NC(=O)c2ccccc2)c1]

Following the procedure as described in Example 2, making variations as required to replace 3-chlorobenzylamine with 2-methoxybenzylamine to react with 2-benzamidoisonicotinic (isobutylcarbonic) anhydride, 2-benzamido-N-(2-methoxybenzyl)isonicotinamide was obtained as a colorless solid in 14% yield: $^1$H NMR (300 MHz, DMSO-$d_6$) δ 10.99 (s, 1H), 9.17 (t, J=5.8 Hz, 1H), 8.61 (s, 1H), 8.53 (d, J=5.1 Hz, 1H), 8.07-8.03 (m, 2H), 7.65-7.49 (m, 4H), 7.30-7.18 (m, 2H), 7.01 (d, J=7.8 Hz, 1H), 6.96-6.89 (m, 1H), 4.47 (d, J=5.8 Hz, 2H), 3.84 (s, 3H); MS (ES+) m/z 362.5 (M+1).

Example 2.5

Synthesis of
2-benzamido-N-(2-methylbenzyl)isonicotinamide

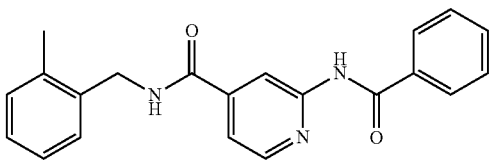 [SMILES: Cc1ccccc1CNC(=O)c1ccnc(NC(=O)c2ccccc2)c1]

Following the procedure as described in Example 2, making variations as required to replace 3-chlorobenzylamine with 2-methylbenzylamine to react with 2-benzamidoisonicotinic (isobutylcarbonic) anhydride, 2-benzamido-N-(2-methylbenzyl)isonicotinamide was obtained as a colorless solid in 14% yield: $^1$H NMR (300 MHz, DMSO-$d_6$) δ 10.98 (s, 1H), 9.22 (t, J=5.7 Hz, 1H), 8.60 (s, 1H), 8.52 (d, J=5.1 Hz, 1H), 8.07-8.02 (m, 2H), 7.65-7.49 (m, 4H), 7.29-7.15 (m, 4H), 4.48 (d, J=5.7 Hz, 2H), 2.34 (s, 3H); MS (ES+) m/z 346.6 (M+1).

Example 2.6

Synthesis of
2-benzamido-N-(3-methoxybenzyl)isonicotinamide

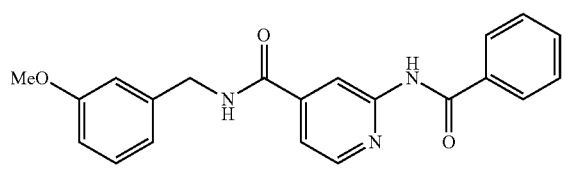 [SMILES: COc1cccc(CNC(=O)c2ccnc(NC(=O)c3ccccc3)c2)c1]

Following the procedure as described in Example 2, making variations as required to replace 3-chlorobenzylamine with 3-methoxylbenzylamine to react with 2-benzamidoisonicotinic (isobutylcarbonic) anhydride, 2-benzamido-N-(3-methoxybenzyl)isonicotinamide was obtained as a colorless solid in 30% yield: $^1$H NMR (300 MHz, DMSO-$d_6$) δ 10.99 (s, 1H), 9.34 (t, J=6.0 Hz, 1H), 8.60 (s, 1H), 8.52 (d, J=5.1 Hz, 1H), 8.08-8.01 (m, 2H), 7.65-7.48 (m, 4H), 7.30-7.22 (m, 1H), 6.94-6.88 (m, 2H), 6.86-6.80 (m, 1H), 4.47 (d, J=6.0 Hz, 2H), 3.74 (s, 3H); MS (ES+) m/z 362.5 (M+1).

Example 2.7

Synthesis of
2-benzamido-N-(2-fluorobenzyl)isonicotinamide

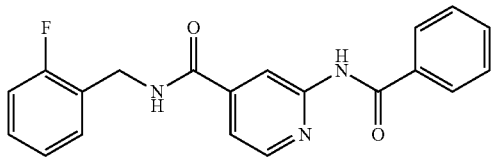 [SMILES: O=C(NCc1ccccc1F)c1ccnc(NC(=O)c2ccccc2)c1]

Following the procedure as described in Example 2, making variations as required to replace 3-chlorobenzylamine with 2-fluorobenzylamine to react with 2-benzamidoisonicotinic (isobutylcarbonic) anhydride, 2-benzamido-N-(2-fluorobenzyl)isonicotinamide was obtained as a colorless solid in 35% yield: $^1$H NMR (300 MHz, DMSO-$d_6$) δ 10.99 (s, 1H), 9.35 (t, J=5.6 Hz, 1H), 8.60 (s, 1H), 8.53 (d, J=5.1 Hz, 1H), 8.08-8.00 (m, 2H), 7.66-7.47 (m, 4H), 7.44-7.28 (m, 2H), 7.26-7.15 (m, 2H), 4.54 (d, J=5.6 Hz, 2H); MS (ES+) m/z 350.5 (M+1).

Example 2.8

Synthesis of 2-benzamido-N-(3-(trifluoromethyl)benzyl)isonicotinamide

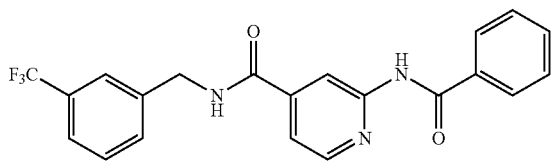 [SMILES: O=C(NCc1cccc(C(F)(F)F)c1)c1ccnc(NC(=O)c2ccccc2)c1]

Following the procedure as described in Example 2, making variations as required to replace 3-chlorobenzylamine with 3-trifluoromethylbenzylamine to react with 2-benzamidoisonicotinic (isobutylcarbonic) anhydride, 2-benzamido-N-(3-(trifluoromethyl)benzyl)isonicotinamide was obtained as a colorless solid in 18% yield: $^1$H NMR (300 MHz, DMSO-$d_6$) δ 11.01 (s, 1H), 9.46 (t, J=5.8 Hz, 1H), 8.61 (s, 1H), 8.54 (d, J=5.1 Hz, 1H), 8.08-8.01 (m, 2H), 7.73-7.49 (m, 8H), 4.59 (d, J=5.8 Hz, 2H); MS (ES+) m/z 400.5 (M+1).

Example 2.9

Synthesis of
2-benzamido-N-(2-chlorobenzyl)isonicotinamide

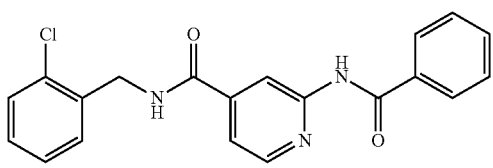 [SMILES: O=C(NCc1ccccc1Cl)c1ccnc(NC(=O)c2ccccc2)c1]

Following the procedure as described in Example 2, making variations as required to replace 3-chlorobenzylamine with 2-chlorobenzylamine to react with 2-benzamidoisonicotinic (isobutylcarbonic) anhydride, 2-benzamido-N-(2-chlorobenzyl)isonicotinamide was obtained as a colorless solid in 30% yield: $^1$H NMR (300 MHz, DMSO-$d_6$) δ 11.00 (s, 1H), 9.36 (t, J=5.6 Hz, 1H), 8.62 (s, 1H), 8.54 (d, J=5.1 Hz, 1H), 8.09-8.01 (m, 2H), 7.66-7.28 (m, 8H), 4.57 (d, J=5.6 Hz, 2H); MS (ES+) m/z 366.5 (M+1), 368.5 (M+2).

Example 2.10

Synthesis of
2-benzamido-N-(4-fluorobenzyl)isonicotinamide

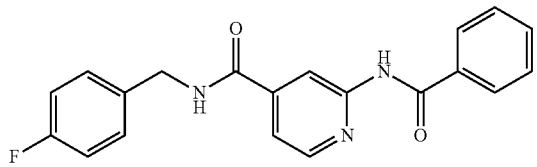 [SMILES: O=C(NCc1ccc(F)cc1)c1ccnc(NC(=O)c2ccccc2)c1]

Following the procedure as described in Example 2, making variations as required to replace 3-chlorobenzylamine with 4-fluorobenzylamine to react with 2-benzamidoisonicotinic (isobutylcarbonic) anhydride, 2-benzamido-N-(4-fluorobenzyl)isonicotinamide was obtained as a colorless solid in 18% yield: $^1$H NMR (300 MHz, DMSO-$d_6$) δ 10.99 (s, 1H), 9.37 (t, J=5.9 Hz, 1H), 8.59 (s, 1H), 8.52 (d, J=5.1 Hz, 1H), 8.06-8.01 (m, 2H), 7.68-7.47 (m, 4H), 7.41-7.35 (m, 2H), 7.22-7.13 (m, 2H), 4.47 (d, J=5.9 Hz, 2H); MS (ES+) m/z 350.5 (M+1).

Example 2.11

Synthesis of 2-benzamido-N-(benzo[d][1,3]dioxol-5-ylmethyl)isonicotinamide

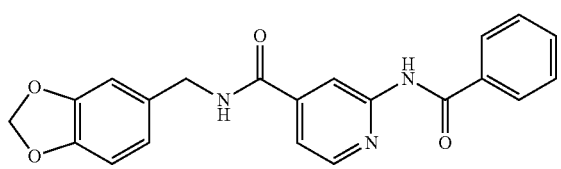 [SMILES: O=C(NCc1ccc2c(c1)OCO2)c1ccnc(NC(=O)c2ccccc2)c1]

Following the procedure as described in Example 2, making variations as required to replace 3-chlorobenzylamine with piperonylamine to react with 2-benzamido-isonicotinic (isobutylcarbonic) anhydride, 2-benzamido-N-(benzo[d][1,3]dioxol-5-ylmethyl)isonicotinamide was obtained as a colorless solid in 39% yield: $^1$H NMR (300 MHz, DMSO-$d_6$) δ 10.99 (s, 1H), 9.29 (t, J=5.6 Hz, 1H), 8.59 (s, 1H), 8.52 (d, J=5.1 Hz, 1H), 8.07-8.02 (m, 2H), 7.65-7.48 (m, 4H), 6.93-6.79 (m, 3H), 5.99 (d, J=1.7 Hz, 2H), 4.40 (d, J=5.6 Hz, 2H); MS (ES+) m/z 376.4 (M+1).

Example 2.12

Synthesis of 2-benzamido-N-(3,5-difluorobenzyl)isonicotinamide

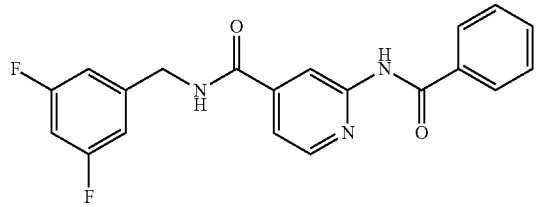 [SMILES: O=C(NCc1cc(F)cc(F)c1)c1ccnc(NC(=O)c2ccccc2)c1]

Following the procedure as described in Example 2, making variations as required to replace 3-chlorobenzylamine with 3,5-difluorobenzylamine to react with 2-benzamidoisonicotinic(isobutylcarbonic) anhydride, 2-benzamido-N-(3,5-difluorobenzyl)isonicotinamide was obtained as a colorless solid in 38% yield: $^1$H NMR (300 MHz, DMSO-$d_6$) δ 11.01 (s, 1H), 9.41 (t, J=5.9 Hz, 1H), 8.61 (s, 1H), 8.54 (dd, J=5.1, 0.7 Hz, 1H), 8.07-8.02 (m, 2H), 7.65-7.49 (m, 4H), 7.19-7.02 (m, 3H), 4.52 (d, J=5.9 Hz, 2H); MS (ES+) m/z 368.5 (M+1).

Example 3

Synthesis of N-(2-aminophenyl)-2-benzamidoisonicotinamide

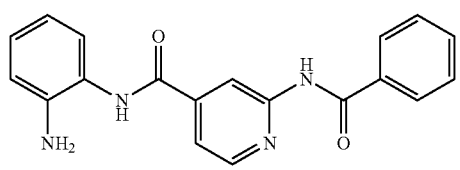 [SMILES: Nc1ccccc1NC(=O)c1ccnc(NC(=O)c2ccccc2)c1]

A solution of 2-benzamidoisonicotinic acid (0.50 g, 2.06 mmol), N,N-diisopropylethylamine (1.10 mL, 6.32 mmol), 1-hydroxybenzotriazole (0.418 g, 3.09 mmol) and 1-ethyl-3-(3-dimethylaminopropyl)carbodiimide hydrochloride (0.59 g, 3.09 mmol) in N,N-dimethylformamide (25 mL) was stirred for 15 minutes at ambient temperature and 1,2-phenylenediamine (0.22 g, 2.06 mmol) was added. The resulting solution was stirred for 20 hours at ambient temperature, diluted with ethyl acetate (75 mL), washed with saturated aqueous sodium bicarbonate solution (50 mL) and water (50 mL). The organic solution was dried over anhydrous sodium sulphate, filtered and concentrated in vacuo. The residue was triturated with diethyl ether to give N-(2-aminophenyl)-2-benzamidoisonicotinamide as an off-white solid (0.37 g, 53%): MS (ES+) m/z 333.5 (M+1).

Example 4

Synthesis of N-(4-(1H-benzo[d]imidazol-2-yl)pyridin-2-yl)benzamide

To a solution of N-(2-aminophenyl)-2-benzamidoisonicotinamide (0.18 g, 0.53 mmol) in toluene (10 mL) was added phosphorus oxychloride (0.14 mL, 1.57 mmol) at ambient temperature. The resulting solution was refluxed for 5 hours, cooled to ambient temperature and concentrated in vacuo. The residue was taken up in 1 M aqueous sodium hydroxide solution (50 mL) and extracted with dichloromethane (2×50 mL). The combined organic layers were dried over anhydrous sodium sulphate, filtered and concentrated in vacuo to dryness. The residue was purified by column chromatography eluting with 20-100% ethyl acetate in hexanes to give N-(4-(1H-benzo[d]imidazol-2-yl)pyridin-2-yl)benzamide as a pale yellow solid (0.02 g, 9%): mp 145-146° C.; $^1$H NMR (300 MHz, DMSO-$d_6$) δ 11.03 (s, 1H), 9.01 (s, 1H), 8.59 (d, J=5.2 Hz, 1H), 8.12-8.07 (m, 2H), 7.91 (dd, J=5.2, 1.4 Hz, 1H), 7.69 (dd, J=6.0, 3.2 Hz, 2H), 7.66-7.51 (m, 4H), 7.30 (dd, J=6.0, 3.2 Hz, 2H); MS (ES+) m/z 315.5 (M+1).

Example 5

Synthesis of 2-benzamido-N-benzylisonicotinamide

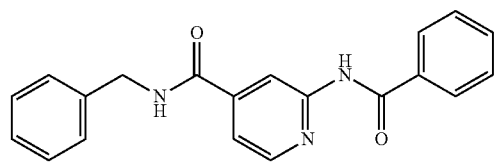 [SMILES: O=C(NCc1ccccc1)c1ccnc(NC(=O)c2ccccc2)c1]

To a solution of 2-amino-N-benzylisonicotinamide (0.23 g, 0.43 mmol), dimethylaminopyridine (0.01 g, 0.08 mmol) and N,N-diisopropylethylamine (0.3 mL, 1.7 mmol) in tetrahydrofuran (10 mL) at 0° C. was added benzoyl chloride (0.12 mL, 1.00 mmol). The resulting solution was warmed to ambient temperature and stirred for 18 hours, diluted with ethyl acetate (30 mL), washed with water (20 mL) and brine (20 mL). The organic solution was dried over anhydrous sulfate, filtered and concentrated in vacuo. The residue was purified by column chromatography to give 2-benzamido-N-benzylisonicotinamide (0.02 g, 15%): mp 174-176° C.; $^1$H NMR (300 MHz, CDCl$_3$) δ 8.86 (br s, 1H), 8.72 (s, 1H), 8.38 (d, J=5.1 Hz, 1H), 7.91-7.82 (m, 2H), 7.60-7.32 (m, 9H), 6.73 (br s, 1H), 4.64 (d, J=5.7 Hz, 2H); $^{13}$C NMR (75 MHz, CDCl$_3$) δ 165.9, 165.0, 151.9, 148.3, 144.4, 137.4, 133.5, 132.7, 129.0, 128.8, 128.0, 127.8, 127.2, 118.6, 110.5, 44.3; MS (ES+) m/z 332.5 (M+1).

Example 5.1

Synthesis of N-benzyl-2-(4-trifluoromethoxybenzoylamino)isonicotinamide

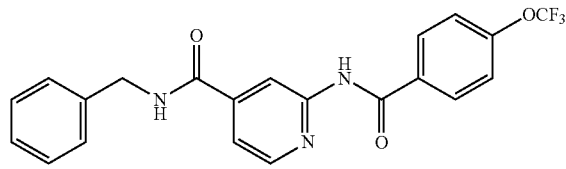 [SMILES: O=C(NCc1ccccc1)c1ccnc(NC(=O)c2ccc(OC(F)(F)F)cc2)c1]

Following the procedure as describe in preparation of Example 5, making variations as required to replace benzoyl chloride with 4-(trifluoromethoxy)benzoyl chloride to react with 2-amino-N-benzylisonicotinamide, N-benzyl-2-(4-trifluoromethoxybenzoylamino)isonicotinamide was obtained in 6% yield: mp 151-153° C.; $^1$H NMR (300 MHz, CDCl$_3$) δ 8.83 (br s, 1H), 8.68 (s, 1H), 8.35 (d, J=5.0 Hz, 1H), 7.93 (d, J=9.0 Hz, 2H), 7.58-7.54 (m, 1H), 7.38-7.28 (m, 7H), 6.75 (br s, 1H), 4.64 (d, J=5.7 Hz, 1H); $^{13}$C NMR (75 MHz, CDCl$_3$) δ 165.1, 164.5, 152.2, 151.8, 148.9, 144.2, 137.4, 132.0, 129.1, 128.8, 128.0, 127.8, 121.9, 120.8, 118.7, 118.5, 115.1, 110.5, 44.2; MS (ES+) m/z 416.4 (M+1).

Example 5.2

Synthesis of N-benzyl-2-(4-trifluoromethylbenzoylamino)isonicotinamide

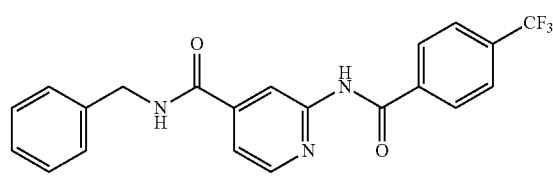 [SMILES: O=C(NCc1ccccc1)c1ccnc(NC(=O)c2ccc(C(F)(F)F)cc2)c1]

Following the procedure as describe in preparation of Example 5, variations as required to replace benzoyl chloride with 4-(trifluoromethy)benzoyl chloride to react with 2-amino-N-benzylisonicotinamide, N-benzyl-2-(4-trifluoromethylbenzoylamino)-isonicotinamide was obtained in 60% yield: mp 181-183° C.; $^1$H NMR (300 MHz, CDCl$_3$) δ 8.92 (br s, 1H), 8.61 (s, 1H), 8.32 (d, J=4.3 Hz, 1H), 7.97 (d, J=7.8 Hz, 2H), 7.73 (d, J=7.8 Hz, 2H), 7.53 (d, J=4.3 Hz, 1H), 7.38-7.15 (m, 5H), 6.98 (br s, 1H), 4.63 (d, J=5.7 Hz, 2H); MS (ES+) m/z 400.4 (M+1).

Example 5.3

Synthesis of N-benzyl-2-(3-phenylpropanamido)isonicotinamide

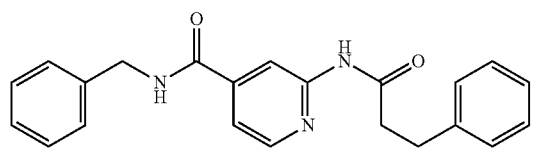 [SMILES: O=C(CCc1ccccc1)Nc1cc(C(=O)NCc2ccccc2)ccn1]

Following the procedure as describe in preparation of Example 5, making variations as required to replace benzoyl chloride with hydrocinnamoyl chloride, to react with 2-amino-N-benzylisonicotinamide, N-benzyl-2-(3-phenylpropanamido)-isonicotinamide was obtained in 42% yield: mp 177-179° C.; $^1$H NMR (300 MHz, CDCl$_3$) δ 10.63 (s, 1H), 9.26 (s, 1H), 8.46-8.36 (m, 2H), 7.54-7.14 (m, 11H), 4.43 (s, 2H), 2.86-2.68 (m, 4H); MS (ES+) m/z 360.6 (M+1).

Example 6

Synthesis of N-benzyl-2-(2-fluorobenzamido)isonicotinamide

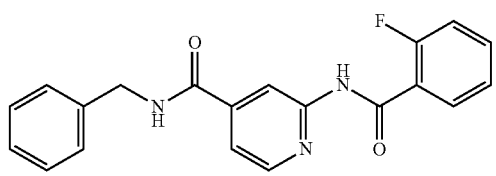 [SMILES: O=C(NCc1ccccc1)c1ccnc(NC(=O)c2ccccc2F)c1]

To a solution of 2-amino-N-benzylisonicotinamide (0.10 g, 0.44 mmol) and 4-dimethylaminopyridine (0.01 g, 0.08 mmol) in pyridine (3.0 mL) was added 2-fluorobenzoyl chloride (0.07 g, 0.44 mmol). The resulting solution was stirred at ambient temperature for 16 hours, diluted with dichloromethane (25 mL), washed with water (2×25 mL) and brine (10 mL). The organic solution was dried over anhydrous sodium sulphate, filtered and concentrated in vacuo. The residue was purified by column chromatography eluting with 45% ethyl acetate in hexanes to give N-benzyl-2-(2-fluorobenzamido)isonicotinamide as a colorless solid (0.07 g, 44%): mp 175-176° C. (hexanes/ethyl acetate); $^1$H NMR (300 MHz, CDCl$_3$) δ 9.21 (d, J=13.7 Hz, 1H), 8.64 (s, 1H), 8.46-8.42 (m, 1H), 8.12-8.06 (m, 1H), 7.64-7.48 (m, 2H), 7.35-7.16 (m, 7H), 6.68 (s, 1H), 4.65 (d, J=5.7 Hz, 2H); $^{13}$C NMR (CDCl$_3$, 75 MHz) δ 165.2, 162.1, 161.9, 158.8, 151.7, 148.8, 144.1, 137.5, 134.5, 134.4, 131.9, 128.8, 127.7, 125.1, 120.7, 118.8, 116.6, 116.3, 111.0, 44.2; MS (ES+) m/z 350.6 (M+1).

Example 6.1

Synthesis of N-benzyl-2-(3-fluorobenzamido)isonicotinamide

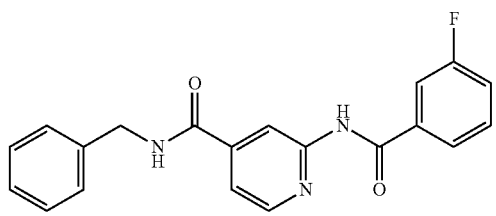 [SMILES: O=C(NCc1ccccc1)c1ccnc(NC(=O)c2cccc(F)c2)c1]

Following the procedure as describe in Example 6, making variations as required to replace 2-fluorobenzoyl chloride with 3-fluorobenzoyl chloride to react with 2-amino-N-benzylisonicotinamide, N-benzyl-2-(3-fluorobenzamido)isonicotinamide was obtained as a colorless solid in 44% yield: mp 140-143° C. (hexanes/ethyl acetate); $^1$H NMR (300 MHz, CDCl$_3$) δ 8.71 (s, 1H), 8.60 (s, 1H), 8.41-8.39 (m, 1H), 7.70-7.55 (m, 3H), 7.51-7.44 (m, 1H), 7.37-7.25 (m, 6H), 6.76-6.66 (m, 1H), 4.65 (d, J=5.8 Hz, 2H); MS (ES+) m/z 350.5 (M+1).

Example 6.2

Synthesis of N-benzyl-2-(cyclopentanecarboxamido) isonicotinamide

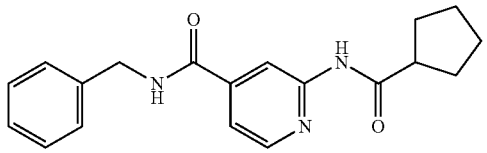 [SMILES: O=C(NCc1ccccc1)c1ccnc(NC(=O)C2CCCC2)c1]

Following the procedure as describe in Example 6, making variations as required to replace 2-fluorobenzoyl chloride with cyclopentanecarbonyl chloride to react with 2-amino-N-benzylisonicotinamide, N-benzyl-2-(cyclopentanecarboxamido)-isonicotinamide was obtained as a colorless solid in 88% yield: mp 55-57° C. (hexanes/ethyl acetate); $^1$H NMR (300 MHz, CDCl$_3$) δ 8.91 (s, 1H), 8.49 (s, 1H), 8.27 (d, J=5.1 Hz, 1H), 7.49 (d, J=5.1 Hz, 1H), 7.23-7.18 (m, 6H), 4.54 (d, J=5.7 Hz, 2H), 2.82-2.80 (m, 1H), 1.22-0.82 (m, 8H); $^{13}$C NMR (75 MHz, CDCl$_3$) δ 175.7, 165.3, 152.2, 148.2, 144.1, 137.5, 128.7, 128.4, 127.9, 127.6, 118.2, 110.9, 46.4, 44.1, 30.3, 25.9; MS (ES+) m/z 324.6 (M+1).

Example 6.3

Synthesis of N-benzyl-2-(thiophene-2-carboxamido) isonicotinamide

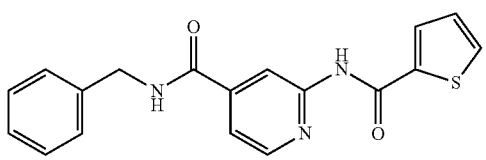 [SMILES: O=C(NCc1ccccc1)c1ccnc(NC(=O)c2cccs2)c1]

Following the procedure as describe in Example 6, making variations as required to replace 2-fluorobenzoyl chloride with thiophene-2-carbonyl chloride to react with 2-amino-N-benzylisonicotinamide, N-benzyl-2-(thiophene-2-carboxamido)isonicotinamide was obtained as a colorless solid in 73% yield: mp 160-162° C. (hexanes/ethyl acetate); $^1$H NMR (300 MHz, CDCl$_3$) δ 11.07 (s, 1H), 9.32 (t, J=5.7 Hz, 1H), 8.53-8.47 (m, 2H), 8.23-8.22 (m, 1H), 7.87 (d, J=5.0 Hz, 1H), 7.58-7.48 (m, 1H), 7.31-7.37 (m, 6H), 4.46 (d, J=5.9 Hz, 2H); MS (ES+) m/z 338.5 (M+1).

Example 6.4

Synthesis of N-benzyl-2-(3-methoxybenzamido)isonicotinamide

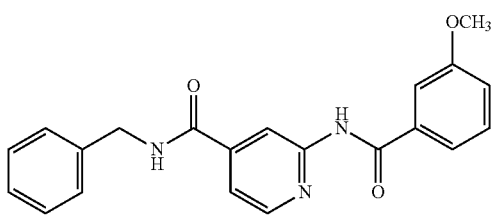 [SMILES: COc1cccc(C(=O)Nc2cc(C(=O)NCc3ccccc3)ccn2)c1]

Following the procedure as describe in Example 6, making variations as required to replace 2-fluorobenzoyl chloride with 3-methoxybenzoyl chloride to react with 2-amino-N-benzylisonicotinamide, N-benzyl-2-(3-methoxybenzamido) isonicotinamide was obtained as a colorless solid in 46% yield: mp 95-96° C. (hexanes/ethyl acetate); $^1$H NMR (300 MHz, CDCl$_3$) δ 8.88 (s, 1H), 8.64 (s, 1H), 8.36 (d, J=5.1 Hz, 1H), 7.56 (dd, J=5.1, 1.4 Hz, 1H), 7.43-7.25 (m, 8H), 7.11-7.07 (m, 1H), 6.80 (t, J=4.7 Hz, 1H), 4.63 (d, J=5.8 Hz, 2H), 3.84 (s, 3H); $^{13}$C NMR (75 MHz, CDCl$_3$) δ 165.8, 165.1, 160.0, 151.9, 148.6, 144.2, 137.4, 135.0, 129.9, 128.8, 128.0, 127.8, 118.9, 118.8, 118.6, 112.4, 110.5, 55.5, 44.2; MS (ES+) m/z 362.5 (M+1).

Example 6.5

Synthesis of N-benzyl-2-(4-methoxybenzamido)isonicotinamide

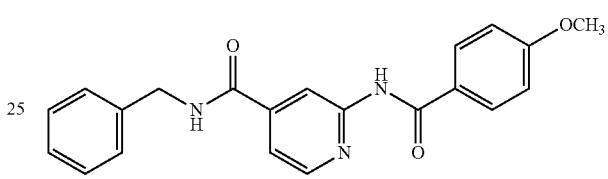

Following the procedure as describe in Example 6, making variations as required to replace 2-fluorobenzoyl chloride with 4-methoxybenzoyl chloride to react with 2-amino-N-benzylisonicotinamide, N-benzyl-2-(4-methoxybenzamido) isonicotinamide was obtained as a colorless solid in 28% yield: mp 165-166° C. (hexanes/ethyl acetate); $^1$H NMR (300 MHz, CDCl$_3$) δ 8.91 (s, 1H), 8.65 (s, 1H), 8.38 (d, J=5.2 Hz, 1H), 7.91-7.86 (m, 2H), 7.58 (dd, J=5.2, 1.5 Hz, 1H), 7.34-7.25 (m, 5H), 6.99-6.94 (m, 2H), 6.77 (s, 1H), 4.64 (d, J=5.8 Hz, 2H), 3.86 (s, 3H); MS (ES+) m/z 362.5 (M+1).

Example 6.6

Synthesis of N-benzyl-2-(2-methoxybenzamido)isonicotinamide

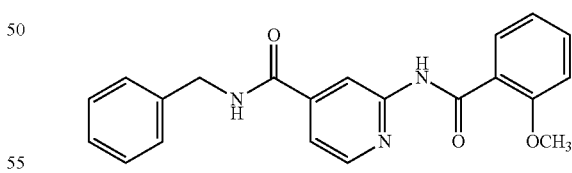

Following the procedure as describe in Example 6, making variations as required to replace 2-fluorobenzoyl chloride with 2-methoxybenzoyl chloride to react with 2-amino-N-benzylisonicotinamide, N-benzyl-2-(2-methoxybenzamido) isonicotinamide was obtained as a colorless solid in 76% yield: mp 205-207° C. (hexanes/ethyl acetate); $^1$H NMR (300 MHz, CDCl$_3$) δ 10.56 (s, 1H), 8.70 (s, 1H), 8.42 (d, J=5.1 Hz, 1H), 8.20 (dd, J=7.8, 1.8 Hz, 1H), 7.58-7.49 (m, 2H), 7.37-7.25 (m, 5H), 7.14-7.02 (m, 2H), 6.81 (s, 1H), 4.64 (d, J=5.8 Hz, 2H), 4.08 (s, 3H); MS (ES+) m/z 362.5 (M+1).

Example 6.7

Synthesis of 2-(1-naphthamido)-N-benzylisonicotinamide

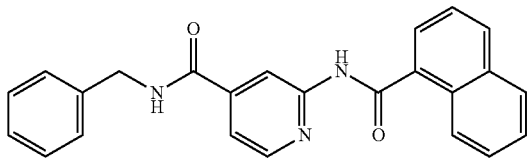 [SMILES: O=C(NCc1ccccc1)c1ccnc(NC(=O)c2cccc3ccccc23)c1]

Following the procedure as describe in Example 6, making variations as required to replace 2-fluorobenzoyl chloride with 1-naphthoyl chloride to react with 2-amino-N-benzylisonicotinamide, 2-(1-naphthamido)-N-benzylisonicotinamide was obtained as a colorless solid in 20% yield: mp 65-67° C. (hexanes/ethyl acetate); $^1$H NMR (300 MHz, CDCl$_3$) δ 9.70 (s, 1H), 8.72 (s, 1H), 8.29-8.22 (m, 1H), 7.95 (d, J=8.3 Hz, 1H), 7.97-7.84 (m, 1H), 7.76 (d, J=5.2 Hz, 1H), 7.69 (d, J=5.2 Hz, 1H), 7.50-7.31 (m, 7H), 7.28-7.24 (m, 2H), 7.08 (t, J=5.8 Hz, 1H), 4.59 (d, J=5.7 Hz, 2H); MS (ES+) m/z 382.5 (M+1).

Example 6.8

Synthesis of N-benzyl-2-(3,5-difluorobenzamido)isonicotinamide

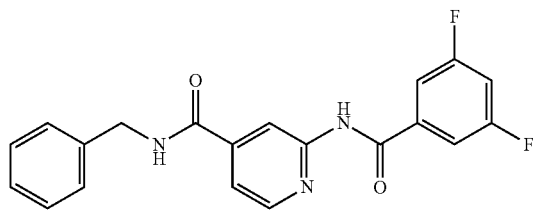 [SMILES: O=C(NCc1ccccc1)c1ccnc(NC(=O)c2cc(F)cc(F)c2)c1]

Following the procedure as describe in Example 6, making variations as required to replace 2-fluorobenzoyl chloride with 3,5-difluorobenzoyl chloride to react with 2-amino-N-benzylisonicotinamide, N-benzyl-2-(3,5-difluorobenzamido)isonicotinamide was obtained as a colorless solid in 68% yield: mp 185-187° C. (hexanes/ethyl acetate); $^1$H NMR (300 MHz, CDCl$_3$) δ 11.16 (s, 1H), 9.35 (t, J=6.0 Hz, 1H), 8.54-8.50 (m, 2H), 7.75-7.71 (m, 2H), 7.58-7.47 (m, 2H), 7.31-7.21 (m, 5H), 4.46 (d, J=5.9 Hz, 2H); MS (ES+) m/z 368.5 (M+1).

Example 6.9

Synthesis of N-benzyl-2-(2-chloro-5-fluorobenzamido)isonicotinamide

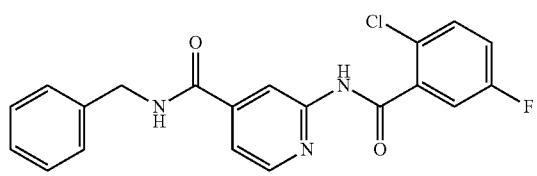 [SMILES: O=C(NCc1ccccc1)c1ccnc(NC(=O)c2cc(F)ccc2Cl)c1]

Following the procedure as describe in Example 6, making variations as required to replace 2-fluorobenzoyl chloride with 2-chloro-5-fluorobenzoyl chloride to react with 2-amino-N-benzylisonicotinamide, N-benzyl-2-(2-chloro-5-fluorobenzamido)-isonicotinamide was obtained as a colorless solid in 57% yield: mp 180-181° C. (hexanes/ethyl acetate); 1H NMR (300 MHz, CDCl3) (9.15 (d, J=13.8 Hz, 1H), 8.60 (s, 1H), 8.44 (d, J=5.0 Hz, 1H), 8.07 (dd, J=6.6, 2.8 Hz, 1H), 7.58 (d, J=4.2 Hz, 1H), 7.52-7.46 (m, 1H), 7.36-7.12 (m, 6H), 6.67 (s, 1H), 4.65 (d, J=5.7 Hz, 2H); MS (ES+) m/z 384.5 (M+1).

Example 6.10

Synthesis of N-benzyl-2-(4-cyanobenzamido)isonicotinamide

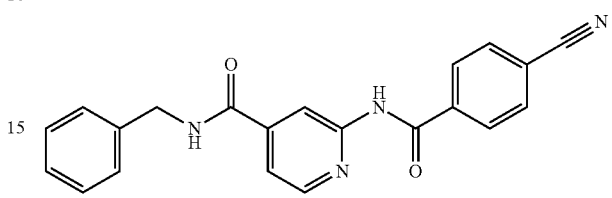

Following the procedure as describe in Example 6, making variations as required to replace 2-fluorobenzoyl chloride with 4-cyanobenzoyl chloride to react with 2-amino-N-benzylisonicotinamide, N-benzyl-2-(4-cyanobenzamido)isonicotinamide was obtained as a colorless solid in 35% yield: mp 180-181° C. (hexanes/ethyl acetate); $^1$H NMR (300 MHz, CDCl$_3$) δ 8.97 (s, 1H), 8.63 (s, 1H), 8.41 (t, J=5.0 Hz, 1H), 8.03-8.00 (m, 2H), 7.82-7.79 (m, 2H), 7.60 (dd, J=5.1, 1.2 Hz, 1H), 7.36-7.29 (m, 5H), 6.69 (m, 1H), 4.65 (d, J=5.7 Hz, 2H); MS (ES+) m/z 357.5 (M+1).

Example 6.11

Synthesis of N-benzyl-2-(4-(dimethylamino)benzamido)isonicotinamide

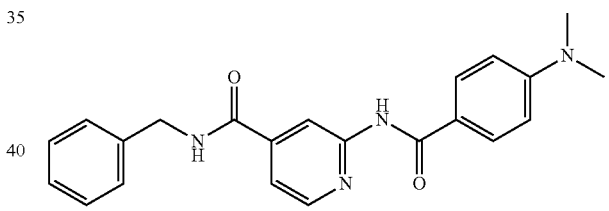

Following the procedure as describe in Example 6, making variations as required to replace 2-fluorobenzoyl chloride with 4-(dimethylamino)benzoyl chloride to react with 2-amino-N-benzylisonicotinamide, N-benzyl-2-(4-(dimethylamino)benzamido)-isonicotinamide was obtained as a colorless solid in 7% yield: mp 160-165° C. (hexanes/ethyl acetate); $^1$H NMR (300 MHz, DMSO-d$_6$) δ 10.49 (s, 1H), 9.28 (t, J=5.9 Hz, 1H), 8.54 (s, 1H), 8.44 (d, J=5.1 Hz, 1H), 7.93 (d, J=9.0 Hz, 2H), 7.46 (dd, J=5.1, 1.4 Hz, 1H), 7.36-7.16 (m, 5H), 6.70 (d, J=9.1 Hz, 2H), 4.43 (d, J=5.9 Hz, 2H), 2.96 (s, 6H); MS (ES+) m/z 375.5 (M+1).

Example 6.12

Synthesis of N-benzyl-2-(2-cyclopropylacetamido)isonicotinamide

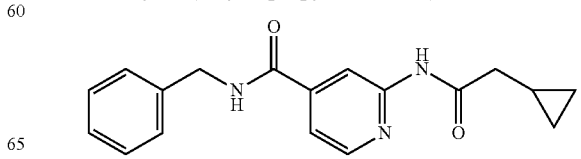

Following the procedure as describe in Example 6, making variations as required to replace 2-fluorobenzoyl chloride with 2-cyclopropylacetyl chloride to react with 2-amino-N-benzylisonicotinamide, N-benzyl-2-(2-cyclopropylacetamido)isonicotinamide was obtained as a colorless solid in 57% yield: $^1$H NMR (300 MHz, CDCl$_3$) δ 8.59 (s, 1H), 8.48 (s, 1H), 8.34 (d, J=5.1 Hz, 1H), 7.53 (dd, J=5.1, 1.4 Hz, 1H), 7.31-7.24 (m, 5H), 6.87 (br s, 1H), 4.60 (d, J=5.8 Hz, 2H), 2.31 (d, J=7.2 Hz, 2H), 1.08-0.99 (m, 1H), 0.70-0.62 (m, 2H), 0.25 (q, J=4.9 Hz, 2H); MS (ES+) m/z 310.6 (M+1).

Example 6.13

Synthesis of N-benzyl-2-(3-(methylsulfonyl)benzamido)isonicotinamide

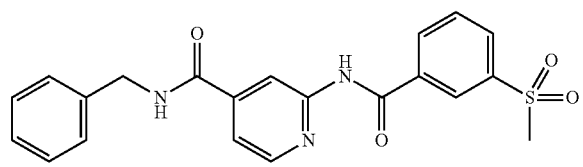 [SMILES: CS(=O)(=O)c1cccc(C(=O)Nc2cc(C(=O)NCc3ccccc3)ccn2)c1]

Following the procedure as describe in Example 6, making variations as required to replace 2-fluorobenzoyl chloride with 3-(methylsulfonyl)benzoyl chloride to react with 2-amino-N-benzylisonicotinamide, N-benzyl-2-(3-(methylsulfonyl)benzamido)-isonicotinamide was obtained as a colorless solid in 36% yield: mp 170-171° C. (hexanes/ethyl acetate); $^1$H NMR (300 MHz, DMSO-d$_6$) δ 11.33 (s, 1H), 9.34 (t, J=5.9 Hz, 1H), 8.58 (s, 1H), 8.52-8.50 (m, 2H), 8.30-8.27 (m, 1H), 8.11-8.08 (m, 1H), 7.80-7.75 (m, 1H), 7.56 (dd, J=5.2, 1.5 Hz, 1H), 7.34-7.19 (m, 5H), 4.47 (d, J=5.9 Hz, 2H), 3.26 (s, 3H); MS (ES+) m/z 410.5 (M+1).

Example 6.14

Synthesis of N-benzyl-2-(4-fluorobenzamido)isonicotinamide

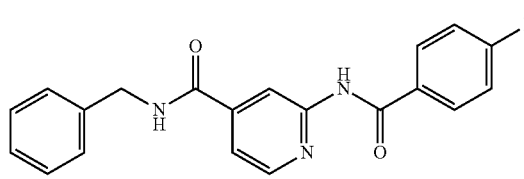

Following the procedure as describe in Example 6, making variations as required to replace 2-fluorobenzoyl chloride with 4-fluorobenzoyl chloride to react with 2-amino-N-benzylisonicotinamide, N-benzyl-2-(4-fluorobenzamido)isonicotinamide was obtained as a colorless solid in 27% yield: mp 170-171° C. (hexanes/ethyl acetate); $^1$H NMR (300 MHz, CDCl$_3$) δ 8.70 (s, 1H), 8.70 (s, 1H), 8.40 (d, J=5.1 Hz, 1H), 7.95-7.88 (m, 2H), 7.57 (dd, J=5.7, 1.5 Hz, 1H), 7.37-7.26 (m, 5H), 7.20-7.14 (m, 2H), 6.78-6.65 (m, 1H), 4.64 (d, J=5.8 Hz, 2H); MS (ES+) m/z 350.5 (M+1).

Example 6.15

Synthesis of N-benzyl-2-(3-(trifluoromethyl)benzamido)isonicotinamide

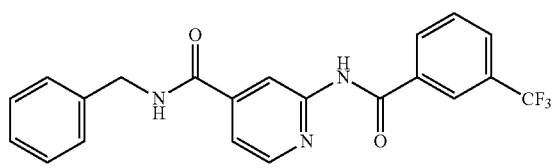 [SMILES: O=C(NCc1ccccc1)c1ccnc(NC(=O)c2cccc(C(F)(F)F)c2)c1]

Following the procedure as describe in Example 6, making non-critical variations as required to replace 2-fluorobenzoyl chloride with 3-(trifluoromethyl)benzoyl chloride to react with 2-amino-N-benzylisonicotinamide, N-benzyl-2-(3-(trifluoromethyl)benzamido)-isonicotinamide was obtained as a colorless solid in 80% yield: mp 126-128° C.; $^1$H NMR (300 MHz, CDCl$_3$) δ 10.36 (s, 1H), 8.82 (s, 1H), 8.41-8.14 (m, 4H), 7.95-7.27 (m, 7H), 7.03 (s, 1H), 4.57 (d, J=5.1 Hz, 2H); MS (ES+) m/z 400.5 (M+1).

Example 6.16

Synthesis of N-benzyl-2-(3-(trifluoromethyl)benzamido)isonicotinamide

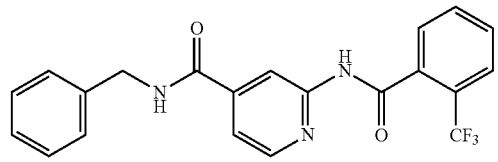 [SMILES: O=C(NCc1ccccc1)c1ccnc(NC(=O)c2ccccc2C(F)(F)F)c1]

Following the procedure as describe in Example 6, making variations as required to replace 2-fluorobenzoyl chloride with 2-(trifluoromethyl)benzoyl chloride to react with 2-amino-N-benzylisonicotinamide, N-benzyl-2-(3-(trifluoromethyl)benzamido)-isonicotinamide was obtained as a colorless solid in 73% yield: mp 87-88° C.; $^1$H NMR (300 MHz, CDCl$_3$) δ 10.09 (s, 1H), 8.58 (s, 1H), 7.82-6.95 (m, 12H), 4.57 (d, J=5.1 Hz, 2H); MS (ES+) m/z 400.5 (M+1).

Example 6.17

Synthesis of 2-benzamido-N-benzyl-6-methoxyisonicotinamide

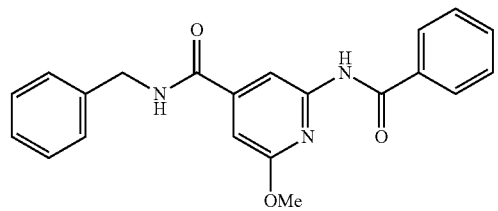 [SMILES: COc1cc(C(=O)NCc2ccccc2)cc(NC(=O)c2ccccc2)n1]

Following the procedure as describe in Example 6, making variations as required to replace 2-fluorobenzoyl chloride with benzoyl chloride to react with 2-amino-N-benzyl-6- methoxyisonicotinamide, 2-benzamido-N-benzyl-6-methoxyisonicotinamide was obtained as a colorless solid in 14% yield: mp 132-133° C.; $^1$H NMR (300 MHz, CDCl$_3$) 8.43 (s, 1H), 8.15 (s, 1H), 7.84 (d, J=7.5 Hz, 2H), 7.57-7.43 (m, 3H), 7.34-7.23 (m, 5H), 6.98 (s, 1H), 6.87 (s, 1H), 4.57 (d, J=5.1 Hz, 2H), 3.86 (s, 3H); $^{13}$C NMR (300 MHz, CDCl$_3$) δ 165.6, 165.3, 163.6, 149.8, 147.0, 137.6, 133.8, 132.4, 128.9, 128.7, 127.9, 127.6, 127.1, 105.2, 102.4, 54.0, 44.1; MS (ES+) m/z 362.5 (M+1).

Example 7

Synthesis of 2-benzamido-N-benzylisonicotinamide-1-N-oxide

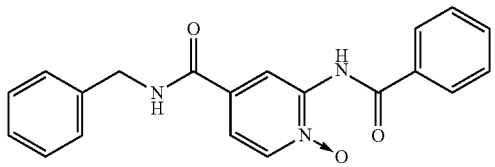 [SMILES: O=C(NCc1ccccc1)c1cc[n+]([O-])c(NC(=O)c2ccccc2)c1]

To a solution of 2-benzamido-N-benzylisonicotinamide (0.15 g, 0.43 mmol) in chloroform (20 mL) was added 3-chloroperoxybenzoic acid (0.12 g, 0.53 mmol). The resulting solution was stirred at ambient temperature for 18 hours, diluted with ethyl acetate (30 mL), washed with 10% sodium thiosulfate solution (20 mL), saturated sodium bicarbonate solution (20 mL), water (20 mL) and brine (20 mL). The organic solution was dried over anhydrous sulphate, filtered and concentrated in vacuo. The residue was purified by column chromatography to give 2-benzamido-N-benzylisonicotinamide-1-N-oxide as a colorless solid (0.14 g, 90%): mp 198-201° C.; $^1$H NMR (300 MHz, CDCl$_3$) δ 10.79 (s, 1H), 8.88 (d, J=2.4 Hz, 1H), 8.30 (d, J=6.9 Hz, 1H), 7.98-7.85 (m, 2H), 7.63-7.28 (m, 9H), 6.89 (br s, 1H), 4.63 (d, J=5.7 Hz, 2H); MS (ES+) m/z 348.5 (M+1).

Example 8

Synthesis of 2-benzamido-N-benzyl-6-hydroxyisonicotinamide

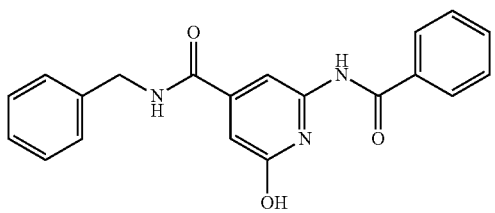 [SMILES: O=C(NCc1ccccc1)c1cc(O)nc(NC(=O)c2ccccc2)c1]

To a solution of 2-benzamido-N-benzyl-6-methoxyisonicotinamide (0.18 g, 0.50 mmol) and sodium iodide (0.45 g, 3.00 mmol) in acetonitrile (10 mL) was added chlorotrimethylsilane (0.39 mL, 3.00 mmol) and water (0.1 mL) at 0° C. The resulting solution was stirred at ambient temperature for 20 hours, quenched with methanol (10 mL), stirred for 10 minutes and concentrated in vacuo. The residue was washed with saturated sodium bicarbonate solution (5 mL) and water (5 mL). The organic solution was dried over anhydrous sodium sulphate, filtered and concentrated in vacuo to a minimum volume and triturated with ethyl acetate. The solid was filtered and dried in vacuo to give 2-benzamido-N-benzyl-6-hydroxyisonicotinamide as a colorless solid (0.04 g, 20%): mp 257° C. (dec); $^1$H NMR (300 MHz, DMSO-d$_6$) δ 11.07 (br s, 1H), 9.20 (br s, 1H), 8.46-6.59 (m, 12H), 4.37 (br s, 2H); MS (ES+) m/z 348.5 (M+1).

Example 9

Synthesis of N-(4-(4-methyl-4, ihydro-1H-imidazol-2-yl)pyridin-2-yl)benzamide

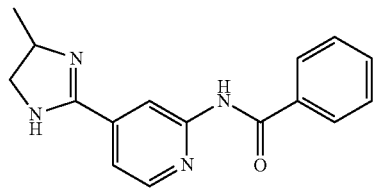

To a solution of 2-benzamidoisonicotinic acid (0.50 g, 2.06 mmol) and 1,2-diaminopropane (0.35 mL, 4.12 mmol) in 1,4-dioxane (20 mL) was added phosphorus oxychloride (0.94 mL, 10.30 mmol) dropwise at ambient temperature under nitrogen atmosphere. The resulting solution was refluxed for 15 hours, cooled to ambient temperature and concentrated in vacuo to dryness. The residue was diluted with saturated aqueous sodium bicarbonate solution (50 mL), extracted with dichloromethane (4×50 mL), dried over anhydrous sodium sulphate, filtered and concentrated in vacuo. The residue was purified by column chromatography eluting with ethyl acetate followed by 9:1:0.1 ratio of ethyl acetate, methanol and triethyl amine to give N-(4-(4-methyl-4,5-dihydro-1H-imidazol-2-yl)pyridin-2-yl)benzamide as a pale yellow foam (0.17 g, 29%): MS (ES+) m/z 281.5 (M+1).

Example 9.1

Synthesis of N-(4-(4-propyl-4,5-dihydro-1H-imidazol-2-yl)pyridin-2-yl)benzamide

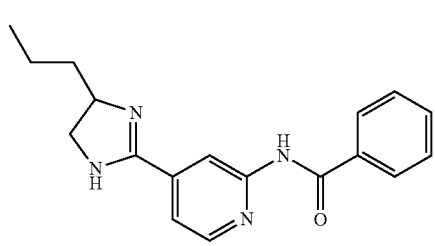 [SMILES: CCCC1CNC(c2ccnc(NC(=O)c3ccccc3)c2)=N1]

Following the procedure as described in EXAMPLE 9, making variations as required to replace 1,2-diaminopropane with 1,2-diaminopentane to react with 2-benzamidoisonicotinic acid, N-(4-(4-propyl-4,5-dihydro-1H-imidazol-2-yl)pyridin-2-yl)benzamide was obtained in 20% yield: MS (ES+) m/z 309.4 (M+1).

Example 9.2

Synthesis of N-(4-(4-benzyl-4,5-dihydro-1H-imidazol-2-yl)pyridin-2-yl)benzamide

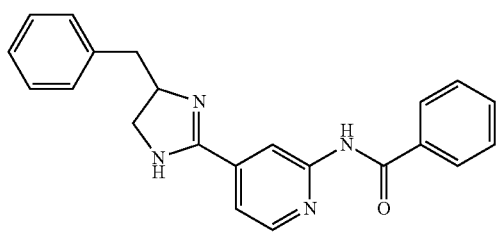 [SMILES: O=C(Nc1cc(C2=NC(Cc3ccccc3)CN2)ccn1)c1ccccc1]

Following the procedure as described in Example 9, making variations as required to replace 1,2-diaminopropane with (S)-3-phenylpropane-1,2-diamine to react with 2-benzamidoisonicotinic acid, N-(4-(4-benzyl-4,5-dihydro-1H-imidazol-2-yl)pyridin-2-yl)benzamide was obtained in 34% yield: MS (ES+) m/z 357.3 (M+1).

Example 9.3

Synthesis of N-(4-(4-isobutyl-4,5-dihydro-1H-imidazol-2-yl)pyridin-2-yl)benzamide

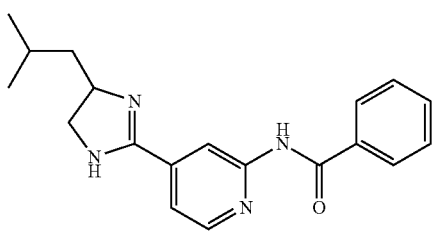

Following the procedure as described in Example 9, making variations as required to replace 1,2-diaminopropane with (S)-4-methylpentane-1,2-diamine to react with 2-benzamidoisonicotinic acid, N-(4-(4-isobutyl-4,5-dihydro-1H-imidazol-2-yl)pyridin-2-yl)benzamide was obtained in 23% yield: MS (ES+) m/z 323.2 (M+1).

Example 9.4

Synthesis of N-(4-(4-(3,5-difluorobenzyl)-4,5-dihydro-1H-imidazol-2-yl)pyridin-2-yl)benzamide

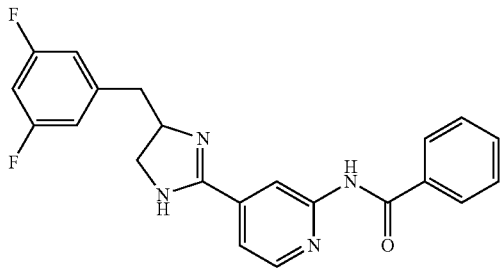 [SMILES: O=C(Nc1cc(C2=NC(Cc3cc(F)cc(F)c3)CN2)ccn1)c1ccccc1]

Following the procedure as described in Example 9, making variations as required to replace 1,2-diaminopropane with 3-(3,5-difluorophenyl)propane-1,2-diamine to react with 2-benzamidoisonicotinic acid, N-(4-(4-(3,5-difluorobenzyl)-4,5-dihydro-1H-imidazol-2-yl)pyridin-2-yl)benzamide was obtained in 24% yield: MS (ES+) m/z 393.2 (M+1).

Example 9.5

Synthesis of N-(4-(4-phenyl-4,5-dihydro-1H-imidazol-2-yl)pyridin-2-yl)benzamide

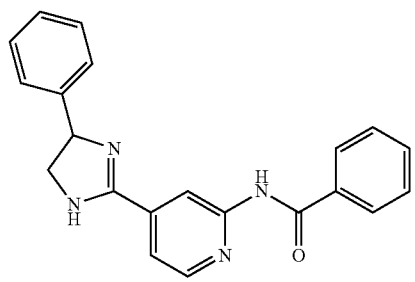 [SMILES: O=C(Nc1cc(C2=NC(c3ccccc3)CN2)ccn1)c1ccccc1]

Following the procedure as described in Example 9, making variations as required to replace 1,2-diaminopropane with 1-phenylethane-1,2-diamine to react with 2-benzamidoisonicotinic acid, N-(4-(4-phenyl-4,5-dihydro-1H-imidazol-2-yl)pyridin-2-yl)benzamide was obtained in 17% yield: MS (ES+) m/z 343.3 (M+1).

Example 10

Synthesis of N-(4-(4-methyl-1H-imidazol-2-yl)pyridin-2-yl)benzamide

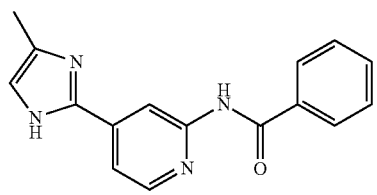 [SMILES: Cc1c[nH]c(-c2ccnc(NC(=O)c3ccccc3)c2)n1]

To a solution of oxalyl chloride (0.06 mL, 0.72 mmol) in anhydrous dichloromethane (1.0 mL) was added anhydrous dimethyl sulfoxide (0.09 mL, 1.20 mmol) dropwise at −78° C. under nitrogen atmosphere. The resulting solution was stirred for 10 minutes, followed by dropwise addition of a solution of N-(4-(4-methyl-4,5-dihydro-1H-imidazol-2-yl) pyridin-2-yl)benzamide (0.17 g, 0.60 mmol) in anhydrous dichloromethane (1.5 mL). The reaction mixture was stirred for 40 minutes, followed by the addition of anhydrous triethyl amine (0.33 mL, 2.38 mmol), warmed to ambient temperature during 3 hours and partitioned between water (15 mL) and dichloromethane (25 mL). The aqueous layer was extracted with dichloromethane (2×25 mL). The organic layer was dried over sodium sulphate, filtered and concentrated in vacuo to dryness. The residue was purified by column chromatography eluting with ethyl acetate followed by methanol in ethyl acetate (1:25 ratio) to give N-(4-(4-methyl-1H-imidazol-2-yl)pyridin-2-yl)benzamide as a colorless solid (0.05 g, 38%): mp 133-135° C.; $^1$H NMR (300 MHz, DMSO-d$_6$) δ 12.70 (s, 1H), 10.81 (s, 1H), 8.69 (s, 1H), 8.40 (d, J=5.3 Hz, 1H), 8.08-8.03 (m, 2H), 7.64-7.49 (m, 4H), 6.95 (br s, 1H), 2.24 (s, 3H); $^{13}$C NMR (75 MHz, CD$_3$OD) δ 168.5, 154.1, 149.8, 144.5, 140.8, 135.6, 133.4, 129.8, 128.8, 116.9, 111.4, 11.6; MS (ES+) m/z 279.4 (M+1).

Example 10.1

Synthesis of N-(4-(4-propyl-1H-imidazol-2-yl)pyridin-2-yl)benzamide

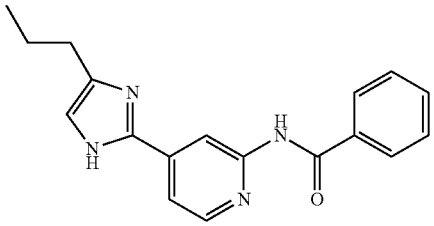 [SMILES: CCCc1c[nH]c(-c2ccnc(NC(=O)c3ccccc3)c2)n1]

Following the procedure as described in Example 10, making variations as required to replace N-(4-(4-methyl-4,5-dihydro-1H-imidazol-2-yl)pyridin-2-yl)benzamide with N-(4-(4-propyl-4,5-dihydro-1H-imidazol-2-yl)pyridin-2-yl)benzamide, N-(4-(4-propyl-1H-imidazol-2-yl)pyridin-2-yl)benzamide was obtained as a colorless solid in 35% yield: mp 95-97° C.; $^1$H NMR (300 MHz, CDCl$_3$) δ 9.16 (br s, 1H), 8.69 (s, 1H), 8.11 (d, J=5.3 Hz, 1H), 7.88-7.82 (m, 2H), 7.70 (dd, J=5.3, 1.4 Hz, 1H), 7.56-7.49 (m, 1H), 7.48-7.37 (m, 2H), 6.87 (s, 1H), 2.54 (t, J=7.4 Hz, 2H), 1.69-1.55 (m, 2H), 0.90 (t, J=7.4 Hz, 3H); MS (ES+) m/z 307.3 (M+1).

Example 10.2

Synthesis of N-(4-(4-benzyl-1H-imidazol-2-yl)pyridin-2-yl)benzamide

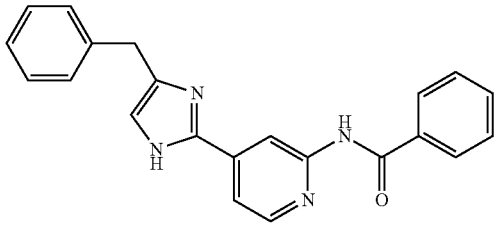

Following the procedure as described in Example 10, making variations as required to replace N-(4-(4-methyl-4,5-dihydro-1H-imidazol-2-yl)pyridin-2-yl)benzamide with N-(4-(4-benzyl-4,5-dihydro-1H-imidazol-2-yl)pyridin-2-yl)benzamide, N-(4-(4-benzyl-1H-imidazol-2-yl)pyridin-2-yl)benzamide was obtained as a colorless solid in 19% yield: mp 110-112° C.; $^1$H NMR (300 MHz, CDCl$_3$) δ 8.96 (br s, 1H), 8.62 (s, 1H), 8.18 (d, J=3.7 Hz, 1H), 7.83 (d, J=7.2 Hz, 2H), 7.70 (d, J=4.8 Hz, 1H), 7.58-7.50 (m, 1H), 7.48-7.40 (m, 2H), 7.30-7.14 (m, 5H), 6.81 (br s, 1H), 3.96 (s, 2H); MS (ES+) m/z 355.3 (M+1).

Example 10.3

Synthesis of N-(4-(4-isobutyl-1H-imidazol-2-yl)pyridin-2-yl)benzamide

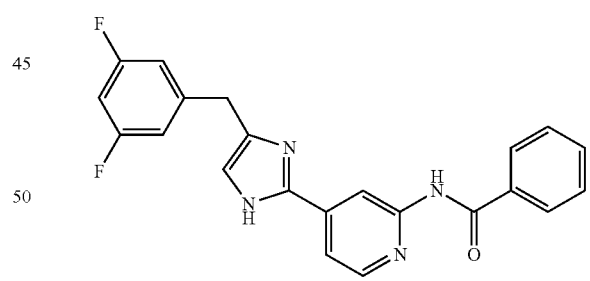

Following the procedure as described in Example 10, making non-critical variations as required to replace N-(4-(4-methyl-4,5-dihydro-1H-imidazol-2-yl)pyridin-2-yl)benzamide with N-(4-(4-isobutyl-4,5-dihydro-1H-imidazol-2-yl)pyridin-2-yl)benzamide, N-(4-(4-isobutyl-1H-imidazol-2-yl)pyridin-2-yl)benzamide was obtained as a colorless solid in 36% yield: mp 103-105° C.; $^1$H NMR (300 MHz, CDCl$_3$) δ 9.07 (br s, 1H), 8.68 (s, 1H), 8.17 (d, J=5.2 Hz, 1H), 7.86 (d, J=7.3 Hz, 2H), 7.73 (d, J=5.3 Hz, 1H), 7.59-7.40 (m, 3H), 6.89 (s, 1H), 2.45 (d, J=7.1 Hz, 2H), 1.98-1.79 (m, 1H), 0.90 (d, J=6.6 Hz, 6H); MS (ES+) m/z 321.3 (M+1).

Example 10.4

Synthesis of N-(4-(4-(3,5-difluorobenzyl)-1H-imidazol-2-yl)pyridin-2-yl)benzamide Following the procedure as described in Example 10, making variations as required to replace N-(4-(4-methyl-4,5-dihydro-1H-imidazol-2-yl)pyridin-2-yl)benzamide with N-(4-(4-(3,5-difluorobenzyl)-4,5-dihydro-1H-imidazol-2-yl)pyridin-2-yl)benzamide, N-(4-(4-(3,5-difluorobenzyl)-1H-imidazol-2-yl)pyridin-2-yl)benzamide was obtained as a colorless solid in 32% yield: $^1$H NMR (300 MHz, CDCl$_3$) δ 8.98 (br s, 1H), 8.67 (s, 1H), 8.22 (d, J=3.6 Hz, 1H), 7.88-7.81 (m, 2H), 7.73 (d, J=4.8 Hz, 1H), 7.61-7.40 (m, 3H), 6.82 (s, 1H), 6.78-6.70 (m, 1H), 6.66-6.57 (m, 2H), 3.94 (s, 2H); MS (ES+) m/z 391.1 (M+1).

Example 10.5

Synthesis of N-(4-(4-phenyl-1H-imidazol-2-yl)pyridin-2-yl)benzamide

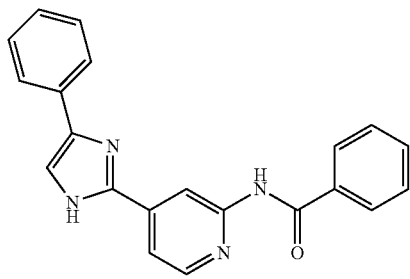 [SMILES: O=C(Nc1cc(-c2nc(-c3ccccc3)c[nH]2)ccn1)c1ccccc1]

Following the procedure as described in Example 10, making variations as required to replace N-(4-(4-methyl-4,5-dihydro-1H-imidazol-2-yl)pyridin-2-yl)benzamide with N-(4-(4-phenyl-4,5-dihydro-1H-imidazol-2-yl)pyridin-2-yl)benzamide, N-(4-(4-phenyl-1H-imidazol-2-yl)pyridin-2-yl)benzamide was obtained as a colorless solid in 13% yield: mp 265-267° C.; $^1$H NMR (300 MHz, DMSO-$d_6$) δ 13.14 (br s, 1H), 10.88 (br s, 1H), 8.81 (s, 1H), 8.47 (d, J=5.2 Hz, 1H), 8.10-8.05 (m, 2H), 7.93-7.88 (m, 2H), 7.72 (dd, J=5.2, 1.5 Hz, 1H), 7.65-7.36 (m, 6H), 7.28-7.21 (m, 1H); $^{13}$C NMR (75 MHz, DMSO-$d_6$) δ 165.9, 152.8, 148.5, 143.6, 141.9, 139.1, 134.1, 134.0, 131.9, 128.5, 128.4, 127.9, 126.5, 124.5, 115.8, 115.2, 110.0; MS (ES+) m/z 341.3 (M+1).

Example 11

Synthesis of N-(4-(5-phenyl-1,3,4-oxadiazol-2-yl)pyridin-2-yl)benzamide

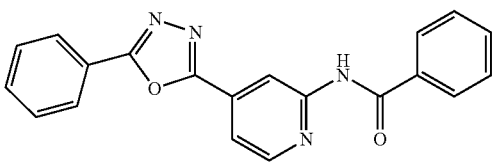 [SMILES: O=C(Nc1cc(-c2nnc(-c3ccccc3)o2)ccn1)c1ccccc1]

To a solution of N-(4-(2-benzoylhydrazinecarbonyl)pyridin-2-yl)benzamide (0.10 g, 0.27 mmol) in tetrahydrofuran (10 mL) was added (methoxycarbonylsulfamoyl)-triethylammonium hydroxide (0.35 g, 0.63 mmol) at ambient temperature. The resulting solution was refluxed for 7 hours and concentrated in vacuo to dryness. The residue was purified by column chromatography to give N-(4-(5-phenyl-1,3,4-oxadiazol-2-yl)pyridin-2-yl)benzamide (0.03 g 32%): mp 151-155° C.; $^1$H NMR (300 MHz, CDCl$_3$) δ 9.03-9.00 (m, 2H), 8.41 (br s, 1H), 8.19-7.97 (m, 2H), 7.97-7.94 (m, 2H), 7.84-7.83 (m, 1H), 7.61-7.48 (m, 6H); $^{13}$C NMR (75 MHz, CDCl$_3$) δ 168.1, 167.6, 164.9, 154.7, 151.1, 135.9, 135.4, 134.7, 134.3, 131.3, 131.1, 129.4, 127.3, 125.4, 119.0, 112.9; MS (ES+) m/z 343.5 (M+1).

Example 11.1

Synthesis of N-[4-(5-benzyl-[1,3,4]oxadiazol-2-yl)-pyridin-2-yl]benzamide

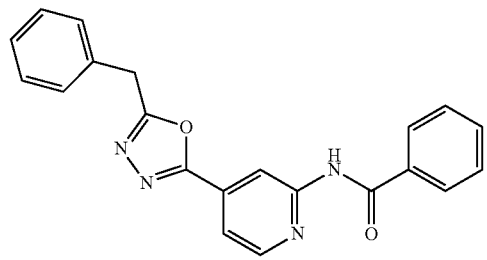 [SMILES: O=C(Nc1cc(-c2nnc(Cc3ccccc3)o2)ccn1)c1ccccc1]

Following the procedure as described in Example 11, making variations as required to replace N-(4-(2-benzoylhydrazinecarbonyl)pyridin-2-yl)benzamide with N-(4-(2-(2-phenylacetyl)hydrazinecarbonyl)pyridin-2-yl)benzamide to react with (methoxycarbonylsulfamoyl)triethylammonium hydroxide, N-[4-(5-benzyl-[1,3,4]oxadiazol-2-yl)-pyridin-2-yl]benzamide was obtained as a colorless solid in 17% yield: mp 187-189° C.; $^1$H NMR (300 MHz, CDCl$_3$) δ 9.14 (br s, 1H), 8.94 (br s, 1H), 8.36 (br s, 1H), 7.94 (d, J=7.9 Hz, 2H), 7.73 (br s, 1H), 7.55-7.51 (m, 3H), 7.39-7.20 (m, 5H), 4.29 (s, 2H); $^{13}$C NMR (75 MHz, CDCl$_3$) δ 166.6, 166.0, 163.5, 152.4, 148.4, 133.6, 133.4, 132.7, 129.1, 128.9, 128.8, 127.7, 127.4, 116.9, 111.3, 31.9; MS (ES+) m/z 357.2 (M+1).

Example 12

Synthesis of N-[4-(3-benzyl-[1,2,4]oxadiazol-5-yl)-pyridin-2-yl]benzamide

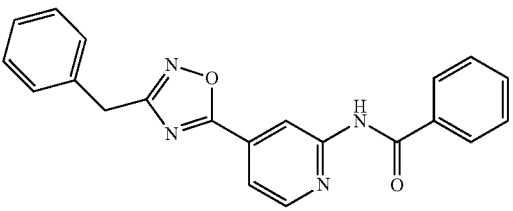 [SMILES: O=C(Nc1cc(-c2nc(Cc3ccccc3)no2)ccn1)c1ccccc1]

To a solution of 2-benzamidoisonicotinic acid (0.35 g, 1.44 mmol) and N,N-dimethylformamide (0.1 mL) in dichloromethane (5 mL) was added oxalyl chloride (0.15 mL, 1.73 mmol) at ambient temperature. The resulting mixture was stirred at ambient temperature for 1 hour and concentrated in vacuo to dryness. The residue was dissolved in N,N-dimethylformamide (2 mL) and added to a solution of N'-hydroxy-2-phenylacetimidamide (0.24 g, 1.59 mmol) and pyridine (0.3 mL, 3.70 mmol) in N,N-dimethylformamide (1 mL) at 0° C. The reaction mixture was stirred at ambient temperature for 3 hours, diluted with ethyl acetate (40 mL), washed with water (20 mL) and brine (20 mL). The organic solution was dried over anhydrous sodium sulphate, filtered and concentrated in vacuo. The residue was dissolved in toluene (10 mL), followed by the addition of (methoxycarbonylsulfamoyl)triethylammonium hydroxide (0.53 g, 2.16 mmol). The mixture was refluxed for 1 hour and concentrated in vacuo. The residue was purified by column chromatography to give N-[4-(3-benzyl-[1,2,4]oxadiazol-5-yl)-pyridin-2-yl]-benzamide as a colorless solid (0.06 g 12%): mp 150-151° C.; $^1$H NMR (300 MHz, CDCl$_3$) δ 9.06 (s, 1H), 8.69 (s, 1H), 8.46 (d, J=4.9 Hz, 1H), 7.94-7.91 (m, 2H), 7.72-7.69 (m, 1H), 7.62-7.48 (m, 3H), 7.39-7.24 (m, 5H), 4.16 (s, 2H); MS (ES+) m/z 357.5 (M+1).

Example 13

Synthesis of 2-(3-(4-fluorobenzyl)-2-oxoimidazolidin-1-yl)-N-methylisonicotinamide

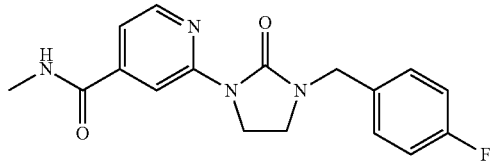 [SMILES: CNC(=O)c1ccnc(N2CCN(Cc3ccc(F)cc3)C2=O)c1]

To a solution of 2-(3-(4-fluorobenzyl)-2-oxoimidazolidin-1-yl)isonicotinic acid (0.18 g, 0.56 mmol) and 4-methylmorpholine (0.12 g, 1.18 mmol) in anhydrous tetrahydrofuran (15 mL) was added isobutyl chloroformate (0.10 g, 0.69 mmol) at 0° C. The resulting solution was stirred at ambient temperature for 3 hours, followed by the addition of methylamine hydrochloride (0.08 g, 1.12 mmol) and 4-methylmorpholine (0.06 g, 0.56 mmol) at 0° C. The reaction mixture was stirred for 17 hours and concentrated in vacuo. The residue was purified by column chromatography to give 2-(3-(4-fluorobenzyl)-2-oxoimidazolidin-1-yl)-N-methylisonicotinamide as a colorless solid (0.08 g, 43%): mp 118-120° C.; $^1$H NMR (300 MHz, CDCl$_3$) δ 8.54 (s, 1H), 8.36-8.34 (m, 1H), 7.40-7.37 (m, 1H), 7.29-7.24 (m, 2H), 7.06-6.99 (m, 2H), 6.47 (br s, 1H), 4.44 (s, 2H), 4.07-4.01 (m, 2H), 3.40-3.35 (m, 2H), 2.98 (d, J=4.8 Hz, 3H); $^{13}$C NMR (75 MHz, CDCl$_3$) δ 166.5, 153.0, 148.4, 143.1, 132.1, 129.9, 129.8, 116.1, 115.9, 115.6, 108.8, 47.3, 41.3, 41.0, 26.8; MS (ES+) m/z 329.2 (M+1).

Example 14

Synthesis of 2-(3-(4-fluorobenzyl)-2-oxoimidazolidin-1-yl)-N-(oxazol-4-ylmethyl)isonicotinamide

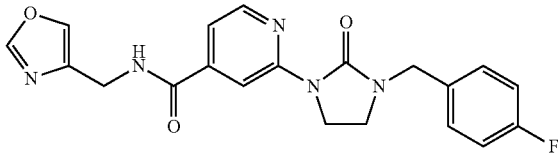 [SMILES: O=C(NCc1cocn1)c1ccnc(N2CCN(Cc3ccc(F)cc3)C2=O)c1]

A solution of 2-(3-(4-fluorobenzyl)-2-oxoimidazolidin-1-yl)isonicotinic acid (0.35 g, 1.11 mmol), diisopropylethylamine (0.86 g, 6.66 mmol), 1-hydroxybenzotriazole monohydrate (0.39 g, 2.89 mmol) and 1-(3-dimethylaminopropyl)-3-ethylcarbodiimide hydrochloride (0.28 g, 1.44 mmol) in anhydrous N,N-dimethylformamide (10.0 mL) was stirred at ambient temperature for 10 minutes, followed by the addition of oxazol-4-ylmethanamine (0.23 g, 1.67 mmol). The resulting reaction mixture was stirred at ambient temperature for 17 hours and concentrated in vacuo. The residue was dissolved in ethyl acetate (60 mL), washed with saturated aqueous sodium bicarbonate (10 mL) solution, water (2×10 mL) and brine (10 mL). The organic solution was dried over anhydrous sodium sulphate, filtered and concentrated in vacuo. The residue was purified by column chromatography to give 2-(3-(4-fluorobenzyl)-2-oxoimidazolidin-1-yl)-N-(oxazol-4-ylmethyl)isonicotinamide as a colorless solid (0.21 g, 49%): mp 197-199° C.; $^1$H NMR (300 MHz, DMSO-d$_6$) δ 9.15 (t, J=5.6 Hz, 1H), 8.65 (s, 1H), 8.37-8.30 (m, 2H), 7.95 (s, 1H), 7.35-7.06 (m, 5H), 4.49-4.33 (m, 4H), 3.93 (t, J=8.0 Hz, 2H), 3.37-3.25 (m, 2H); $^{13}$C NMR (75 MHz, DMSO-d$_6$) δ 165.6, 163.6, 160.4, 156.8, 153.5, 152.5, 148.4, 143.3, 137.8, 136.6, 133.6, 133.6, 130.4, 130.3, 116.0, 115.7, 115.2, 110.5, 46.6, 41.6, 35.7; MS (ES+) m/z 396.3 (M+1).

Example 14.1

Synthesis of 2-(3-(4-fluorobenzyl)-2-oxoimidazolidin-1-yl)-N-(thiazol-5-ylmethyl)isonicotinamide

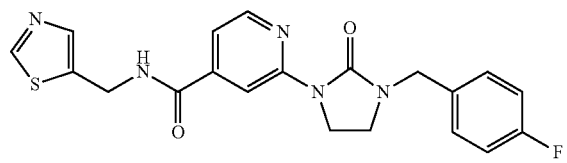 [SMILES: O=C(NCc1cncs1)c1ccnc(N2CCN(Cc3ccc(F)cc3)C2=O)c1]

Following the procedure as described in Example 14, making variations as required to replace oxazol-4-ylmethanamine with thiazol-5-ylmethanamine to react with 2-(3-(4-fluorobenzyl)-2-oxoimidazolidin-1-yl)isonicotinic acid, 2-(3-(4-fluorobenzyl)-2-oxoimidazolidin-1-yl)-N-(thiazol-5-ylmethyl)isonicotinamide was obtained as a colorless solid in 43% yield: mp 148-150° C.; $^1$H NMR (300 MHz, DMSO-d$_6$) δ 9.39 (t, J=5.7 Hz, 1H), 9.02 (s, 1H), 8.65 (s, 1H), 8.36 (d, J=5.1 Hz, 1H), 7.80 (s, 1H), 7.35-7.29 (m, 3H), 7.19-7.13 (m, 2H), 4.64 (d, J=5.7 Hz, 2H), 4.39 (s, 2H), 3.93 (t, J=8.0 Hz, 2H), 3.34 (t, J=8.0 Hz, 2H); MS (ES+) m/z 412.0 (M+1).

Example 14.2

Synthesis of 2-(3-(4-fluorobenzyl)-2-oxoimidazolidin-1-yl)-N-((5-methylpyrazin-2-yl)methyl)isonicotinamide

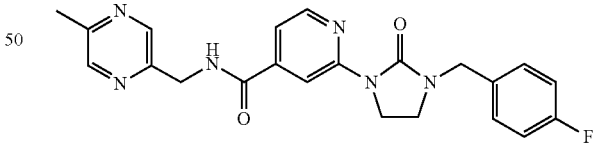

Following the procedure as described in Example 14, making variations as required to replace oxazol-4-ylmethanamine with (5-methylpyrazin-2-yl)methanamine to react with 2-(3-(4-fluorobenzyl)-2-oxoimidazolidin-1-yl)isonicotinic acid, 2-(3-(4-fluorobenzyl)-2-oxoimidazolidin-1-yl)-N-((5-methylpyrazin-2-yl)methyl)isonicotinamide was obtained as a colorless solid in 39% yield: mp 169-171° C.; $^1$H NMR (300 MHz, CDCl$_3$) δ 8.65 (s, 1H), 8.52 (d, J=0.9 Hz, 1H), 8.39-8.35 (m, 2H), 7.46 (br s, 1H), 7.39-7.37 (m, 1H), 7.29-7.24 (m, 2H), 7.05-6.99 (m, 2H), 4.74 (d, J=5.1 Hz, 2H), 4.44 (s, 2H), 4.04 (t, J=8.1 Hz, 2H), 3.37 (t, J=8.1 Hz, 2H), 2.54 (s, 3H); MS (ES+) m/z 421.1 (M+1).

Example 14.3

Synthesis of 2-(3-(4-fluorobenzyl)-2-oxoimidazolidin-1-yl)-N-(thiazol-2-ylmethyl)isonicotinamide

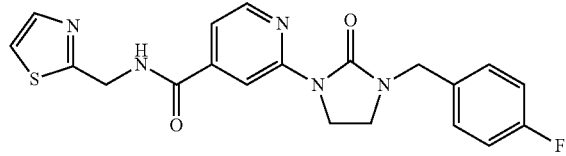

Following the procedure as described in Example 14, making variations as required to replace oxazol-4-ylmethanamine with thiazol-2-ylmethanamine to react with 2-(3-(4-fluorobenzyl)-2-oxoimidazolidin-1-yl)isonicotinic acid, 2-(3-(4-fluorobenzyl)-2-oxoimidazolidin-1-yl)-N-(thiazol-2-ylmethyl)isonicotinamide was obtained as a colorless solid in 88% yield: mp 123-125° C.; NMR (300 MHz, CDCl$_3$) δ 8.64 (s, 1H), 8.35 (d, J=5.1 Hz, 1H), 7.70 (d, J=2.7 Hz, 1H), 7.39-7.21 (m, 5H), 7.04-6.99 (m, 2H), 4.93 (d, J=5.7 Hz, 2H), 4.42 (s, 2H), 4.02 (t, J=8.1 Hz, 2H), 3.36 (t, J=8.1 Hz, 2H); MS (ES+) m/z 411.9 (M+1).

Example 14.4

Synthesis of 2-(3-(4-fluorobenzyl)-2-oxoimidazolidin-1-yl)-N-(oxazol-2-ylmethyl)isonicotinamide

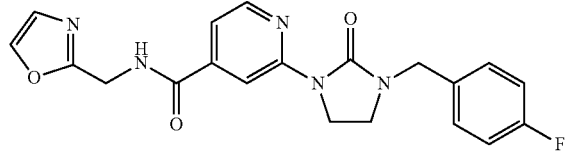 [SMILES: O=C(NCc1ncco1)c1ccnc(N2CCN(Cc3ccc(F)cc3)C2=O)c1]

Following the procedure as described in Example 14, making variations as required to replace oxazol-4-ylmethanamine with oxazol-2-ylmethanamine to react with 2-(3-(4-fluorobenzyl)-2-oxoimidazolidin-1-yl)isonicotinic acid, 2-(3-(4-fluorobenzyl)-2-oxoimidazolidin-1-yl)-N-(oxazol-2-ylmethyl)isonicotinamide was obtained as a colorless solid in 49% yield: mp 148-150° C.; $^1$H NMR (300 MHz, DMSO-d$_6$) δ 9.36 (t, J=5.7 Hz, 1H), 8.60 (s, 1H), 8.38 (d, J=5.1 Hz, 2H), 8.03 (s, 1H), 7.36-7.31 (m, 3H), 7.18-7.07 (m, 2H), 4.55 (d, J=5.7 Hz, 2H), 4.39 (s, 2H), 3.94 (t, J=8.1 Hz, 2H), 3.45 (t, J=8.0 Hz, 2H); MS (ES+) m/z 396.0 (M+1).

Example 14.5

Synthesis of 2-(3-(4-fluorobenzyl)-2-oxoimidazolidin-1-yl)-N-((1-methyl-1H-imidazol-4-yl)methyl)isonicotinamide

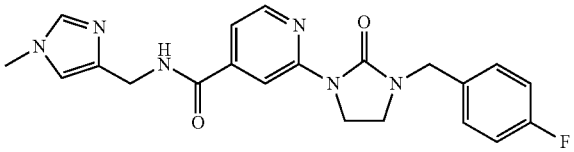 [SMILES: Cn1cnc(CNC(=O)c2ccnc(N3CCN(Cc4ccc(F)cc4)C3=O)c2)c1]

Following the procedure as described in Example 14, making variations as required to replace oxazol-4-ylmethanamine with (1-methyl-1H-imidazol-4-yl)methanamine to react with 2-(3-(4-fluorobenzyl)-2-oxoimidazolidin-1-yl)isonicotinic acid, 2-(3-(4-fluorobenzyl)-2-oxoimidazolidin-1-yl)-N-((1-methyl-1H-imidazol-4-yl)methyl)isonicotinamide was obtained as a colorless solid in 52% yield: mp 174-176° C.; $^1$H NMR (300 MHz, DMSO-d$_6$) δ 9.01 (t, J=5.6 Hz, 1H), 8.57 (s, 1H), 8.34 (d, J=5.1 Hz, 1H), 7.45 (s, 1H), 7.35-7.31 (m, 3H), 7.19-7.12 (m, 2H), 6.93 (s, 1H), 4.38 (s, 2H), 4.28 (d, J=5.7 Hz, 2H), 3.93 (t, J=8.1 Hz, 2H), 3.56 (s, 3H), 3.34 (t, J=8.1 Hz, 2H); MS (ES+) m/z 409.1 (M+1).

Example 14.6

Synthesis of 2-(3-(4-fluorobenzyl)-2-oxoimidazolidin-1-yl)-N-((1-methyl-1H-pyrazol-3-yl)methyl)isonicotinamide

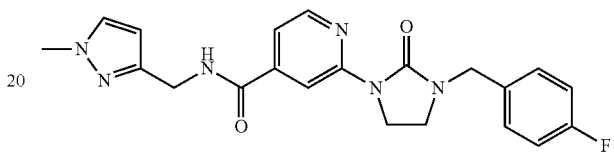

Following the procedure as described in Example 14, making variations as required to replace oxazol-4-ylmethanamine with (1-methyl-1H-pyrazol-3-yl)methanamine to react with 2-(3-(4-fluorobenzyl)-2-oxoimidazolidin-1-yl)isonicotinic acid, 2-(3-(4-fluorobenzyl)-2-oxoimidazolidin-1-yl)-N-((1-methyl-1H-pyrazol-3-yl)methyl)isonicotinamide was obtained as a colorless solid in 30% yield: mp 79-81° C.; $^1$H NMR (300 MHz, CDCl$_3$) δ 8.57 (s, 1H), 8.33 (d, J=5.1 Hz, 1H), 7.37 (dd, J=5.1 Hz, 1.2 Hz, 1H), 7.27-7.22 (m, 3H), 7.03-6.91 (m, 3H), 6.19 (d, J=2.1 Hz, 1H), 4.60 (d, J=5.1 Hz, 2H), 4.41 (s, 2H), 4.02 (t, J=8.1 Hz, 2H), 3.84 (s, 3H), 3.34 (t, J=8.1 Hz, 2H); MS (ES+) m/z 408.8 (M+1).

Example 14.7

Synthesis of 2-(3-(4-fluorobenzyl)-2-oxoimidazolidin-1-yl)-N-((1,3,5-trimethyl-1H-pyrazol-4-yl)methyl)isonicotinamide

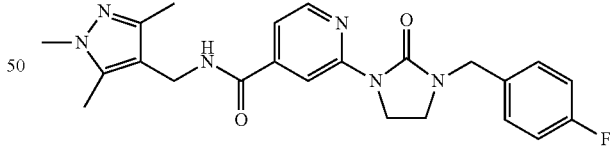

Following the procedure as described in Example 14, making variations as required to replace oxazol-4-ylmethanamine with (1,3,5-trimethyl-1H-pyrazol-4-yl)methanamine to react with 2-(3-(4-fluorobenzyl)-2-oxoimidazolidin-1-yl)isonicotinic acid, 2-(3-(4-fluorobenzyl)-2-oxoimidazolidin-1-yl)-N-((1,3,5-trimethyl-1H-pyrazol-4-yl)methyl)isonicotinamide was obtained as a colorless solid in 67% yield: mp 179-181° C.; $^1$H NMR (300 MHz, CDCl$_3$) δ 8.48 (s, 1H), 8.33 (d, J=5.1 Hz, 1H), 7.37 (dd, J=5.1 Hz, 1.2 Hz, 1H), 7.25-7.21 (m, 2H), 7.03-6.97 (m, 2H), 6.35 (br s, 1H), 4.40-4.36 (m, 4H), 4.01 (t, J=8.1 Hz, 2H), 3.68 (s, 3H), 3.34 (t, J=8.1 Hz, 2H), 2.21 (s, 3H), 2.19 (s, 3H); MS (ES+) m/z 436.8 (M+1).

Example 14.8

Synthesis of 2-(3-(4-fluorobenzyl)-2-oxoimidazolidin-1-yl)-N-((1-methyl-1H-pyrazol-4-yl)methyl)isonicotinamide

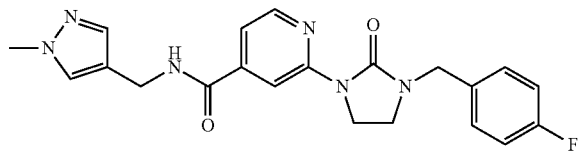 [SMILES: Cn1cc(CNC(=O)c2ccnc(N3CCN(Cc4ccc(F)cc4)C3=O)c2)cn1]

Following the procedure as described in Example 14, making variations as required to replace oxazol-4-ylmethanamine with (1-methyl-1H-pyrazol-4-yl)methanamine to react with 2-(3-(4-fluorobenzyl)-2-oxoimidazolidin-1-yl)isonicotinic acid, 2-(3-(4-fluorobenzyl)-2-oxoimidazolidin-1-yl)-N-((1-methyl-1H-pyrazol-4-yl)methyl)isonicotinamide was obtained as a colorless solid in 23% yield: mp 165-166° C.; $^1$HNMR (300 MHz, CDCl$_3$) δ 8.52 (s, 1H), 8.34 (d, J=5.1 Hz, 1H), 7.44-7.37 (m, 3H), 7.27-7.22 (m, 2H), 7.04-6.98 (m, 2H), 6.70 (br s, 1H), 4.45-4.41 (m, 4H), 4.03 (t, J=8.1 Hz, 2H), 3.84 (s, 3H), 3.36 (t, J=8.1 Hz, 2H); $^{13}$C NMR (75 MHz, CDCl$_3$) δ 165.5, 164.0, 160.7, 157.0, 152.9, 148.2, 143.0, 138.9, 132.1, 132.0, 129.9, 129.8, 116.0, 115.9, 115.6, 109.0, 47.2, 41.3, 41.0, 39.0, 34.5; MS (ES+) m/z 408.9 (M+1).

Example 14.9

Synthesis of N-((1H-pyrazol-3-yl)methyl)-2-(3-(4-fluorobenzyl)-2-oxoimidazolidin-1-yl)isonicotinamide

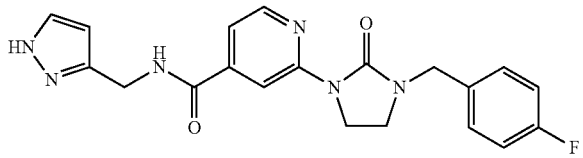 [SMILES: O=C(NCc1cc[nH]n1)c1ccnc(N2CCN(Cc3ccc(F)cc3)C2=O)c1]

Following the procedure as described in Example 14, making variations as required to replace oxazol-4-ylmethanamine with (1H-pyrazol-3-yl)methanamine to react with 2-(3-(4-fluorobenzyl)-2-oxoimidazolidin-1-yl)isonicotinic acid, N-((1H-pyrazol-3-yl)methyl)-2-(3-(4-fluorobenzyl)-2-oxoimidazolidin-1-yl)isonicotinamide was obtained as a colorless solid in 23% yield: mp 178-180° C.; $^1$H NMR (300 MHz, CDCl$_3$) δ 8.60 (s, 1H), 8.33-8.24 (m, 2H), 7.45-7.37 (m, 2H), 7.32-7.17 (m, 3H), 7.04-6.94 (m, 2H), 6.27 (s, 1H), 4.70 (d, J=5.7 Hz, 2H), 4.43 (s, 2H), 4.03 (t, J=8.1 Hz, 2H), 3.37 (t, J=8.1 Hz, 2H); MS (ES+) m/z 394.9 (M+1).

Example 14.10

Synthesis of 2-(3-(4-fluorobenzyl)-2-oxoimidazolidin-1-yl)-N-((5-methylisoxazol-3-yl)methyl)isonicotinamide

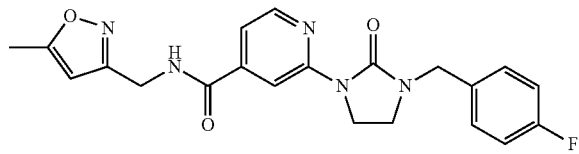 [SMILES: Cc1cc(CNC(=O)c2ccnc(N3CCN(Cc4ccc(F)cc4)C3=O)c2)no1]

Following the procedure as described in Example 14, making variations as required to replace oxazol-4-ylmethanamine with (5-methylisoxazol-3-yl)methanamine to react with 2-(3-(4-fluorobenzyl)-2-oxoimidazolidin-1-yl)isonicotinic acid, 2-(3-(4-fluorobenzyl)-2-oxoimidazolidin-1-yl)-N-((5-methylisoxazol-3-yl)methyl)isonicotinamide was obtained as a colorless solid in 55% yield: mp 153-155° C.; $^1$H NMR (300 MHz, CDCl$_3$) δ 8.59 (s, 1H), 8.35 (d, J=5.1 Hz, 1H), 7.37-7.35 (m, 1H), 7.28-7.23 (m, 2H), 7.07-6.99 (m, 3H), 6.01 (s, 1H), 4.63 (d, J=5.7 Hz, 2H), 4.42 (s, 2H), 4.03 (t, J=8.1 Hz, 2H), 3.36 (t, J=8.1 Hz, 2H), 2.37 (s, 3H); MS (ES+) m/z 409.9 (M+1).

Example 14.11

Synthesis of N-((1,5-dimethyl-1H-pyrazol-3-yl)methyl)-2-(3-(4-fluorobenzyl)-2-oxoimidazolidin-1-yl)isonicotinamide

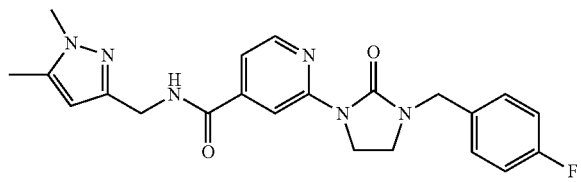 [SMILES: Cc1cc(CNC(=O)c2ccnc(N3CCN(Cc4ccc(F)cc4)C3=O)c2)nn1C]

Following the procedure as described in Example 14, making variations as required to replace oxazol-4-ylmethanamine with (1,5-dimethyl-1H-pyrazol-3-yl)methanamine to react with 2-(3-(4-fluorobenzyl)-2-oxoimidazolidin-1-yl)isonicotinic acid, N-((1,5-dimethyl-1H-pyrazol-3-yl)methyl)-2-(3-(4-fluorobenzyl)-2-oxoimidazolidin-1-yl)isonicotinamide was obtained as a colorless solid in 70% yield: mp 150-152° C.; $^1$H NMR (300 MHz, CDCl$_3$) δ 8.57 (s, 1H), 8.33 (d, J=5.1 Hz, 1H), 7.38-7.36 (m, 1H), 7.28-7.23 (m, 2H), 7.05-6.97 (m, 2H), 6.87 (br s, 1H), 5.98 (s, 1H), 4.53 (d, J=5.1 Hz, 2H), 4.42 (s, 2H), 4.02 (t, J=8.1 Hz, 2H), 3.71 (s, 3H), 3.35 (t, J=8.1 Hz, 2H), 2.21 (s, 3H); MS (ES+) m/z 422.9 (M+1).

Example 14.12

Synthesis of (R)-2-(3-(4-fluorobenzyl)-2-oxoimidazolidin-1-yl)-N-(2-hydroxy-2-phenylethyl)isonicotinamide

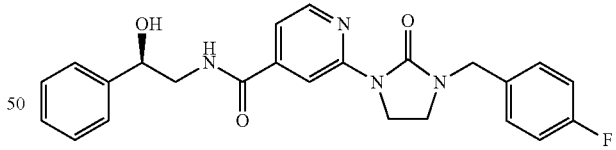

Following the procedure as described in Example 14, making variations as required to replace oxazol-4-ylmethanamine with (R)-2-amino-1-phenylethanol to react with 2-(3-(4-fluorobenzyl)-2-oxoimidazolidin-1-yl)isonicotinic acid, (R)-2-(3-(4-fluorobenzyl)-2-oxoimidazolidin-1-yl)-N-(2-hydroxy-2-phenylethyl)isonicotinamide was obtained as a colorless solid in 49% yield: mp 97-99° C.; $^1$H NMR (300 MHz, CDCl$_3$) δ 8.49 (s, 1H), 8.32 (d, J=5.4 Hz, 1H), 7.65 (br s, 1H), 7.39-7.16 (m, 8H), 7.02-6.96 (m, 2H), 5.00 (d, J=6.9 Hz, 1H), 4.36-4.27 (m, 3H), 4.03-3.87 (m, 3H), 3.46-3.31 (m, 3H); $^{13}$C NMR (75 MHz, CDCl$_3$) δ 166.7, 164.0, 160.8, 156.9, 152.6, 148.0, 143.2, 141.9, 131.9, 131.9, 129.9, 129.8, 128.5, 127.8, 125.8, 116.2, 115.9, 115.6, 109.5, 48.1, 47.2, 41.4, 41.0; MS (ES+) m/z 434.7 (M+1).

Example 14.13

Synthesis of 2-(3-(4-fluorobenzyl)-2-oxoimidazolidin-1-yl)-N-((2-methylthiazol-4-yl)methyl)isonicotinamide

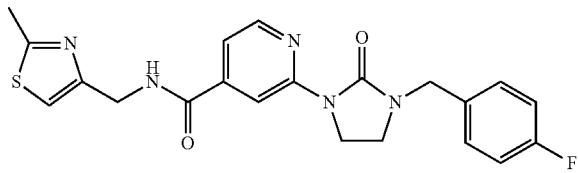 [SMILES: Cc1nc(CNC(=O)c2ccnc(N3CCN(Cc4ccc(F)cc4)C3=O)c2)cs1]

Following the procedure as described in Example 14, making variations as required to replace oxazol-4-ylmethanamine with (2-methylthiazol-4-yl)methanamine to react with 2-(3-(4-fluorobenzyl)-2-oxoimidazolidin-1-yl)isonicotinic acid, 2-(3-(4-fluorobenzyl)-2-oxoimidazolidin-1-yl)-N-((2-methylthiazol-4-yl)methyl)isonicotinamide was obtained as a colorless solid in 26% yield: mp 76-78° C.; $^1$H NMR (300 MHz, CDCl$_3$) δ 8.60 (d, J=0.6 Hz, 1H), 8.34 (d, J=5.7 Hz, 1H), 7.36 (dd, J=5.4, 1.5 Hz, 1H), 7.28-7.24 (m, 2H), 7.05-6.99 (m, 4H), 4.66 (d, J=5.7 Hz, 2H), 4.43 (s, 2H), 4.03 (t, J=8.1 Hz, 2H), 3.36 (t, J=8.1 Hz, 2H), 2.68 (s, 3H); MS (ES+) m/z 425.8 (M+1).

Example 14.14

Synthesis of 2-(3-(4-fluorobenzyl)-2-oxoimidazolidin-1-yl)-N-(isoxazol-3-ylmethyl)isonicotinamide

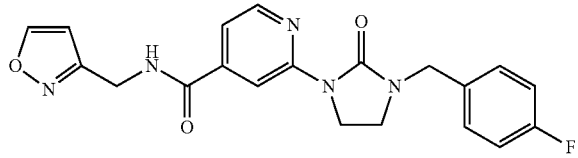 [SMILES: O=C(NCc1ccon1)c1ccnc(N2CCN(Cc3ccc(F)cc3)C2=O)c1]

Following the procedure as described in Example 14, making variations as required to replace oxazol-4-ylmethanamine with isoxazol-3-ylmethanamine to react with 2-(3-(4-fluorobenzyl)-2-oxoimidazolidin-1-yl)isonicotinic acid, 2-(3-(4-fluorobenzyl)-2-oxoimidazolidin-1-yl)-N-(isoxazol-3-ylmethyl)isonicotinamide was obtained as a colorless solid in 53% yield: mp 127-129° C.; $^1$H NMR (300 MHz, CDCl$_3$) δ 8.61 (s, 1H), 8.37-8.34 (m, 2H), 7.36 (dd, J=5.1 Hz, 1.2 Hz, 1H), 7.31-7.23 (m, 2H), 7.04-6.98 (m, 3H), 6.39 (d, J=1.5 Hz, 1H), 4.73 (d, J=6.0 Hz, 2H), 4.42 (s, 2H), 4.03 (t, J=8.1 Hz, 2H), 3.36 (t, J=8.1 Hz, 2H); MS (ES+) m/z 395.7 (M+1).

Example 14.15

Synthesis of 2-(3-(4-fluorobenzyl)-2-oxoimidazolidin-1-yl)-N-((2-(trifluoromethyl)thiazol-4-yl)methyl)isonicotinamide

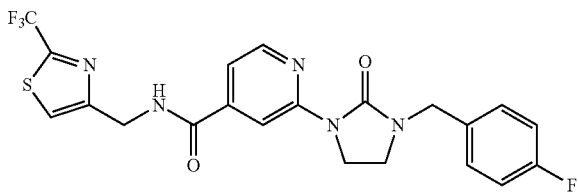 [SMILES: O=C(NCc1csc(C(F)(F)F)n1)c1ccnc(N2CCN(Cc3ccc(F)cc3)C2=O)c1]

Following the procedure as described in Example 14, making variations as required to replace oxazol-4-ylmethanamine with (2-(trifluoromethyl)thiazol-4-yl)methanamine to react with 2-(3-(4-fluorobenzyl)-2-oxoimidazolidin-1-yl)isonicotinic acid, 2-(3-(4-fluorobenzyl)-2-oxoimidazolidin-1-yl)-N-((2-(trifluoromethyl)thiazol-4-yl)methyl)isonicotinamide was obtained as a colorless solid in 30% yield: mp 66-68° C.; $^1$H NMR (300 MHz, CDCl$_3$) δ 8.68 (s, 1H), 8.36 (d, J=5.1 Hz, 1H), 7.59 (s, 1H), 7.35 (d, J=5.1 Hz, 1H), 7.28-7.20 (m, 2H), 7.17-6.99 (m, 3H), 4.78 (d, J=6.0 Hz, 2H), 4.43 (s, 2H), 4.03 (t, J=8.0 Hz, 2H), 3.37 (t, J=8.0 Hz, 2H); MS (ES+) m/z 479.8 (M+1).

Example 14.16

Synthesis of 2-(3-(4-fluorobenzyl)-2-oxoimidazolidin-1-yl)-N-((4-methyl-2-phenylthiazol-5-yl)methyl)isonicotinamide

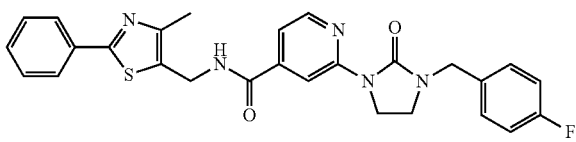 [SMILES: Cc1nc(-c2ccccc2)sc1CNC(=O)c1ccnc(N2CCN(Cc3ccc(F)cc3)C2=O)c1]

Following the procedure as described in Example 14, making variations as required to replace oxazol-4-ylmethanamine with (4-methyl-2-phenylthiazol-5-yl)methanamine to react with 2-(3-(4-fluorobenzyl)-2-oxoimidazolidin-1-yl)isonicotinic acid, 2-(3-(4-fluorobenzyl)-2-oxoimidazolidin-1-yl)-N-((4-methyl-2-phenylthiazol-5-yl)methyl)isonicotinamide was obtained as a colorless solid in 53% yield: mp 182-184° C.; $^1$HNMR (300 MHz, CDCl$_3$) δ 8.57 (s, 1H), 8.36 (d, J=5.7 Hz, 1H), 7.87-7.84 (m, 2H), 7.42-7.37 (m, 4H), 7.24-7.20 (m, 2H), 7.03-6.93 (m, 3H), 4.75 (d, J=5.7 Hz, 2H), 4.40 (s, 2H), 4.02 (t, J=8.1 Hz, 2H), 3.35 (t, J=8.1 Hz, 2H), 2.49 (s, 3H); $^{13}$C NMR (75 MHz, CDCl$_3$) δ 166.1, 165.6, 164.0, 160.7, 157.0, 153.0, 151.1, 148.5, 142.4, 133.6, 132.0, 129.9, 129.8, 128.9, 127.7, 126.4, 116.0, 115.8, 115.6, 109.0, 47.2, 41.3, 41.0, 35.8, 15.3; MS (ES+) m/z 501.9 (M+1).

Example 15

Synthesis of N-benzyl-2-(3-(4-fluorobenzyl)-2-oxoimidazolidin-1-yl)isonicotinamide

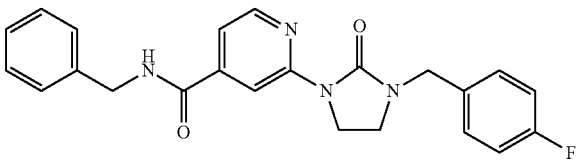 [SMILES: O=C(NCc1ccccc1)c1ccnc(N2CCN(Cc3ccc(F)cc3)C2=O)c1]

A solution of methyl 2-(3-(4-fluorobenzyl)-2-oxoimidazolidin-1-yl)isonicotinate (0.26 g, 0.78 mmol) and sodium cyanide (78 mg, 1.56 mmol) in benzylamine (5.0 mL) was stirred at 95° C. for 16 hours and concentrated in vacuo. The residue was purified by column chromatography eluting with 0 to 90% of ethyl acetate in hexanes to give N-benzyl-2-(3-(4-fluorobenzyl)-2-oxoimidazolidin-1-yl)isonicotinamide as a colorless solid (0.19 g, yield 59%): mp 167-169° C.; $^1$HNMR (300 MHz, CDCl$_3$) δ 8.57 (d, J=0.6 Hz, 1H), 8.37 (d, J=5.1 Hz, 1H), 7.42-7.18 (m, 8H), 7.08-6.98 (m, 2H), 6.79 (br s, 1H), 4.62 (d, J=6.0 Hz, 2H), 4.41 (s, 2H), 4.03 (t, J=7.5 Hz, 2H), 3.36 (t, J=7.8 Hz, 2H); $^{13}$C NMR (75 MHz, CDCl$_3$) δ 165.7, 164.0, 160.7, 157.0, 153.0, 148.4, 143.0, 137.7, 132.1, 132.0, 129.9, 129.8, 128.8, 128.0, 127.7, 116.1, 115.8, 115.6, 109.0, 47.2, 44.2, 41.3, 41.0; MS (ES+) m/z 405.2 (M+1).

Example 15.1

Synthesis of 2-(3-(4-fluorobenzyl)-2-oxoimidazolidin-1-yl)-N-(pyridin-3-ylmethyl)isonicotinamide

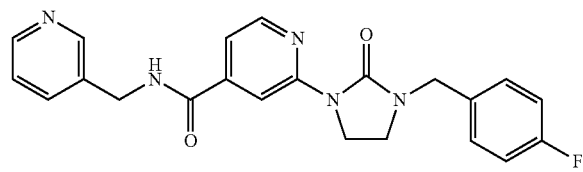 [SMILES: O=C(NCc1cccnc1)c1ccnc(N2CCN(Cc3ccc(F)cc3)C2=O)c1]

Following the procedure as described in Example 15, making variations as required to replace benzylamine with pyridin-3-ylmethanamine to react with methyl 2-(3-(4-fluorobenzyl)-2-oxoimidazolidin-1-yl)isonicotinate, 2-(3-(4-fluorobenzyl)-2-oxoimidazolidin-1-yl)-N-(pyridin-3-ylmethyl)isonicotinamide was obtained as a colorless solid in 39% yield: mp 153-155° C.; $^1$H NMR (300 MHz, DMSO-d$_6$) δ 9.29 (br, 1H), 8.60 (s, 1H), 8.52 (d, J=2.1 Hz, 1H), 8.44-8.42 (m, 1H), 8.37 (d, J=5.4 Hz, 1H), 7.71-7.68 (m, 1H), 7.35-7.31 (m, 4H), 7.18-7.13 (m, 2H), 4.46 (d, J=6.0 Hz, 2H), 4.39 (s, 2H), 3.93 (t, J=7.5 Hz, 2H), 3.38-3.34 (m, 2H); $^{13}$C NMR (75 MHz, CDCl$_3$) δ 165.8, 156.8, 153.5, 149.3, 148.7, 148.5, 143.2, 135.7, 135.1, 133.6, 133.6, 130.4, 130.3, 124.0, 116.0, 115.7, 115.2, 110.4, 46.6, 41.6, 41.2, 41.0; MS (ES+) m/z 406.2 (M+1).

Example 15.2

Synthesis of 2-(3-(4-fluorobenzyl)-2-oxoimidazolidin-1-yl)-N-(pyridin-4-ylmethyl)isonicotinamide

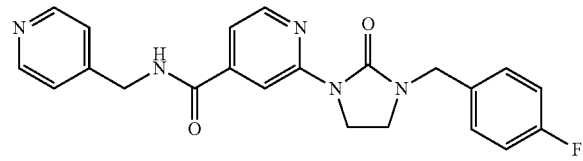 [SMILES: O=C(NCc1ccncc1)c1ccnc(N2CCN(Cc3ccc(F)cc3)C2=O)c1]

Following the procedure as described in Example 15, making variations as required to replace benzylamine with pyridin-4-ylmethanamine to react with methyl 2-(3-(4-fluorobenzyl)-2-oxoimidazolidin-1-yl)isonicotinate, 2-(3-(4-fluorobenzyl)-2-oxoimidazolidin-1-yl)-N-(pyridin-4-ylmethyl)isonicotinamide was obtained as a colorless solid in 42% yield: mp 205-207° C.; $^1$H NMR (300 MHz, DMSO-d$_6$) δ 9.33 (t, J=6.0 Hz, 1H), 8.62 (s, 1H), 8.49-8.47 (m, 2H), 8.39 (d, J=5.4 Hz, 1H), 7.37-7.26 (m, 5H), 7.18-7.13 (m, 2H), 4.47 (d, J=5.7 Hz, 2H), 4.39 (s, 2H), 3.94 (t, J=7.5 Hz, 2H), 3.38-3.32 (m, 2H); $^{13}$C NMR (75 MHz, DMSO-d$_6$) δ 165.9, 160.4, 156.8, 153.6, 150.1, 148.6, 143.1, 133.6, 133.6, 130.4, 130.3, 122.6, 116.0, 115.7, 115.2, 110.4, 46.6, 42.3, 41.6, 41.2; MS (ES+) m/z 406.0.

Example 15.3

Synthesis of 2-(3-(4-fluorobenzyl)-2-oxoimidazolidin-1-yl)-N-(pyridin-2-ylmethyl)isonicotinamide dihydrochloride

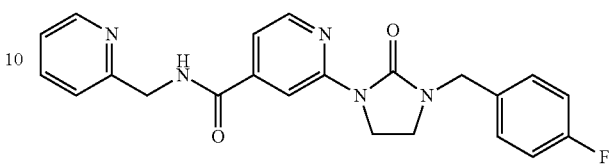

Following the procedure as described in Example 15, making variations as required to replace benzylamine with pyridin-2-ylmethanamine to react with methyl 2-(3-(4-fluorobenzyl)-2-oxoimidazolidin-1-yl)isonicotinate, 2-(3-(4-fluorobenzyl)-2-oxoimidazolidin-1-yl)-N-(pyridin-2-ylmethyl)isonicotinamide dihydrochloride was obtained as a colorless solid in 45% yield: mp 141-143° C.; $^1$H NMR (300 MHz, DMSO-d$_6$) δ 9.71 (t, J=5.4 Hz, 1H), 8.81 (d, J=5.4 Hz, 1H), 8.69 (s, 1H), 8.56-8.41 (m, 2H), 7.99-7.87 (m, 2H), 7.49-7.47 (m, 1H), 7.35-7.26 (m, 2H), 7.18-7.23 (m, 2H), 4.83 (d, J=5.4 Hz, 2H), 4.39 (s, 2H), 3.95 (t, J=7.5 Hz, 2H), 3.36 (t, J=7.8 Hz, 2H); MS (ES+) m/z 406.2 (M+1).

Example 15.4

Synthesis of N-(4-fluorobenzyl)-2-(3-(4-fluorobenzyl)-2-oxoimidazolidin-1-yl)isonicotinamide

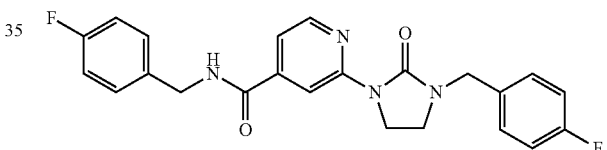

Following the procedure as described in Example 15, making variations as required to replace benzylamine with 4-fluorobenzylamine ethanamine to react with methyl 2-(3-(4-fluorobenzyl)-2-oxoimidazolidin-1-yl)isonicotinate, N-(4-fluorobenzyl)-2-(3-(4-fluorobenzyl)-2-oxoimidazolidin-1-yl)isonicotinamide was obtained as a colorless solid in 50% yield: mp 173-175° C.; $^1$H NMR (300 MHz, CDCl$_3$) δ 8.57 (s, 1H), 8.35 (d, J=5.1 Hz, 1H), 7.41-7.39 (m, 1H), 7.31-7.21 (m, 4H), 7.04-6.96 (m, 4H), 6.84 (br s, 1H), 4.57 (d, J=5.7 Hz, 2H), 4.40 (s, 2H), 4.03 (t, J=8.1 Hz, 2H), 3.36 (t, J=8.1 Hz, 2H); MS (ES+) m/z 423.2 (M+1).

Example 15.5

Synthesis of N-(cyclopropylmethyl)-2-(3-(4-fluorobenzyl)-2-oxoimidazolidin-1-yl)isonicotinamide

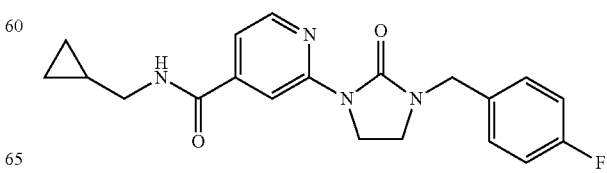

Following the procedure as described in Example 15, making variations as required to replace benzylamine with cyclopropylmethanamine to react with methyl 2-(3-(4-fluorobenzyl)-2-oxoimidazolidin-1-yl)isonicotinate, N-(cyclopropylmethyl)-2-(3-(4-fluorobenzyl)-2-oxoimidazolidin-1-yl)isonicotinamide was obtained as a colorless solid in 54% yield: mp 135-137° C.; $^1$H NMR (300 MHz, CDCl$_3$) δ 8.57 (s, 1H), 8.35 (d, J=5.1 Hz, 1H), 7.38 (d, J=5.1 Hz, 1H), 7.29-7.24 (m, 2H), 7.05-6.99 (m, 2H), 6.50 (br s, 1H), 4.45 (s, 2H), 4.07-4.02 (m, 2H), 3.46-3.26 (m, 4H), 1.08-0.97 (m, 1H), 0.56-0.50 (m, 2H), 0.28-0.23 (m, 2H); MS (ES+) m/z 369.2 (M+1).

Example 15.6

Synthesis of 2-(3-(cyclopropylmethyl)-2-oxoimidazolidin-1-yl)-N-(4-fluorobenzyl)isonicotinamide

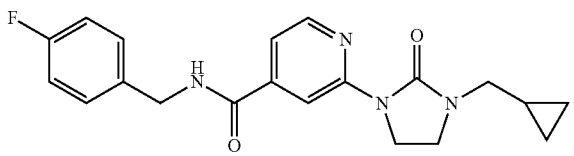 [SMILES: O=C(NCc1ccc(F)cc1)c1ccnc(N2CCN(CC3CC3)C2=O)c1]

Following the procedure as described in Example 15, making variations as required to replace benzylamine with 4-fluorobenzylamine to react with methyl 2-(3-(cyclopropylmethyl)-2-oxoimidazolidin-1-yl)isonicotinate, 2-(3-(cyclopropylmethyl)-2-oxoimidazolidin-1-yl)-N-(4-fluorobenzyl)isonicotinamide was obtained as a colorless solid in 77% yield: mp 150-151° C.; $^1$H NMR (300 MHz, CDCl$_3$) δ 8.53 (s, 1H), 8.34 (d, J=5.4 Hz, 1H), 7.39 (d, J=5.4 Hz, 1H), 7.30-7.24 (m, 2H), 7.01-6.91 (m, 3H), 4.55 (d, J=5.7 Hz, 2H), 4.06 (t, J=8.1 Hz, 2H), 3.59 (t, J=8.1 Hz, 2H), 3.13 (d, J=7.2 Hz, 2H), 99-0.85 (m, 1H), 0.59-0.51 (m, 2H), 0.24-0.19 (m, 2H); $^{13}$C NMR (75 MHz, CDCl$_3$) δ 165.7, 163.9, 160.6, 156.9, 153.1, 148.0, 133.6, 133.6, 129.8, 129.7, 115.9, 115.7, 115.4, 108.9, 48.6, 43.4, 41.6, 41.5, 9.0, 3.4; MS (ES+) m/z 369.3 (M+1).

Example 15.7

Synthesis of N-(2-cyclopropylethyl)-2-(3-(4-fluorobenzyl)-2-oxoimidazolidin-1-yl)isonicotinamide

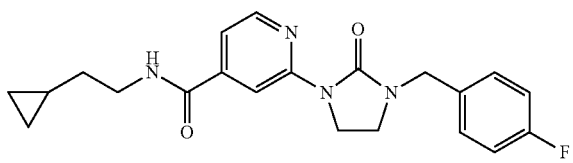 [SMILES: O=C(NCCC1CC1)c1ccnc(N2CCN(Cc3ccc(F)cc3)C2=O)c1]

Following the procedure as described in Example 15, making variations as required to replace benzylamine with 2-cyclopropylethanamine to react with methyl 2-(3-(4-fluorobenzyl)-2-oxoimidazolidin-1-yl)isonicotinate, N-(2-cyclopropylethyl)-2-(3-(4-fluorobenzyl)-2-oxoimidazolidin-1-yl)isonicotinamide was obtained as a colorless solid in 70% yield: mp 123-125° C.; $^1$H NMR (300 MHz, CDCl$_3$) δ 8.56 (s, 1H), 8.35 (d, J=5.1 Hz, 1H), 7.38 (dd, J=5.1, 1.2 Hz, 1H), 7.29-7.24 (m, 2H), 7.05-7.00 (m, 2H), 6.52 (br s, 1H), 4.44 (s, 2H), 4.05 (t, J=8.1 Hz, 2H), 3.55-3.49 (m, 2H), 3.37 (t, J=8.1 Hz, 2H), 1.54-1.47 (m, 2H), 0.77-0.64 (m, 1H), 0.53-0.45 (m, 2H), 0.11-0.02 (m, 2H); MS (ES+) m/z 383.3 (M+1).

Example 15.8

Synthesis of N-benzyl-2-(3-(cyclopropylmethyl)-2-oxoimidazolidin-1-yl)isonicotinamide

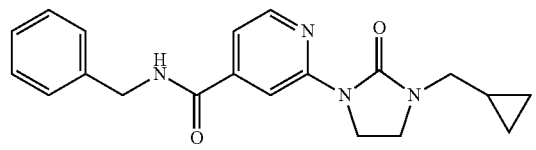 [SMILES: O=C(NCc1ccccc1)c1ccnc(N2CCN(CC3CC3)C2=O)c1]

Following the procedure as described in Example 15, making variations as required to replace methyl 2-(3-(4-fluorobenzyl)-2-oxoimidazolidin-1-yl)isonicotinate with methyl 2-(3-(cyclopropylmethyl)-2-oxoimidazolidin-1-yl)isonicotinate to react with benzylamine, N-benzyl-2-(3-(cyclopropylmethyl)-2-oxoimidazolidin-1-yl)isonicotinamide was obtained as a colorless solid in 31% yield: mp 121-123° C.; $^1$H NMR (300 MHz, CDCl$_3$) δ 8.54 (s, 1H), 8.36 (d, J=5.4 Hz, 1H), 7.40 (d, J=5.1 Hz, 1H), 7.32-7.24 (m, 5H), 6.73 (br s, 1H), 4.60 (d, J=6.0 Hz, 2H), 4.06 (t, J=8.1 Hz, 2H), 3.59 (t, J=8.1 Hz, 2H), 3.14 (d, J=6.9 Hz, 2H), 1.00-0.87 (m, 1H), 0.57-0.51 (m, 2H), 0.24-0.19 (m, 2H); $^{13}$C NMR (75 MHz, CDCl$_3$) δ 165.7, 156.9, 153.2, 148.2, 142.9, 137.7, 128.8, 128.0, 127.7, 115.9, 108.8, 48.6, 44.2, 41.6, 41.5, 31.0, 9.0, 3.4; MS (ES+) m/z 351.3 (M+1).

Example 15.9

Synthesis of 2-(3-(cyclopropylmethyl)-2-oxoimidazolidin-1-yl)-N-(pyridin-3-ylmethyl)isonicotinamide

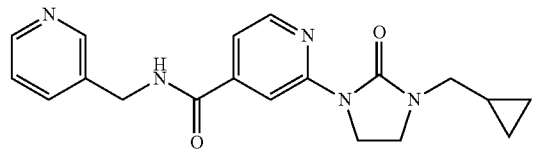 [SMILES: O=C(NCc1cccnc1)c1ccnc(N2CCN(CC3CC3)C2=O)c1]

Following the procedure as described in Example 15, making variations as required to replace methyl 2-(3-(4-fluorobenzyl)-2-oxoimidazolidin-1-yl)isonicotinate with methyl 2-(3-(cyclopropylmethyl)-2-oxoimidazolidin-1-yl)isonicotinate to react with pyridin-3-ylmethanamine, 2-(3-(cyclopropylmethyl)-2-oxoimidazolidin-1-yl)-N-(pyridin-3-ylmethyl)isonicotinamide was obtained as a colorless solid in 46% yield: mp 122-123° C.; $^1$H NMR (300 MHz, DMSO-d$_6$) δ 9.28 (t, J=9.0 Hz, 1H), 8.54-8.50 (m, 2H), 8.43-8.41 (m, 1H), 8.36 (d, J=3.0 Hz, 1H), 7.70-7.67 (m, 1H), 7.35-7.29 (m, 2H), 4.45 (d, J=5.7 Hz, 2H), 3.93 (t, J=9.0 Hz, 2H), 3.56 (t, J=9.0 Hz, 2H), 3.06 (d, J=9.0 Hz, 2H), 0.96-0.85 (m, 1H), 0.48-0.42 (m, 2H), 0.21-0.15 (m, 2H); MS (ES+) m/z 352.2 (M+1).

Example 15.10

Synthesis of 2-(3-(cyclopropylmethyl)-2-oxoimidazolidin-1-yl)-N-(pyridin-2-ylmethyl)isonicotinamide

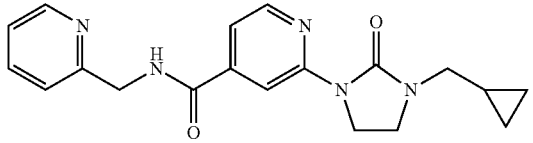 [SMILES: O=C(NCc1ccccn1)c1ccnc(N2CCN(CC3CC3)C2=O)c1]

Following the procedure as described in Example 15, making variations as required to replace methyl 2-(3-(4-fluorobenzyl)-2-oxoimidazolidin-1-yl)isonicotinate with methyl 2-(3-(cyclopropylmethyl)-2-oxoimidazolidin-1-yl)isonicotinate to react with pyridin-2-ylmethanamine, 2-(3-(cyclopropylmethyl)-2-oxoimidazolidin-1-yl)-N-(pyridin-2-ylmethyl)isonicotinamide was obtained as a colorless solid in 71% yield: mp 122-123° C.; $^1$H NMR (300 MHz, CDCl$_3$) δ 8.64 (s, 1H), 8.53 (d, J=5.1 Hz, 1H), 8.34 (d, J=5.1 Hz, 1H), 7.77-7.63 (m, 2H), 7.43-7.34 (m, 2H), 7.23-7.18 (m, 1H), 4.74 (d, J=5.1 Hz, 2H), 4.05 (t, J=8.1 Hz, 2H), 3.59 (t, J=8.1 Hz, 2H), 3.16 (d, J=7.2 Hz, 2H), 1.00-0.87 (m, 1H), 0.57-0.50 (m, 2H), 0.25-0.20 (m, 2H); $^{13}$C NMR (75 MHz, CDCl$_3$) δ 166.1, 156.9, 155.7, 153.3, 148.4, 148.2, 142.9, 137.6, 122.7, 122.6, 115.5, 109.5, 48.6, 44.5, 41.6, 41.5, 9.1, 3.4; MS (ES+) m/z 352.3 (M+1).

Example 15.11

Synthesis of 2-(3-(cyclopropylmethyl)-2-oxoimidazolidin-1-yl)-N-(pyridin-4-ylmethyl)isonicotinamide

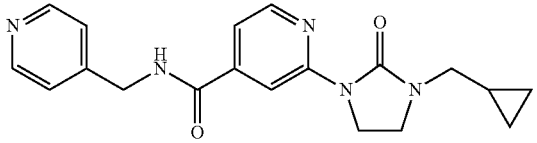 [SMILES: O=C(NCc1ccncc1)c1ccnc(N2CCN(CC3CC3)C2=O)c1]

Following the procedure as described in Example 15, making variations as required to replace methyl 2-(3-(4-fluorobenzyl)-2-oxoimidazolidin-1-yl)isonicotinate with methyl 2-(3-(cyclopropylmethyl)-2-oxoimidazolidin-1-yl)isonicotinate to react with pyridin-4-ylmethanamine, 2-(3-(cyclopropylmethyl)-2-oxoimidazolidin-1-yl)-N-(pyridin-4-ylmethyl)isonicotinamide was obtained as a colorless solid in 60% yield: mp 160-162° C.; $^1$H NMR (300 MHz, DMSO-d$_6$) δ 8.7-8.52 (m, 3H), 8.37 (d, J=5.1 Hz, 1H), 7.39 (d, J=5.1 Hz, 1H), 7.31-7.15 (m, 3H), 4.60 (d, J=4.5 Hz, 2H), 4.06 (t, J=8.1 Hz, 2H), 3.59 (t, J=8.1 Hz, 2H), 3.13 (d, J=6.9 Hz, 2H), 0.99-0.91 (m, 1H), 0.60-0.49 (m, 2H), 0.29-0.15 (m, 2H); $^{13}$C NMR (75 MHz, DMSO-d$_6$) δ 166.2, 156.9, 153.2, 149.8, 148.5, 147.3, 142.2, 122.5, 115.8, 108.8, 48.6, 42.8, 41.6, 41.5, 9.0, 3.4; MS (ES+) m/z 352.3 (M+1).

Example 15.12

Synthesis of 2-(3-(cyclopropylmethyl)-2-oxoimidazolidin-1-yl)-N-(3,4-difluorobenzyl)isonicotinamide

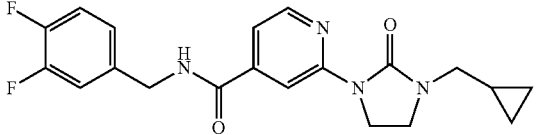 [SMILES: O=C(NCc1ccc(F)c(F)c1)c1ccnc(N2CCN(CC3CC3)C2=O)c1]

Following the procedure as described in Example 15, making variations as required to replace methyl 2-(3-(4-fluorobenzyl)-2-oxoimidazolidin-1-yl)isonicotinate with methyl 2-(3-(cyclopropylmethyl)-2-oxoimidazolidin-1-yl)isonicotinate to react with 3,4-difluorobenzylamine, 2-(3-(cyclopropylmethyl)-2-oxoimidazolidin-1-yl)-N-(3,4-difluorobenzyl)isonicotinamide was obtained as a colorless solid in 49% yield: mp 134-136° C.; $^1$H NMR (300 MHz, CDCl$_3$) δ 8.54 (s, 1H), 8.36 (d, J=5.1 Hz, 1H), 7.41-7.39 (m, 1H), 7.17-7.00 (m, 4H), 4.54 (d, J=6.0 Hz, 2H), 4.07 (t, J=8.1 Hz, 2H), 3.60 (t, J=8.1 Hz, 2H), 3.14 (d, J=7.2 Hz, 2H), 1.00-0.87 (m, 1H), 0.58-0.52 (m, 2H), 0.24-0.19 (m, 2H); MS (ES+) m/z 387.3 (M+1).

Example 15.13

Synthesis of N-benzyl-2-(1-(cyclopropylmethyl)-5-oxo-1H-1,2,4-triazol-4(5H)-yl)isonicotinamide

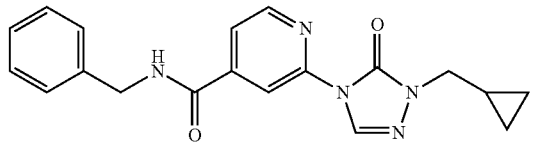 [SMILES: O=C(NCc1ccccc1)c1ccnc(-n2cnn(CC3CC3)c2=O)c1]

Following the procedure as described in Example 15, making variations as required to replace methyl 2-(3-(4-fluorobenzyl)-2-oxoimidazolidin-1-yl)isonicotinate and with methyl 2-(1-(cyclopropylmethyl)-5-oxo-1H-1,2,4-triazol-4(5H)-yl)isonicotinate to react with benzylamine, N-benzyl-2-(1-(cyclopropylmethyl)-5-oxo-1H-1,2,4-triazol-4(5H)-yl)isonicotinamide was obtained as a colorless solid in 38% yield: mp 137-139° C.; $^1$H NMR (300 MHz, CDCl$_3$) δ 8.58 (s, 1H), 8.51 (d, J=5.1 Hz, 1H), 8.43 (s, 1H), 7.74-7.72 (m, 1H), 7.36-7.23 (m, 5H), 6.85 (br s, 1H), 4.62 (d, J=5.7 Hz, 2H), 3.69 (d, J=6.9 Hz, 2H), 1.29-1.16 (m, 1H), 0.59-0.53 (m, 2H), 0.40-0.35 (m, 2H); $^{13}$C NMR (75 MHz, CDCl$_3$) δ 164.5, 151.2, 149.3, 147.9, 144.6, 137.3, 132.2, 128.9, 128.1, 127.9, 120.7, 109.3, 50.2, 44.4, 10.2, 3.6; MS (ES+) m/z 350.3 (M+1).

Example 15.14

Synthesis of N-(3,4-difluorobenzyl)-2-(3-(4-fluorobenzyl)-2-oxoimidazolidin-1-yl)isonicotinamide

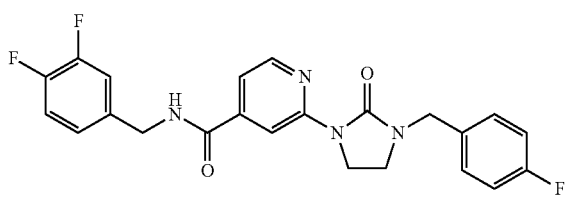 [SMILES: O=C(NCc1ccc(F)c(F)c1)c1ccnc(N2CCN(Cc3ccc(F)cc3)C2=O)c1]

Following the procedure as described in Example 15, making variations as required to replace benzylamine with 3,4-difluorobenzylamine to react with methyl 2-(3-(4-fluorobenzyl)-2-oxoimidazolidin-1-yl)isonicotinate, N-(3,4-difluorobenzyl)-2-(3-(4-fluorobenzyl)-2-oxoimidazolidin-1-yl)isonicotinamide was obtained as a colorless solid in 34% yield: mp 182-183° C.; $^1$H NMR (300 MHz, CDCl$_3$) δ 8.57 (s, 1H), 8.37 (d, J=5.1 Hz, 1H), 7.24-6.99 (m, 9H), 4.55 (d, J=5.7 Hz, 2H), 4.42 (s, 2H), 4.04 (t, J=8.1 Hz, 2H), 3.37 (t, J=8.1 Hz, 2H); $^{13}$C NMR (75 MHz, CDCl$_3$) δ 165.7, 157.0, 153.0, 148.4, 142.6, 131.9, 129.9, 129.7, 123.9, 117.6, 117.4, 117.0, 116.8, 116.1, 115.9, 115.6, 108.9, 47.2, 43.1, 41.3, 41.1; MS (ES+) m/z 440.9 (M+1).

Example 15.15

Synthesis of N-(4-fluorobenzyl)-2-(2-oxo-3-(pyridin-2-ylmethyl)imidazolidin-1-yl)isonicotinamide

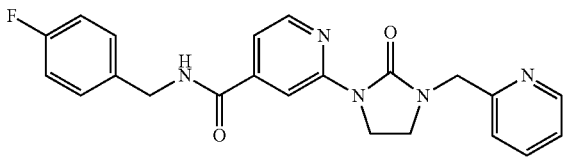 [SMILES: O=C(NCc1ccc(F)cc1)c1ccnc(N2CCN(Cc3ccccn3)C2=O)c1]

Following the procedure as described in Example 15, making variations as required to replace benzylamine with 4-fluorobenzylamine to react with methyl 2-(2-oxo-3-(pyridin-2-ylmethyl)imidazolidin-1-yl)isonicotinate, the title compound was obtained as a colorless solid in 52% yield: mp 141-142° C.; $^1$H NMR (300 MHz, CDCl$_3$) δ 8.56-8.53 (m, 2H), 8.35 (d, J=4.8 Hz, 1H), 7.68-6.86 (m, 9H), 4.57-4.54 (m, 4H), 4.06 (t, J=7.9 Hz, 2H), 3.53 (t, J=8.0 Hz, 2H); MS (ES+) m/z 405.7 (M+1).

Example 15.16

Synthesis of N-(4-fluorobenzyl)-2-(2-oxo-3-(pyridin-4-ylmethyl)imidazolidin-1-yl)isonicotinamide

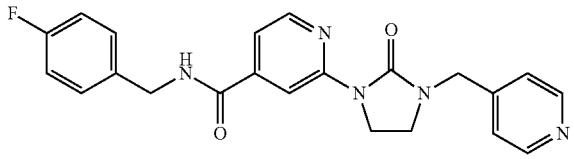 [SMILES: O=C(NCc1ccc(F)cc1)c1ccnc(N2CCN(Cc3ccncc3)C2=O)c1]

Following the procedure as described in Example 15, making variations as required to replace benzylamine with 4-fluorobenzylamine to react with methyl 2-(2-oxo-3-(pyridin-4-ylmethyl)imidazolidin-1-yl)isonicotinate, N-(4-fluorobenzyl)-2-(2-oxo-3-(pyridin-4-ylmethyl)imidazolidin-1-yl)isonicotinamide was obtained as a colorless solid in 48% yield: mp 161-163° C.; $^1$H NMR (300 MHz, CDCl$_3$) δ 8.67-8.50 (m, 3H), 8.37 (d, J=5.1 Hz, 1H), 7.49-7.20 (m, 5H), 7.02-6.96 (m, 2H), 6.84 (br s, 1H), 4.57 (d, J=5.7 Hz, 2H), 4.45 (s, 2H), 4.09 (t, J=8.1 Hz, 2H), 3.42 (t, J=8.1 Hz, 2H); MS (ES+) m/z 405.8 (M+1).

Example 15.17

Synthesis of N-(3,4-difluorobenzyl)-2-(2-oxo-3-(pyridin-3-ylmethyl)imidazolidin-1-yl)isonicotinamide

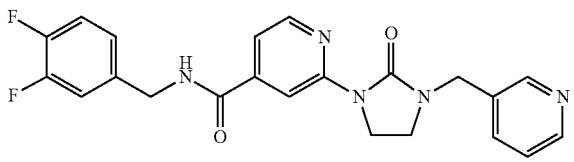 [SMILES: O=C(NCc1ccc(F)c(F)c1)c1ccnc(N2CCN(Cc3cccnc3)C2=O)c1]

Following the procedure as described in Example 15, making variations as required to replace benzylamine with 3,4-difluorobenzylamine to react with methyl 2-(2-oxo-3-(pyridin-3-ylmethyl)imidazolidin-1-yl)isonicotinate, N-(3,4-difluorobenzyl)-2-(2-oxo-3-(pyridin-3-ylmethyl)imidazolidin-1-yl)isonicotinamide was obtained as a colorless solid in 59% yield: mp 178-180° C.; $^1$H NMR (300 MHz, CDCl$_3$) δ 8.63-8.53 (m, 3H), 8.36 (dd, J=5.4, 0.6 Hz, 1H), 7.64-7.60 (m, 1H), 7.39 (dd, J=5.1, 1.5 Hz, 1H), 7.31-7.26 (m, 1H), 7.17-7.03 (m, 4H), 4.61 (d, J=6.6 Hz, 2H), 4.46 (s, 2H), 4.05 (t, J=8.1 Hz, 2H), 3.39 (t, J=8.1 Hz, 2H); $^{13}$C NMR (75 MHz, CDCl$_3$) δ 165.8, 157.0, 152.9, 149.5, 149.4, 148.5, 142.6, 135.8, 134.9, 131.9, 123.9, 123.8, 117.6, 117.4, 117.0, 116.8, 116.1, 108.9, 45.5, 43.1, 41.3, 41.2; MS (ES+) m/z 423.9 (M+1).

Example 15.18

Synthesis of N-(3,4-difluorobenzyl)-2-(2-oxo-3-(pyridin-2-ylmethyl) imidazolidin-1-yl)isonicotinamide

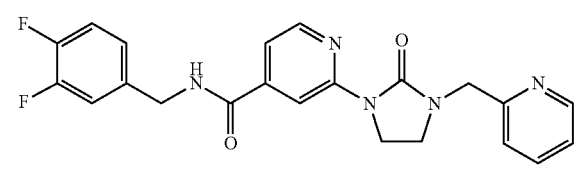 [SMILES: O=C(NCc1ccc(F)c(F)c1)c1ccnc(N2CCN(Cc3ccccn3)C2=O)c1]

Following the procedure as described in Example 15, making variations as required to replace benzylamine with 3,4-difluorobenzylamine to react with 2-(2-oxo-3-(pyridin-2-ylmethyl)imidazolidin-1-yl)isonicotinate, N-(3,4-difluorobenzyl)-2-(2-oxo-3-(pyridin-2-ylmethyl) imidazolidin-1-yl)isonicotinamide was obtained as a colorless solid in 61% yield: mp 143-145° C.; $^1$H NMR (300 MHz, CDCl$_3$) δ 8.64-8.53 (m, 2H), 8.36-8.35 (m, 1H), 7.68-7.63 (m, 1H), 7.40-7.38 (m, 1H), 7.29-7.02 (m, 6H), 4.57-4.52 (m, 4H), 4.06 (t, J=8.1 Hz, 2H), 3.53 (t, J=8.1 Hz, 2H); $^{13}$C NMR (75 MHz, CDCl$_3$) δ 165.8, 157.2, 156.3, 153.0, 149.5, 148.4, 142.5, 137.1, 134.9, 123.9, 122.7, 122.1, 117.6, 117.3, 117.0, 116.8, 116.0, 108.9, 49.5, 43.0, 41.8, 41.5; MS (ES+) m/z 423.9 (M+1).

Example 15.19

Synthesis of N-benzyl-2-(2-oxo-3-(pyridin-4-ylmethyl)imidazolidin-1-yl)isonicotinamide

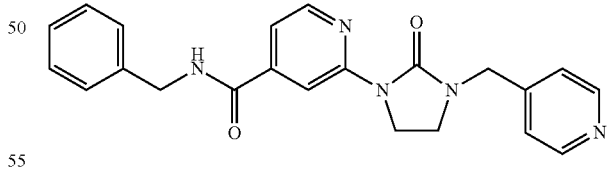

Following the procedure as described in Example 15, making variations as required to replace methyl 2-(3-(4-fluorobenzyl)-2-oxoimidazolidin-1-yl)isonicotinate with methyl 2-(2-oxo-3-(pyridin-4-ylmethyl)imidazolidin-1-yl)isonicotinate to react with benzylamine, N-benzyl-2-(2-oxo-3-(pyridin-4-ylmethyl)imidazolidin-1-yl)isonicotinamide was obtained as a colorless solid in 37% yield: mp 154-156° C.; $^1$H NMR (300 MHz, DMSO-d$_6$) δ 9.25 (t, J=5.9 Hz, 1H), 8.60 (s, 1H), 8.52-8.50 (m, 2H), 8.38 (d, J=5.4 Hz, 1H), 7.37-7.18 (m, 8H), 4.45-4.43 (m, 4H), 3.99 (t, J=7.9 Hz, 2H), 3.42 (t, J=7.9 Hz, 2H); MS (ES+) m/z 387.8 (M+1).

Example 15.20

Synthesis of 2-(3-(3,4-difluorobenzyl)-2-oxoimidazolidin-1-yl)-N-(4-fluorobenzyl)isonicotinamide

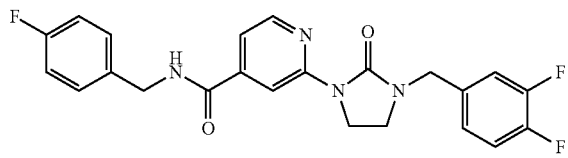 [SMILES: O=C(NCc1ccc(F)cc1)c1ccnc(N2CCN(Cc3ccc(F)c(F)c3)C2=O)c1]

Following the procedure as described in Example 15, making variations as required to replace methyl 2-(3-(4-fluorobenzyl)-2-oxoimidazolidin-1-yl)isonicotinate with methyl 2-(3-(3,4-difluorobenzyl)-2-oxoimidazolidin-1-yl)isonicotinate to react with 4-fluorobenzylamine, 2-(3-(3,4-difluorobenzyl)-2-oxoimidazolidin-1-yl)-N-(4-fluorobenzyl)isonicotinamide was obtained as a colorless solid in 40% yield: mp 165-167° C.; $^1$H NMR (300 MHz, CDCl$_3$) δ 8.62 (s, 1H), 8.37 (dd, J=5.1, 0.6 Hz, 1H), 7.41 (dd, J=5.4, 1.5 Hz, 1H), 7.37-7.26 (m, 2H), 7.13-6.97 (m, 5H), 6.80 (br s, 1H), 4.57 (d, J=5.7 Hz, 2H), 4.39 (s, 2H), 4.05 (t, J=8.1 Hz, 2H), 3.38 (t, J=8.1 Hz, 2H); MS (ES+) m/z 441.1 (M+1).

Example 15.21

Synthesis of 2-(3-((4-(difluoromethyl)phenyl)difluoromethyl)-2-oxoimidazolidin-1-yl)-N-(4-fluorobenzyl)isonicotinamide

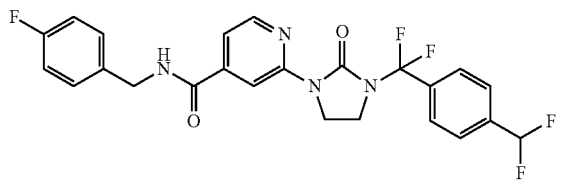 [SMILES: O=C(NCc1ccc(F)cc1)c1ccnc(N2CCN(C(F)(F)c3ccc(C(F)F)cc3)C2=O)c1]

Following the procedure as described in Example 15, making variations as required to replace methyl 2-(3-(4-fluorobenzyl)-2-oxoimidazolidin-1-yl)isonicotinate with methyl 2-(3-((4-(difluoromethyl)phenyl)difluoromethyl)-2-oxoimidazolidin-1-yl)isonicotinate to react with 4-fluorobenzylamine, 2-(3-((4-(difluoromethyl)phenyl)-difluoromethyl)-2-oxoimidazolidin-1-yl)-N-(4-fluorobenzyl)isonicotinamide was obtained as a colorless solid in 41% yield: mp 173-175° C.; $^1$H NMR (300 MHz, CDCl$_3$) δ 8.40 (d, J=5.1 Hz, 1H), 8.25 (s, 1H), 7.73 (d, J=8.1 Hz, 2H), 7.60 (d, J=7.8 Hz, 2H), 7.47 (dd, J=5.1, 0.9 Hz, 1H), 7.25-7.21 (m, 2H), 6.99-6.90 (m, 2H), 6.86-6.42 (m, 2H), 4.50 (d, J=5.7 Hz, 2H), 4.18 (t, J=7.8 Hz, 2H), 3.89 (t, J=7.8 Hz, 2H); MS (ES+) m/z 490.9 (M+1).

Example 15.22

Synthesis of 2-(3-(2,4-difluorobenzyl)-2-oxoimidazolidin-1-yl)-N-(4-fluorobenzyl)isonicotinamide

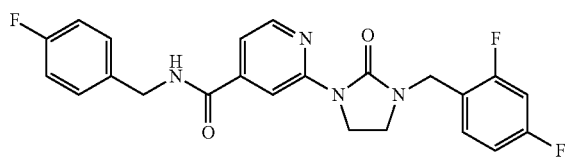 [SMILES: O=C(NCc1ccc(F)cc1)c1ccnc(N2CCN(Cc3ccc(F)cc3F)C2=O)c1]

Following the procedure as described in Example 15, making variations as required to replace methyl 2-(3-(4-fluorobenzyl)-2-oxoimidazolidin-1-yl)isonicotinate with methyl 2-(3-(2,4-difluorobenzyl)-2-oxoimidazolidin-1-yl)isonicotinate to react with 4-fluorobenzylamine, 2-(3-(2,4-difluorobenzyl)-2-oxoimidazolidin-1-yl)-N-(4-fluorobenzyl)isonicotinamide was obtained as a colorless solid in 55% yield: mp 171-173° C.; $^1$H NMR (300 MHz, CDCl$_3$) δ 8.61 (s, 1H), 8.36 (dd, J=5.1, 0.6 Hz, 1H), 7.56-7.27 (m, 4H), 7.07-6.97 (m, 2H), 6.92-6.74 (m, 3H), 4.58 (d, J=6.0 Hz, 2H), 4.48 (s, 2H), 4.04 (t, J=8.1 Hz, 2H), 3.43 (t, J=8.1 Hz, 2H); MS (ES+) m/z 441.1 (M+1).

Example 16

Synthesis of N-benzyl-2-(1-(4-fluorobenzyl)-5-oxo-1H-1,2,4-triazol-4(5H)-yl)isonicotinamide

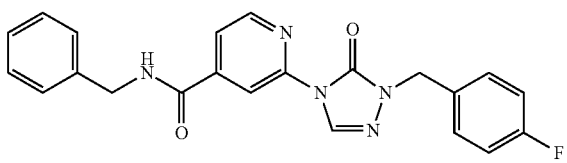 [SMILES: O=C(NCc1ccccc1)c1ccnc(-n2cnn(Cc3ccc(F)cc3)c2=O)c1]

A. To a solution of methyl 2-(5-oxo-1H-1,2,4-triazol-4(5H)-yl)isonicotinate (1.68 g, 7.63 mmol) in N,N-dimethylformamide (76 mL) was added sodium hydride (60% dispersion in mineral oil, 0.67 g, 16.80 mmol) at 0° C. The resulting reaction mixture was stirred for 1 hour at 0° C., followed by the addition of 1-(bromomethyl)-4-fluorobenzene (3.23 g, 17.09 mmol) dropwise. The reaction mixture was stirred at ambient temperature for 48 hours and concentrated in vacuo to dryness to give methyl 2-(1-(4-fluorobenzyl)-5-oxo-1H-1,2,4-triazol-4(5H)-yl)isonicotinate, and used in the further reaction without purification B. A solution of methyl 2-(1-(4-fluorobenzyl)-5-oxo-1H-1,2,4-triazol-4(5H)-yl)isonicotinate and sodium cyanide (0.80 g, 1.43 mmol) in benzylamine (50 mL) was stirred at 100° C. for 23 hours and at 110° C. for 3 hours and concentrated in vacuo. The residue was dissolved in ethyl acetate (30 mL), washed with water (20 mL) and brine (20 mL). The organic solution was dried over anhydrous sodium sulphate, filtered and concentrated in vacuo to dryness. The residue was purified by column chromatography eluting with ethyl acetate in dichloromethane (0% to 50%) to give N-benzyl-2-(1-(4-fluorobenzyl)-5-oxo-1H-1,2,4-triazol-4(5H)-yl)isonicotinamide as a colorless solid (0.29 g, 6%): mp 173-175° C.; $^1$H NMR (300 MHz, CDCl$_3$) δ 8.56-8.55 (m, 1H), 8.49 (dd, J=5.1, 0.6 Hz, 1H), 8.41 (s, 1H), 7.73-7.70 (m, 1H), 7.32-7.22 (m, 7H), 7.00-6.95 (m, 3H), 4.90 (s, 2H), 4.60 (d, J=5.7 Hz, 2H); MS (ES+) m/z 403.9.

Example 17

Synthesis of N-benzyl-2-(2-oxo-4-phenylpyridin-1(2H)-yl)isonicotinamide

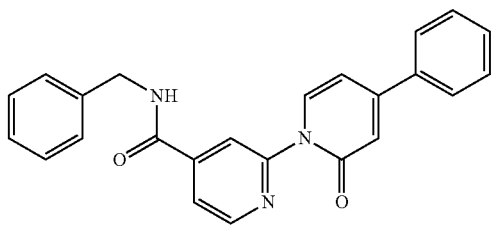 [SMILES: O=C(NCc1ccccc1)c1ccnc(-n2ccc(-c3ccccc3)cc2=O)c1]

A degassed mixture of N-benzyl-2-chloroisonicotinamide (0.25 g, 1.01 mmol), 4-phenylpyridin-2(1H)-one (0.17 g, 0.91 mmol), potassium carbonate (0.20 g, 1.44 mmol), 8-hydroxyquiniline (0.02 g, 0.14 mmol) and copper(I) iodide (0.03 g, 0.14 mmol) in N,N-dimethylformamide (3.0 mL) was heated at 130° C. for 18 hours. The resulting solution was cooled to ambient temperature, quenched with ammonium hydroxide solution (10 mL) and extracted with ethyl acetate (2×25 mL). The organic solution was dried over anhydrous sodium sulphate, filtered and concentrated in vacuo. The residue was purified by column chromatography to give N-benzyl-2-(2-oxo-4-phenylpyridin-1(2H)-yl)isonicotinamide as a colorless solid (0.10 g, 25%): mp 162-163° C.; $^1$H NMR (300 MHz, DMSO-$d_6$) δ 9.43 (t, J=5.1 Hz, 1H), 8.73 (d, J=5.1 Hz, 1H), 8.24, (s, 1H), 7.99 (d, J=7.3 Hz, 1H), 7.89 (d, J=5.1 Hz, 1H), 7.79-7.76 (m, 2H), 7.54-7.45 (m, 3H), 7.36-7.18 (m, 5H), 6.82 (s, 1H), 6.76 (d, J=7.3 Hz, 1H), 4.48 (d, J=5.7 Hz, 2H); $^{13}$C NMR (75 MHz, DMSO-$d_6$) δ 164.2, 161.6, 152.7, 152.0, 150.2, 143.6, 139.4, 137.4, 136.6, 130.5, 129.6, 128.8, 127.9, 127.4, 127.3, 121.6, 119.9, 116.8, 105.6, 43.3; MS (ES+) m/z 382.6 (M+1).

Example 18

Synthesis of 2-oxo-4-phenyl-3,4,5,6-tetrahydro-2H-[1,2']bipyridinyl-4'-carboxylic acid benzylamide

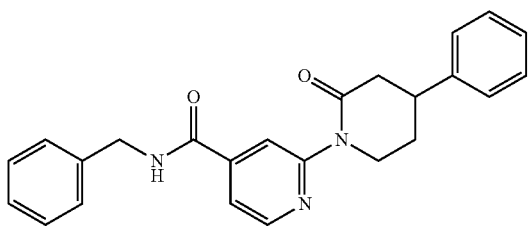 [SMILES: O=C(NCc1ccccc1)c1ccnc(N2CCC(c3ccccc3)CC2=O)c1]

A degassed mixture of N-benzyl-2-chloroisonicotinamide (0.05 g, 0.20 mmol), 4-phenylpiperidin-2-one (0.04 g, 0.22 mmol), cesium carbonate (0.20 g, 0.61 mmol) and 9,9-dimethyl-4,5-bis(diphenylphosphino)xanthene (0.005 g, 0.008 mmol), tris(dibenzylideneacetone)dipalladium (0.004 g, 0.004 mmol) in N,N-dimethylformamide (3.0 mL) was heated at 90° C. for 18 hours and cooled to ambient temperature. The resulting solution was diluted with ethyl acetate (30 mL), washed with water (20 mL) and brine (20 mL). The organic solution was dried over anhydrous sodium sulphate, filtered and concentrated in vacuo. The residue was purified by column chromatography to give 2-oxo-4-phenyl-3,4,5,6-tetrahydro-2H-[1,2']bipyridinyl-4'-carboxylic acid benzylamide as a colorless solid (0.06 g, 77%): mp 55-60° C.; $^1$H NMR (300 MHz, CDCl$_3$) δ 8.46 (d, J=5.1 Hz, 1H), 8.09 (s, 1H), 7.50 (d, J=5.1 Hz, 1H), 7.40-7.16 (m, 11H), 4.59-4.46 (m, 2H), 4.09-3.84 (m, 2H), 3.24-3.09 (m, 1H), 2.79 (dd, J=17.5, 5.3 Hz, 1H), 2.61 (dd, J=17.5, 11.2 Hz, 1H), 2.26-2.22 (m, 1H), 2.13-1.95 (m, 1H); $^{13}$C NMR (75 MHz, CDCl$_3$) δ 170.6, 165.1, 154.8, 148.7, 143.2, 142.9, 137.8, 128.9, 128.7, 128.1, 127.6, 127.0, 126.5, 119.0, 117.8, 47.4, 44.1, 40.8, 38.6, 30.3; MS (ES+) m/z 386.5 (M+1).

Example 19

Synthesis of 4-benzyloxy-2-oxo-2H-[1,2']bipyridinyl-4'-carboxylic acid benzylamide

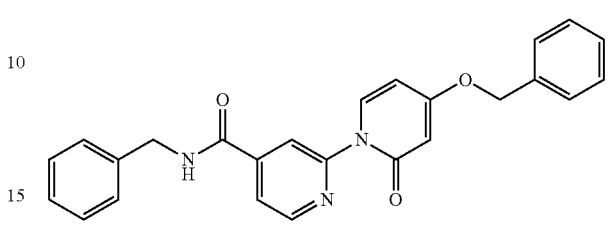

A mixture of N-benzyl-2-chloroisonicotinamide (1.00 g, 4.06 mmol), copper iodide(I) (0.12 g, 0.61 mmol), 8-hydroxyquinoline (0.09 g, 0.61 mmol), potassium carbonate (0.84 g, 6.09 mmol), 4-(benzyloxy)pyridin-2(1H)-one (0.82 g, 4.06 mmol) in N,N-dimethylormamide (20 mL) was heated to 110° C. for 16 hours under nitrogen atmosphere and concentrated in vacuo. The residue was dissolved in dichloromethane (100 mL), washed with water (100 mL), dried over anhydrous sodium sulphate, filtered and concentrated in vacuo to dryness. The residue was purified by column chromatography eluting with 60-75% ethyl acetate in petroleum ether to give 4-benzyloxy-2-oxo-2H-[1,2']bipyridinyl-4'-carboxylic acid benzylamide as colorless solid (0.89 g, 53%): mp 158-161° C. (dichloromethane/hexanes); $^1$H NMR (300 MHz, CDCl$_3$) δ 8.60 (d, J=5.0 Hz, 1H), 8.19 (s, 1H), 7.82 (d, J=7.9 Hz, 1H), 7.74 (d, J=5.0 Hz, 1H), 7.42-7.26 (m, 11H), 6.16-6.13 (m, 1H) 5.95 (d, J=2.3 Hz, 1H), 5.02 (s, 2H), 4.58 (d, J=5.6 Hz, 2H); MS (ES+) m/z 412.2 (M+1).

Example 20

Synthesis of 4-hydroxy-2-oxo-2H-[1,2']bipyridinyl-4'-carboxylic acid benzylamide

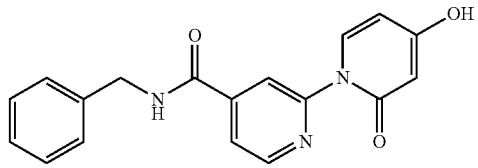 [SMILES: O=C(NCc1ccccc1)c1ccnc(-n2ccc(O)cc2=O)c1]

A solution of N-benzyl-2-(4-(benzyloxy)-2-oxopyridin-1 (2H)-yl)isonicotinamide (0.88 g, 2.14 mmol) and 20 weight % palladium on activated carbon (0.10 g) in methanol (50 mL) was stirred in atmospheric pressure of hydrogen for 2 hours. The resulting solution was filtered and concentrated in vacuo. The residue was recrystallized from methanol (10 mL) to give 4-hydroxy-2-oxo-2H-[1,2']bipyridinyl-4'-carboxylic acid benzylamide as a colorless solid (0.34 g, 50%): mp 102-105° C. (methanol); $^1$H NMR (300 MHz, CD$_3$OD) δ 8.66 (d, J=5.1 Hz, 1H), 8.05 (s, 1H), 7.81-7.78 (m, 2H), 7.36-7.24 (m, 5H), 6.20-6.17 (m, 1H), 5.86 (s, 1H) 4.57 (s, 2H); $^{13}$C NMR (75 MHz, CD$_3$OD) δ 167.6, 164.0, 162.9, 150.8, 147.9, 142.4, 136.5, 135.9, 126.6, 125.7, 125.4, 119.5, 117.9, 100.9, 96.8, 41.8; MS (ES+) m/z 322.3 (M+1).

Example 21

Synthesis of N-benzyl-2-(3-benzyl-2-oxopiperidin-1-yl)isonicotinamide

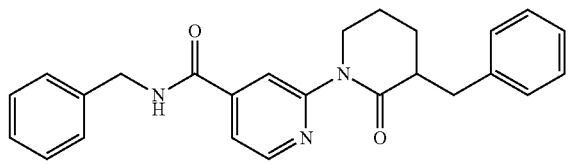 [SMILES: O=C(NCc1ccccc1)c1ccnc(N2CCCC(Cc3ccccc3)C2=O)c1]

To a solution of N-benzyl-2-(2-oxopiperidin-1-yl)isonicotinamide (0.14 g, 0.45 mmol) in anhydrous tetrahydrofuran (15 mL) was added a solution of lithium bis(trimethylsilyl)amide in tetrahydrofuran (0.52 mL, 0.45 mmol) at −78° C. under nitrogen atmosphere. The resulting solution was stirred for 30 minutes at −78° C., followed by the addition of a solution of benzyl bromide (0.15 g, 0.90 mmol) in anhydrous tetrahydrofuran (5 mL) dropwise at −78° C. The reaction mixture was warmed to ambient temperature, stirred for 2 hours, quenched with aqueous saturated ammonium chloride solution (10 mL) and extracted with dichloromethane (3×20 mL). The combined organic layers were dried over anhydrous sodium sulfate, filtered and concentrated in vacuo. The residue was purified by column chromatography eluted with 50-65% ethyl acetate in hexanes to give N-benzyl-2-(3-benzyl-2-oxopiperidin-1-yl)isonicotinamide as a colorless solid (0.06 g, 32%): $^1$H NMR (300 MHz, CD$_3$OD) δ 8.61 (d, J=6.1 Hz, 1H), 7.98 (s, 1H), 7.58 (d, J=6.2 Hz, 1H), 7.42-7.12 (m, 10H), 4.58 (d, J=4.1 Hz, 2H), 2.88-2.81 (m, 2H), 2.1-1.91 (m, 4H), 1.81-1.58 (m, 3H); MS (ES+) m/z 400.5 (M+1).

Example 22

Synthesis of 2-(3-(4-fluorobenzyl)-2-oxoimidazolidin-1-yl)isonicotinamide

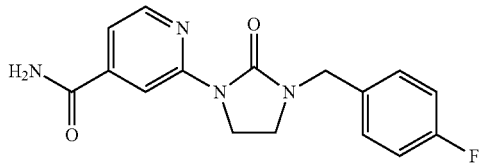 [SMILES: NC(=O)c1ccnc(N2CCN(Cc3ccc(F)cc3)C2=O)c1]

A solution of 2-(3-(4-fluorobenzyl)-2-oxoimidazolidin-1-yl)isonicotinic acid (0.35 g, 1.11 mmol), diisopropylethylamine (0.58 g, 4.44 mmol), 1-hydroxybenzotriazole monohydrate (0.30 g, 2.22 mmol) and O-(1H-benzotriazol-1-yl)-N,N,N',N'-tetramethyluronium tetrafluoroborate (0.71 g, 2.22 mmol) and ammonium chloride (0.36 g, 6.66 mmol) in tetrahydrofuran (10 mL) was stirred at ambient temperature for 23 hours and concentrated in vacuo. The residue was dissolved in dichloromethane, washed with saturated aqueous sodium bicarbonate solution (15 mL) and water (30 mL). The organic solution was dried over anhydrous sodium sulfate, filtered and concentrated in vacuo to give 2-(3-(4-fluorobenzyl)-2-oxoimidazolidin-1-yl)isonicotinamide as a colorless solid (0.14 g, 40%): mp 206-208° C.; $^1$H NMR (300 MHz, CDCl$_3$) δ 8.68 (s, 1H), 8.34 (d, 4.8 Hz, 1H), 8.13 (s, 1H), 7.62 (s, 1H), 7.33-7.13 (m, 5H), 4.38 (s, 2H), 3.92 (t, J=7.8 Hz, 2H), 3.34 (t, J=8.1 Hz, 2H); MS (ES+) m/z 314.9 (M+1).

Example 23

Synthesis of 2-(2-Oxo-3-(4-(trifluoromethyl)benzyl)imidazolidin-1-yl)-N-(thiazol-2-ylmethyl)isonicotinamide

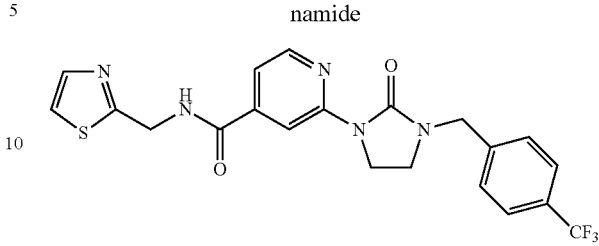

A mixture of 2-(2-oxo-3-(4-(trifluoromethyl)benzyl)imidazolidin-1-yl)isonicotinic acid (0.30 g, 1.11 mmol), diisopropylethylamine (0.85 mL, 6.75 mmol), 1-hydroxybenzotriazole monohydrate (0.28 g, 2.07 mmol) and O-(1H-benzotriazol-1-yl)-N,N,N',N'-tetramethyluronium tetrafluoroborate (0.58 g, 1.81 mmol) and thiazol-2-ylmethanamine (0.19 g, 1.67 mmol) in tetrahydrofuran (10 mL) was stirred at ambient temperature for 23 hours and concentrated in vacuo. The residue was suspended in a mixture of saturated sodium bicarbonate solution (10 mL) and ether (2.5 mL) and stirred at ambient temperature overnight. The solid was collected by filtration, washed with saturated sodium bicarbonate solution, water, ether, hexanes and dried in vacuo to afford 2-(2-oxo-3-(4-(trifluoromethyl)benzypimidazolidin-1-yl)-N-(thiazol-2-ylmethyl)-isonicotinamide as a colorless solid (0.21 g, 41%): mp 139-141° C.; $^1$H NMR (300 MHz, CDCl$_3$) δ 8.64 (s, 1H), 8.39 (d, J=5.2 Hz, 1H), 7.72 (d, J=3.3 Hz, 1H), 7.61 (d, J=8.1 Hz, 2H), 7.54 (br s, 1H), 7.43-7.41 (m, 3H), 7.30 (d, J=3.3 Hz, 1H), 4.95 (d, J=5.2 Hz, 2H), 4.53 (s, 2H), 4.10-4.05 (m, 2H), 3.43-3.38 (m, 2H); MS (ES+) m/z 461.9 (M+1).

Example 24

Synthesis of 2-(1-(3,4-Difluorobenzyl)-5-oxo-1H-1,2,4-triazol-4(5H)-yl)-N-((5-methylisoxazol-3-yl)methyl)-isonicotinamide

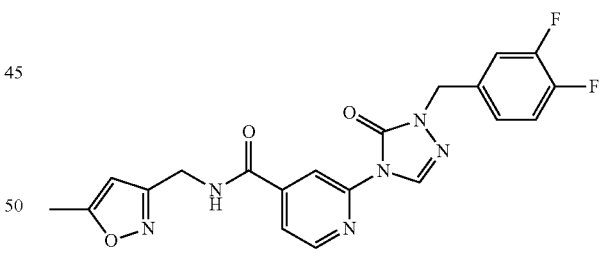

A mixture of 2-(1-(3,4-difluorobenzyl)-5-oxo-1H-1,2,4-triazol-4(5H)-yl)isonicotinic acid (0.22 g, 0.66 mmol), diisopropylethylamine (0.6 mL, 9.57 mmol), 1-hydroxybenzotriazole monohydrate (0.20 g, 1.44 mmol) and O-(1H-benzotriazol-1-yl)-N,N,N',N'-tetramethyluronium tetrafluoroborate (0.40 g, 1.24 mmol) and (5-methylisoxazol-3-yl)methanamine (0.19 g, 0.99 mmol) in tetrahydrofuran (10 mL) was stirred at ambient temperature for 23 hours and concentrated in vacuo. The residue was suspended in a mixture of saturated sodium bicarbonate solution (10 mL) and ether (2.5 mL) and stirred at ambient temperature overnight. The solid was collected by filtration, washed with saturated sodium bicarbonate solution, water, ether, hexanes and dried in vacuo to afford 2-(1-(3,4-difluorobenzyl)-5-oxo-1H-1,2,4-triazol-4(5H)-yl)-N-((5-methylisoxazol-3-yl)methyl)-isonicotinamide as a colorless solid (0.20 g, 71% yield): mp 160-161° C.; ¹H NMR (300 MHz, CDCl₃) δ 8.62 (s, 1H), 8.53 (d, J=5.7 Hz, 1H), 8.46 (s, 1H), 7.70 (dd, J=5.1, 1.4 Hz, 1H), 7.25-7.09 (m, 4H), 6.03 (s, 1H), 4.96 (s, 2H), 4.67 (d, J=5.7 Hz, 2H), 2.41 (s, 3H); MS (ES+) m/z 427.0 (M+1).

Example 25

Synthesis of 2-(3-(3,4-Difluorobenzyl)-2-oxoimidazolidin-1-yl)-N-(pyridin-2-ylmethyl)-isonicotinamide

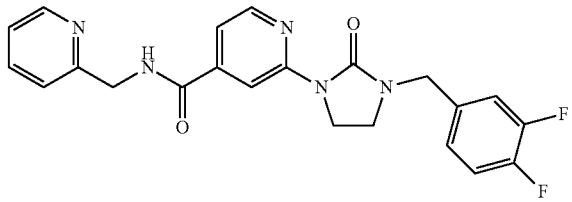 [SMILES: O=C(NCc1ccccn1)c1ccnc(N2CCN(Cc3ccc(F)c(F)c3)C2=O)c1]

A solution of methyl 2-(3-(3,4-difluorobenzyl)-2-oxoimidazolidin-1-yl)isonicotinate (0.25 g, 0.72 mmol) and sodium cyanide (0.10 g, 2.04 mmol) in pyridin-2-ylmethanamine (3.0 mL) was stirred at 95° C. for 16 hours and concentrated in vacuo. The residue was purified by column chromatography eluted with 0 to 90% of ethyl acetate in dichloromethane to give N-benzyl-2-(3-(4-fluorobenzyl)-2-oxoimidazolidin-1-yl)-isonicotinamide as a colorless solid (0.17 g, yield 54%): mp 99-101° C.; ¹H NMR (300 MHz, DMSO-d₆) δ 8.74 (t, J=6.0 Hz, 1H), 8.62 (s, 1H), 8.49-8.47 (m, 1H), 8.39 (d, J=5.1 Hz, 1H), 7.76-7.70 (m, 1H), 7.44-7.22 (m, 5H), 7.19-7.15 (m, 1H), 4.54 (d, J=6.0 Hz, 2H), 4.39 (s, 2H), 3.96 (t, J=8.1 Hz, 2H), 3.38 (t, J=8.1 Hz, 2H); MS (ES+) m/z 423.8 (M+1).

Example 26

The following compounds were prepared following the procedures as described in above reaction schemes and examples or known by one skilled in the art:

| | Structure | Chemical Name | Characterization Data |
|---|---|---|---|
| 26.1 | 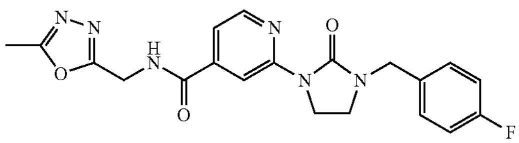 [SMILES: Cc1nnc(CNC(=O)c2ccnc(N3CCN(Cc4ccc(F)cc4)C3=O)c2)o1] | 2-(3-(4-Fluorobenzyl)-2-oxoimidazolidin-1-yl)-N-((5-methyl-1,3,4-oxadiazol-2-yl)methyl) isonicotinamide | mp 136-138° C.; ¹H NMR (300 MHz, CDCl₃) δ 8.56 (s, 1H), 8.33 (d, J = 5.4 Hz, 1H), 7.59 (br s, 1H), 7.36-7.22 (m, 3H), 7.03-6.97 (m, 2H), 4.81 (d, J = 5.4 Hz, 2H), 4.40 (s, 2H), 4.00 (t, J = 8.1 Hz, 2H), 3.35 (t, J = 8.1 Hz, 2H), 2.49 (s, 3H); MS (ES+) m/z 410.8 (M + 1). |
| 26.2 | 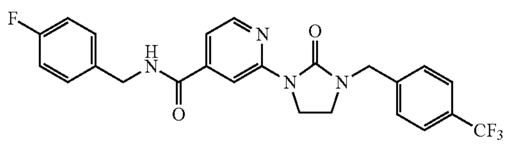 [SMILES: O=C(NCc1ccc(F)cc1)c1ccnc(N2CCN(Cc3ccc(C(F)(F)F)cc3)C2=O)c1] | N-(4-Fluorobenzyl)-2-(2-oxo-3-(4-(trifluoromethyl)benzyl)imidazolidin-1-yl)isonicotinamide | mp 168-170° C.; ¹H NMR (300 MHz, CDCl₃) δ 8.63 (s, 1H), 8.36 (d, J = 5.1 Hz, 1H), 7.60-7.54 (m, 2H), 7.46-7.22 (m, 5H), 7.09-6.91 (m, 2H), 6.81 (br s, 1H), 4.57 (d, J = 5.1 Hz, 2H), 4.49 (s, 2H), 4.06 (t, J = 8.1 Hz, 2H), 3.39 (t, J = 8.1 Hz, 2H); MS (ES+) m/z 473.0 (M + 1). |
| 26.3 | 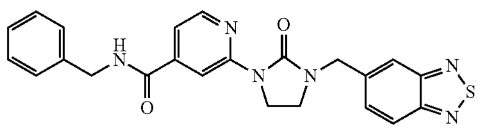 [SMILES: O=C(NCc1ccccc1)c1ccnc(N2CCN(Cc3ccc4nsnc4c3)C2=O)c1] | 2-(3-(Benzo[c][1,2,5]thiadiazol-5-ylmethyl)-2-oxoimidazolidin-1-yl)-N-benzylisonicotinamide | ¹H NMR (300 MHz, CDCl₃) δ 8.66 (s, 1H), 8.36 (d, J = 5.1 Hz, 1H), 7.96 (d, J = 9.0 Hz, 1H), 7.86 (s, 1H), 7.53 (dd, J = 9.0 Hz, 1.2 Hz, 1H), 7.43-7.17 (m, 6H), 6.77 (br s, 1H), 4.63-4.62 (m, 4H), 4.08 (t, J = 8.1 Hz, 2H), 3.44 (t, J = 8.1 Hz, 2H); MS (ES+) m/z 444.9 (M + 1). |
| 26.4 | 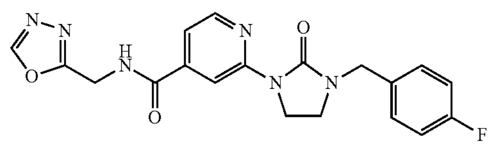 [SMILES: O=C(NCc1nnco1)c1ccnc(N2CCN(Cc3ccc(F)cc3)C2=O)c1] | N-((1,3,4-Oxadiazol-2-yl)methyl)-2-(3-(4-fluorobenzyl)-2-oxoimidazolidin-1-yl)isonicotinamide | mp 211-213° C.; ¹H NMR(300 MHz, DMSO-d₆) δ 10.96 (s, 1H), 8.42-8.40 (m, 1H), 8.33 (br s, 1H), 7.35-7.08 (m, 6H), 4.38 (s, 2H), 4.18 (s, 2H), 3.97-3.91 (m, 2H), 3.39-3.32 (m, 2H); MS (ES+) m/z 396.9 (M + 1). |
| 26.5 | 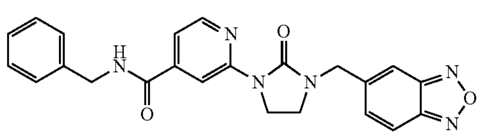 [SMILES: O=C(NCc1ccccc1)c1ccnc(N2CCN(Cc3ccc4nonc4c3)C2=O)c1] | 2-(3-(Benzo[c][1,2,5]oxadiazol-5-ylmethyl)-2-oxoimidazolidin-1-yl)-N-benzylisonicotinamide | mp 165-167° C.; ¹H NMR (300 MHz, CDCl₃) δ 8.62 (s, 1H), 8.36 (d, J = 5.1 Hz, 1H), 7.79 (d, J = 9.3 Hz, 1H), 7.66 (s, 1H), 7.42-7.21 (m, 7H), 6.81 (t, J = 5.0 Hz, 1H), 4.61 (d, J = 5.1 Hz, 2H), 4.50 (s, 2H), 4.09 (t, J = 8.1 Hz, 2H), 3.45 (t, J = 8.1 Hz, 2H); MS (ES+) m/z 428.8 (M + 1). |
| 26.6 | 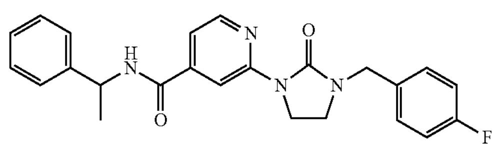 [SMILES: CC(NC(=O)c1ccnc(N2CCN(Cc3ccc(F)cc3)C2=O)c1)c1ccccc1] | 2-(3-(4-Fluorobenzyl)-2-oxoimidazolidin-1-yl)-N-(1-phenylethyl)isonicotinamide | mp 115-117° C.; ¹H NMR (300 MHz, CDCl₃) δ 8.57 (s, 1H), 8.34 (d, J = 5.1 Hz, 1H), 7.38-7.22 (m, 8H), 7.04-6.99 (m, 2H), 6.66 (d, J = 7.2 Hz, 1H), 5.36-5.27 (m, 1H), 4.42 (s, 2H), 4.03 (t, J = 8.1 Hz, 2H), 3.36 (t, J = 7.8 Hz, 2H), 1.59 (d, J = 6.9 Hz, 3H); MS (ES+) m/z 418.8 (M + 1). |

| | Structure | Chemical Name | Characterization Data |
|---|---|---|---|
| 26.7 | 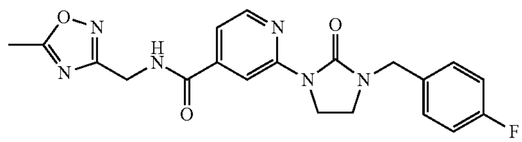 [SMILES: Cc1nc(CNC(=O)c2ccnc(N3CCN(Cc4ccc(F)cc4)C3=O)c2)no1] | 2-(3-(4-Fluorobenzyl)-2-oxoimidazolidin-1-yl)-N-((5-methyl-1,2,4-oxadiazol-3-yl)methyl)-isonicotinamide | mp 163-165° C.; $^1$H NMR (300 MHz, CDCl$_3$) δ 8.60 (s, 1H), 8.33 (d, J = 5.1 Hz, 1H), 7.38-7.19 (m, 4H), 7.04-6.98 (m, 2H), 4.73 ( d, J = 5.1 Hz, 2H), 4.42 (s, 2H), 4.01 (t, J = 8.1 Hz, 2H), 3.35 (t, J = 8.1 Hz, 2H), 2.55 (s, 3H); MS (ES+) m/z 410.7 (M + 1). |
| 26.8 | 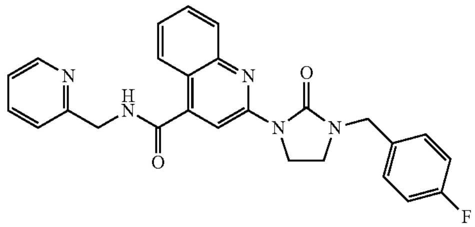 [SMILES: O=C(NCc1ccccn1)c1cc(N2CCN(Cc3ccc(F)cc3)C2=O)nc2ccccc12] | 2-(3-(4-Fluorobenzyl)-2-oxoimidazolidin-1-yl)-N-(pyridin-2-ylmethyl)quinoline-4-carboxamide | mp 161-163° C.; $^1$H NMR (300 MHz, CDCl$_3$) δ 8.78 (s, 1H), 8.51-8.49 (m, 1H), 8.19 (dd, J = 7.5, 0.9 Hz, 1H), 7.85-7.82 (m, 1H), 7.71-7.56 (m, 3H), 7.43-7.17 (m. 5H), 7.02-6.99 (m, 2H), 4.84 (d, J = 4.8 Hz, 2H), 4.41 (s, 2H), 4.17 (t, J = 8.1 Hz, 2H), 3.34 (t, J = 8.1 Hz, 2H); MS (ES+) m/z 455.9 (M + 1). |
| 26.9 | 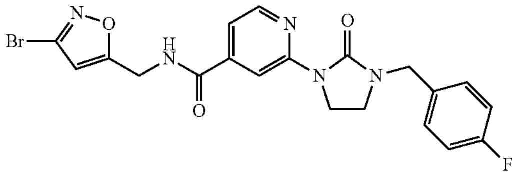 [SMILES: O=C(NCc1cc(Br)no1)c1ccnc(N2CCN(Cc3ccc(F)cc3)C2=O)c1] | N-((3-Bromoisoxazol-5-yl)methyl)-2-(3-(4-fluorobenzyl)-2-oxoimidazolidin-1-yl)isonicotinamide | mp 178-180° C.; $^1$H NMR (300 MHz, DMSO-d$_6$) δ 9.39 (t, J = 5.4 Hz, 1H), 8.60 (s, 1H), 8.39 (d, J = 5.1 Hz, 1H), 7.35-7.31 (m, 3H), 7.19-7.13 (m, 2H), 6.71 (s, 1H), 4.60 (d, J = 5.1 Hz, 2H), 4.39 (s, 2H), 3.94 (t, J = 8.1 Hz, 2H), 3.35 (t, J = 8.1 Hz, 2H); MS (ES+) m/z 475.6 (M + 1), 473.6 (M + 1). |
| 26.10 | 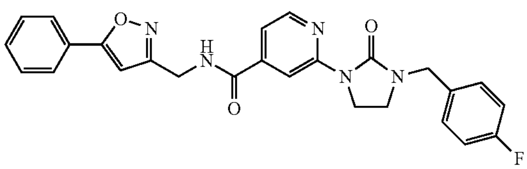 [SMILES: O=C(NCc1cc(-c2ccccc2)on1)c1ccnc(N2CCN(Cc3ccc(F)cc3)C2=O)c1] | 2-(3-(4-Fluorobenzyl)-2-oxoimidazolidin-1-yl)-N-((5-phenylisoxazol-3-yl)methyl)-isonicotinamide | mp 199-201° C.; $^1$H NMR (300 MHz, DMSO-d$_6$) δ 9.36 (t, J = 5.7 Hz, 1H), 8.70 (s, 1H), 8.39 (d, J = 5.1 Hz, 1H), 7.85-7.82 (m, 2H), 7.49-7.47 (m, 3H), 7.38-7.31 (m, 3H), 7.22-7.09 (m, 2H), 6.86 (s, 1H), 4.61 (d, J = 5.1 Hz, 2H), 4.39 (s, 2H), 3.94 (t, J = 8.1 Hz, 2H), 3.35 (t, J = 8.1 Hz, 2H); MS (ES+) m/z 471.9 (M + 1). |
| 26.11 | 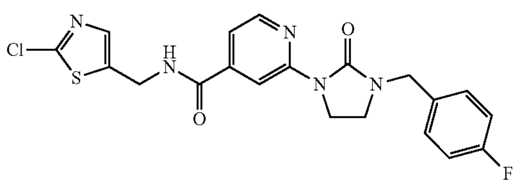 [SMILES: O=C(NCc1cnc(Cl)s1)c1ccnc(N2CCN(Cc3ccc(F)cc3)C2=O)c1] | N-((2-Chlorothiazol-5-yl)methyl)-2-(3-(4-fluorobenzyl)-2-oxoimidazolidin-1-yl)isonicotinamide | mp 185-186° C.; $^1$H NMR (300 MHz, DMSO-d$_6$) δ 9.45 (br s, 1H), 8.59 (s, 1H), 8.37 (d, J = 4.5 Hz, 1H), 7.65 (s, 1H), 7.32-7.13 (m, 5H), 4.56 (d, J = 4.5 Hz, 2H), 4.39 (s, 2H), 3.93 (t, J = 7.2 Hz, 2H), 3.34 (t, J = 7.2 Hz, 2H); MS (ES+) m/z 445.6 (M + 1), 447.5 (M + 1). |
| 26.12 | 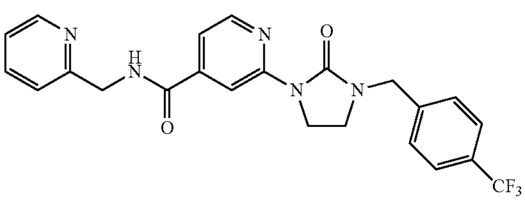 [SMILES: O=C(NCc1ccccn1)c1ccnc(N2CCN(Cc3ccc(C(F)(F)F)cc3)C2=O)c1] | 2-(2-Oxo-3-(4-(trifluoromethyl)benzyl)imidazolidin-1-yl)-N-(pyridin-2-ylmethyl)-isonicotinamide | mp 161-163° C.; $^1$H NMR (300 MHz, CDCl$_3$) δ 8.75 (s, 1H), 8.55 (d, J = 4.5 Hz, 1H), 8.37 (d, J = 5.1 Hz, 1H), 7.69-7.61 (m, 4H), 7.43-7.38 (m, 3H), 7.30 (d, J = 7.8 Hz, 1H), 7.21-7.17 (m, 1H), 4.74 (d, J = 5.1 Hz, 2H), 4.53 (s, 2H), 4.07 (t, J = 8.1 Hz, 2H), 3.39 (t, J = 8.1 Hz, 2H); MS (ES+) m/z 455.9 (M + 1). |
| 26.13 | 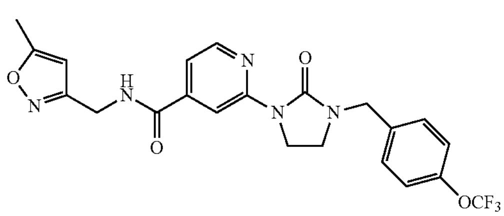 [SMILES: Cc1cc(CNC(=O)c2ccnc(N3CCN(Cc4ccc(OC(F)(F)F)cc4)C3=O)c2)no1] | N-((5-Methylisoxazol-3-yl)methyl)-2-(2-oxo-3-(4-(trifluoromethoxy)-benzyl)imidazolidin-1-yl)isonicotinamide | mp 129-130° C.; $^1$H NMR (300 MHz, CDCl$_3$) δ 8.59 (s, 1H), 8.35 (d, J = 5.4 Hz, 1H), 7.36-7.30 (m, 3H), 7.19-7.07 (m, 3H), 6.01 (s, 1H), 4.63 (d, J = 5.4 Hz, 2H), 4.45 (s, 2H), 4.04 (t, J = 7.8 Hz, 2H), 3.38 (t, J = 7.8 Hz, 2H), 2.37 (s, 3H); MS (ES+) m/z 475.9 (M + 1). |

| | Structure | Chemical Name | Characterization Data |
|---|---|---|---|
| 26.14 | 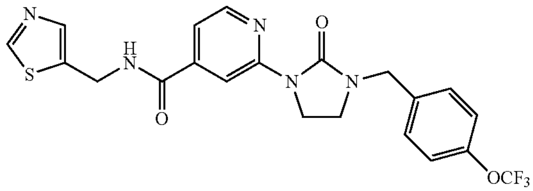 [SMILES: O=C(NCc1cncs1)c1ccnc(N2CCN(Cc3ccc(OC(F)(F)F)cc3)C2=O)c1] | 2-(2-Oxo-3-(4-(trifluoromethoxy)benzyl)imidazolidin-1-yl)-N-(thiazol-5-ylmethyl)-isonicotinamide | mp 189-191° C.; $^1$H NMR (300 MHz, CDCl$_3$) δ 8.72 (s, 1H), 8.62 (s, 1H), 8.36 (d, J = 5.7 Hz, 1H), 7.79 (s, 1H), 7.40-7.28 (m, 3H), 7.18-7.04 (m, 3H), 4.81 (d, J = 5.7 Hz, 2H), 4.44 (s, 2H), 4.04 (t, J = 8.0 Hz, 2H), 3.39 (t, J = 8.0 Hz, 2H); MS (ES+) m/z 477.7 (M + 1). |
| 26.15 | 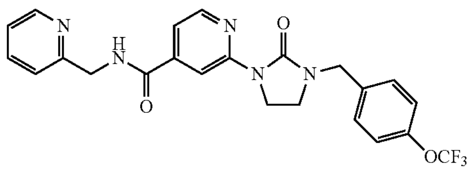 [SMILES: O=C(NCc1ccccn1)c1ccnc(N2CCN(Cc3ccc(OC(F)(F)F)cc3)C2=O)c1] | 2-(2-Oxo-3-(4-(trifluoromethoxy)benzyl)imidazolidin-1-yl)-N-(pyridin-2-ylmethyl)-isonicotinamide | mp 123-125° C.; $^1$H NMR (300 MHz, CDCl$_3$) δ 8.70 (s, 1H), 8.56 (d, J = 4.6 Hz, 1H), 8.38 (d, J = 5.2 Hz, 1H), 7.74-7.65 (m, 2H), 7.42-7.31 (m, 4H), 7.23-7.19 (m, 3H), 4.76 (d, J = 5.2 Hz, 2H), 4.49 (s, 2H), 4.10-4.05 (m, 2H), 3.43-3.38 (m, 2H); MS (ES+) m/z 472.0 (M + 1). |
| 26.16 | 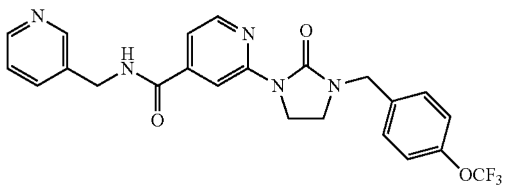 [SMILES: O=C(NCc1cccnc1)c1ccnc(N2CCN(Cc3ccc(OC(F)(F)F)cc3)C2=O)c1] | 2-(2-Oxo-3-(4-(trifluoromethoxy)-benzyl)imidazolidin-1-yl)-N-(pyridin-3-ylmethyl)-isonicotinamide | mp 185-187° C.; $^1$H NMR (300 MHz, CDCl$_3$) δ 8.64 (br s, 2H), 8.51 (d, J = 3.9 Hz, 1H), 8.37 (d, J = 5.4 Hz, 1H), 7.68 (d, J = 7.8 Hz, 1H), 7.41 (d, J = 5.1 Hz, 1H), 7.31-7.16 (m, 5H), 7.04 (br s, 1H), 4.62 (d, J = 5.4 Hz, 2H), 4.44 (s, 2H), 4.05 (t, J = 8.1 Hz, 2H), 3.39 (t, J = 8.1 Hz, 2H); MS (ES+) m/z 471.9 (M + 1). |
| 26.17 | 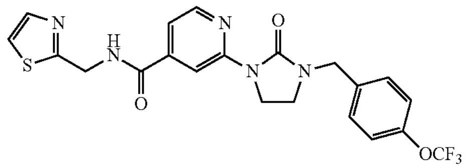 [SMILES: O=C(NCc1nccs1)c1ccnc(N2CCN(Cc3ccc(OC(F)(F)F)cc3)C2=O)c1] | 2-(2-Oxo-3-(4-(trifluoromethoxy)benzyl)imidazolidin-1-yl)-N-(thiazol-2-ylmethyl)-isonicotinamide | mp 97-99° C.; $^1$H NMR (300 MHz, CDCl$_3$) δ 8.70 (s, 1H), 8.37 (d, J = 5.4 Hz, 1H), 7.71 (d, J = 3.3 Hz, 1H), 7.41-7.28 (m, 5H), 7.20-7.17 (m, 2H), 4.94 (d, J = 5.4 Hz, 2H), 4.46 (s, 2H), 4.05 (t, J = 8.1 Hz, 2H), 3.39 (t, J = 8.1 Hz, 2H); MS (ES+) m/z 477.8 (M + 1). |
| 26.18 | 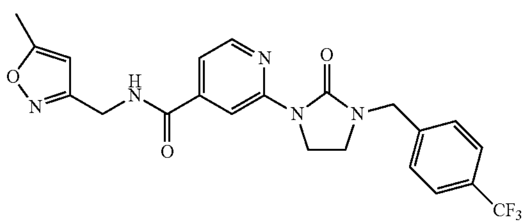 [SMILES: Cc1cc(CNC(=O)c2ccnc(N3CCN(Cc4ccc(C(F)(F)F)cc4)C3=O)c2)no1] | N-((5-Methylisoxazol-3-yl)methyl)-2-(2-oxo-3-(4-(trifluoromethyl)-benzyl)imidazolidin-1-yl)isonicotinamide | mp 153-155° C.; $^1$H NMR (300 MHz, CDCl$_3$) δ 8.59 (s, 1H), 8.36 (d, J = 5.4 Hz, 1H), 7.60-7.58 (m, 2H), 7.41-7.36 (m, 3H), 7.10 (s, 1H), 6.01 (s, 1H), 4.63 (d, J = 5.4 Hz, 2H), 4.51 (s, 2H), 4.06 (t, J = 8.0 Hz, 2H), 3.39 (t, J = 8.0 Hz, 2H), 2.37 (s, 3H); MS (ES+) m/z 459.8 (M + 1). |
| 26.19 | 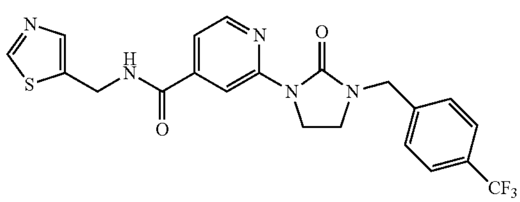 [SMILES: O=C(NCc1cncs1)c1ccnc(N2CCN(Cc3ccc(C(F)(F)F)cc3)C2=O)c1] | 2-(2-Oxo-3-(4-(trifluoromethyl)benzyl)imidazolidin-1-yl)-N-(thiazol-5-ylmethyl)-isonicotinamide | mp 163-165° C.; $^1$H NMR (300 MHz, CDCl$_3$) δ 8.70 (d, J = 6.9 Hz, 1H), 8.54 (d, J = 6.0 Hz, 1H), 8.35 (s, 1H), 7.81-7.77 (m, 1H), 7.60-7.58 (m, 2H), 7.40-7.38 (m, 3H), 7.18 (br s, 1H), 4.79 (d, J = 5.7 Hz, 2H), 4.49 (s, 2H), 4.06 (t, J = 7.8 Hz, 2H), 3.40 (t, J = 7.8 Hz, 2H); MS (ES+) m/z 461.8 (M + 1). |
| 26.20 | 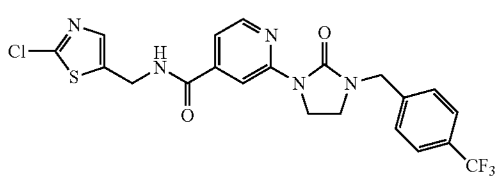 [SMILES: O=C(NCc1cnc(Cl)s1)c1ccnc(N2CCN(Cc3ccc(C(F)(F)F)cc3)C2=O)c1] | N-((2-Chlorothiazol-5-yl)methyl)-2-(2-oxo-3-(4-(trifluoromethyl)-benzyl)imidazolidin-1-yl)isonicotinamide | mp 209-211° C.; $^1$H NMR (300 MHz, CDCl$_3$) δ 8.55 (s, 1H), 8.40 (d, J = 5.2 Hz, 1H), 7.61 (d, J = 8.0 Hz, 2H), 7.45-7.40 (m, 4H), 7.26 (m, 1H), 4.69 (d, J = 5.9 Hz, 2H), 4.53 (s, 2H), 4.11-4.06 (m, 2H), 3.45-3.40 (m, 2H); MS (ES+) m/z 495.8 (M + 1), 497.7 (M + 1). |
| 26.21 | 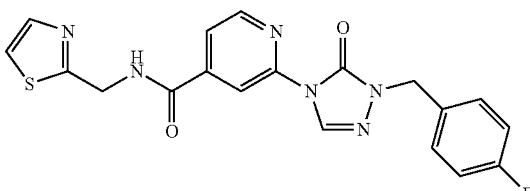 | 2-(1-(4-Fluorobenzyl)-5-oxo-1H-1,2,4-triazol-4(5H)-yl)-N-(thiazol-2-ylmethyl)-isonicotinamide | mp 170-172° C.; $^1$H NMR (300 MHz, DMSO-d$_6$) δ 9.79 (d, J = 3.9 Hz, 1H), 8.70-8.60 (m, 3H), 7.77-7.61 (m, 3H), 7.35-7.34 (m, 2H), 7.19-7.13 (m, 2H), 4.96 (d, J = 3.0 Hz, 2H), 4.76 (s, 2H); MS (ES+) m/z 410.8 (M + 1). |

| | Structure | Chemical Name | Characterization Data |
|---|---|---|---|
| 26.22 | 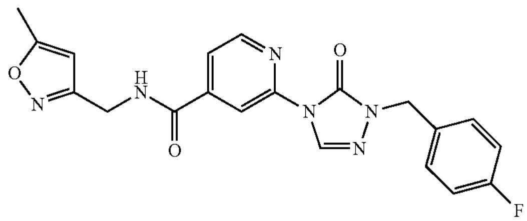 [SMILES: Cc1cc(CNC(=O)c2ccnc(-n3cnn(Cc4ccc(F)cc4)c3=O)c2)no1] | 2-(1-(4-Fluorobenzyl)-5-oxo-1H-1,2,4-triazol-4(5H)-yl)-N-((5-methylisoxazol-3-yl)methyl)-isonicotinamide | mp 198-200° C.; $^1$H NMR (300 MHz, DMSO-d$_6$) δ 9.47 (s, 1H), 8.69-8.56 (m, 3H), 7.73 (d, J = 4.8 Hz, 1H), 7.37-7.34 (m, 2H), 7.18-7.14 (m, 2H), 6.14 (s, 1H), 4.95 (br s, 2H), 4.46 (s, 2H), 2.33 (s, 3H); MS (ES+) m/z 408.8 (M + 1). |
| 26.23 | 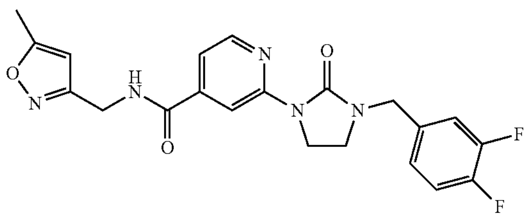 [SMILES: Cc1cc(CNC(=O)c2ccnc(N3CCN(Cc4ccc(F)c(F)c4)C3=O)c2)no1] | 2-(3-(3,4-Difluorobenzyl)-2-oxoimidazolidin-1-yl)-N-((5-methylisoxazol-3-yl)methyl)-isonicotinamide | mp 153-155° C.; $^1$H NMR (300 MHz, DMSO-d$_6$) δ 9.27 (s, 1H), 8.65 (s, 1H), 8.38 (d, J = 4.2 Hz, 1H), 7.37-7.33 (m, 3H), 7.15 (br s, 1H), 6.13 (s, 1H), 4.50-4.49 (m, 4H), 3.95 (t, J = 7.8 Hz, 2H), 3.38 (t, J = 7.8 Hz, 2H), 2.33 (s, 3H); MS (ES+) m/z 427.8 (M + 1). |
| 26.24 | 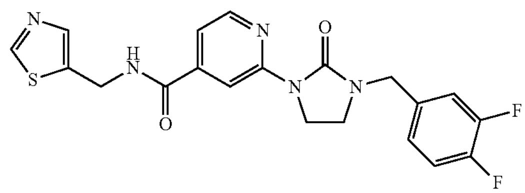 [SMILES: O=C(NCc1cncs1)c1ccnc(N2CCN(Cc3ccc(F)c(F)c3)C2=O)c1] | 2-(3-(3,4-Difluorobenzyl)-2-oxoimidazolidin-1-yl)-N-(thiazol-5-ylmethyl)-isonicotinamide | mp 111-113° C.; $^1$H NMR (300 MHz, DMSO-d$_6$) δ 9.39 (s, 1H), 8.95 (s, 1H), 8.58 (s, 1H), 8.37 (d, J = 5.4 Hz, 1H), 7.80 (s, 1H), 7.43-7.29 (m, 3H), 7.15 (br s, 1H), 4.65 (d, J = 5.4 Hz, 2H), 4.39 (s, 2H), 3.94 (t, J = 7.8 Hz, 2H), 3.37 (t, J = 7.8 Hz, 2H); MS (ES+) m/z 429.7 (M + 1). |
| 26.25 | 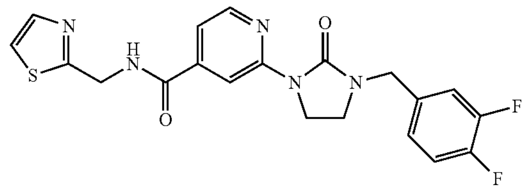 [SMILES: O=C(NCc1nccs1)c1ccnc(N2CCN(Cc3ccc(F)c(F)c3)C2=O)c1] | 2-(3-(3,4-Difluorobenzyl)-2-oxoimidazolidin-1-yl)-N-(thiazol-2-ylmethyl)-isonicotinamide | mp 105-107° C.; $^1$H NMR (300 MHz, DMSO-d$_6$) δ 9.60 (t, J = 5.7 Hz, 1H), 8.63 (s, 1H), 8.40 (d, J = 5.4 Hz, 1H), 7.71 (d, J = 3.0 Hz, 1H), 7.68 (d, J = 3.0 Hz, 1H), 7.43-7.29 (m, 3H), 7.19-7.15 (m, 1H), 4.72 (d, J = 5.4 Hz, 2H), 4.39 (s, 2H), 3.96 (t, J = 8.0 Hz, 2H), 3.38 (t, J = 8.0 Hz, 2H); MS (ES+) m/z 429.7 (M + 1). |
| 26.26 | 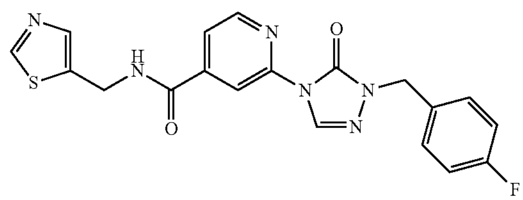 [SMILES: O=C(NCc1cncs1)c1ccnc(-n2cnn(Cc3ccc(F)cc3)c2=O)c1] | 2-(1-(4-Fluorobenzyl)-5-oxo-1H-1,2,4-triazol-4(5H)-yl)-N-(thiazol-5-ylmethyl)-isonicotinamide | mp 181-183° C.; $^1$H NMR (300 MHz, DMSO-d$_6$) δ 9.58 (t, J = 5.7 Hz, 1H), 8.96 (s, 1H), 8.68 (s, 1H), 8.61-8.56 (m, 2H), 7.89 (s, 1H), 7.71 (dd, J = 5.1 Hz, 1.2 Hz, 1H), 7.37-7.32 (m, 2H), 7.18-7.12 (m, 2H), 4.95 (s, 2H), 4.68 (d, J = 5.7 Hz, 2H); MS (ES+) m/z 410.8 (M + 1). |
| 26.27 | 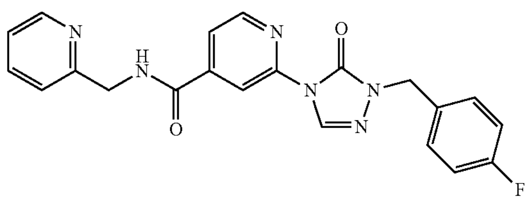 [SMILES: O=C(NCc1ccccn1)c1ccnc(-n2cnn(Cc3ccc(F)cc3)c2=O)c1] | 2-(1-(4-Fluorobenzyl)-5-oxo-1H-1,2,4-triazol-4(5H)-yl)-N-(pyridin-2-ylmethyl)-isonicotinamide | mp 181-183° C.; $^1$H NMR (300 MHz, DMSO-d$_6$) δ 9.51 (t, J = 5.7 Hz, 1H), 8.69 (s, 1H), 8.63-8.59 (m, 2H), 8.49 (d, J = 4.5 Hz, 1H), 7.80-7.71 (m, 2H), 7.37-7.30 (m, 3H), 7.27-7.23 (m, 1H), 7.18-7.12 (m, 2H), 4.96 (s, 2H), 4.57 (d, J = 5.7 Hz, 2H); MS (ES+) m/z 404.9 (M + 1). |
| 26.28 | 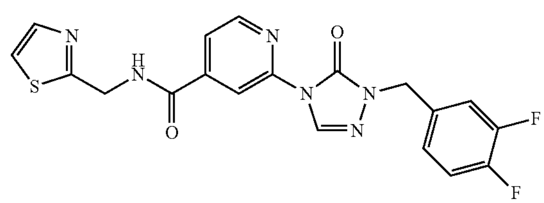 [SMILES: O=C(NCc1nccs1)c1ccnc(-n2cnn(Cc3ccc(F)c(F)c3)c2=O)c1] | 2-(1-(3,4-Difluorobenzyl)-5-oxo-1H-1,2,4-triazol-4(5H)-yl)-N-(thiazol-2-ylmethyl)-isonicotinamide | mp 161-163° C.; $^1$H NMR (300 MHz, DMSO-d$_6$) δ 9.83 (t, J = 5.8 Hz, 1H), 8.74 (s, 1H), 8.67 (d, J = 5.1 Hz, 1H), 8.63 (s, 1H), 7.80 (dd, J = 5.1, 1.2 Hz, 1H), 7.75 (d, J = 3.3 Hz, 1H), 7.66 (d, J = 3.3 Hz, 1H), 7.48-7.38 (m, 2H), 7.21-7.17 (m, 1H), 5.01 (s, 2H), 4.80 (d, J = 5.8 Hz, 2H); MS (ES+) m/z 428.8 (M + 1). |

-continued

| | Structure | Chemical Name | Characterization Data |
|---|---|---|---|
| 26.29 | 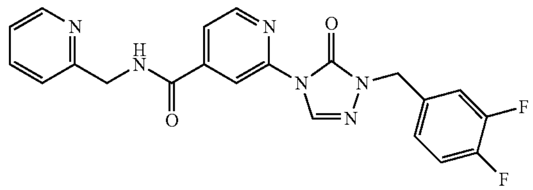 [SMILES: O=C(NCc1ccccn1)c1ccnc(-n2cnn(Cc3ccc(F)c(F)c3)c2=O)c1] | 2-(1-(3,4-Difluorobenzyl)-5-oxo-1H-1,2,4-triazol-4(5H)-yl)-N-(pyridin-2-ylmethyl)-isonicotinamide | $^1$H NMR (300 MHz, DMSO-$d_6$) δ 9.50 (br s, 1H), 8.70-8.48 (m, 4H), 7.81-7.71 (m, 2H), 7.41-7.16 (m, 5H), 4.97 (s, 2H), 4.57 (d, J = 5.1 Hz, 2H); MS (ES+) m/z 422.8 (M + 1). |
| 26.30 | 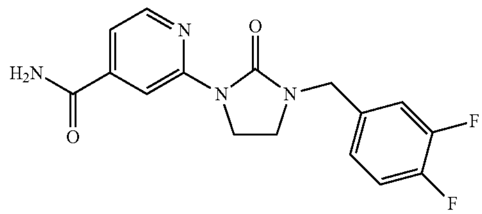 [SMILES: NC(=O)c1ccnc(N2CCN(Cc3ccc(F)c(F)c3)C2=O)c1] | 2-(3-(3,4-Difluorobenzyl)-2-oxoimidazolidin-1-yl)isonicotinamide | mp 195-198° C.; $^1$H NMR (300 MHz, CDCl$_3$) δ 8.67 (s, 1H), 8.38 (d, J = 4.8 Hz, 1H), 7.40 (d, J = 4.8 Hz, 1H), 7.17-7.03 (m, 3H), 6.36 (br s, 1H), 5.82 (br s, 1H), 4.42 (s, 2H), 4.07 (t, J = 8.1 Hz, 2H), 3.40 (t, J = 8.1 Hz, 2H); MS (ES+) m/z 332.8 (M + 1). |
| 26.31 | 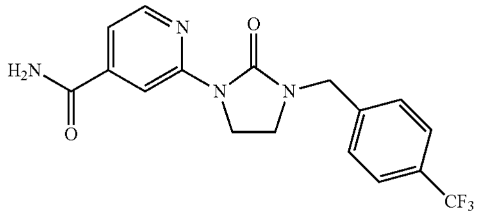 [SMILES: NC(=O)c1ccnc(N2CCN(Cc3ccc(C(F)(F)F)cc3)C2=O)c1] | 2-(2-Oxo-3-(4-(Trifluoromethyl)-benzyl)imidazolidin-1-yl)isonicotinamide | mp 167-169° C.; $^1$H NMR (300 MHz, CDCl$_3$) δ 8.62 (s, 1H), 8.39 (d, J = 4.8 Hz, 1H), 7.66-7.62 (m, 2H), 7.43-7.41 (m, 3H), 6.49 (br s, 1H), 5.83 (br s, 1H), 4.53 (s, 2H), 4.08 (t, J = 8.1 Hz, 2H), 3.41 (t, J = 8.1 Hz, 2H); MS (ES+) m/z 364.8 (M + 1). |
| 26.32 | 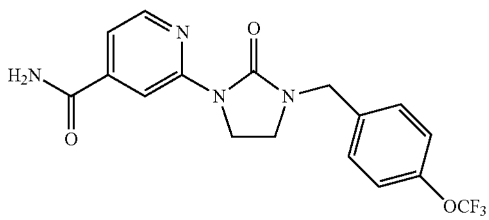 [SMILES: NC(=O)c1ccnc(N2CCN(Cc3ccc(OC(F)(F)F)cc3)C2=O)c1] | 2-(2-Oxo-3-(4-(trifluoromethoxy)-benzyl)imidazolidin-1-yl)isonicotinamide | mp 175-176° C.; $^1$H NMR (300 MHz, CDCl$_3$) δ 8.62 (s, 1H), 8.38 (d, J = 4.2 Hz, 1H), 7.40-7.31 (m, 3H), 7.20-7.17 (m, 2H), 6.52 (br s, 1H), 5.89 (br s, 1H), 4.47 (s, 2H), 4.06 (t, J = 7.6 Hz, 2H), 3.40 (t, J = 7.6 Hz, 2H); MS (ES+) m/z 380.8 (M + 1). |
| 26.33 | 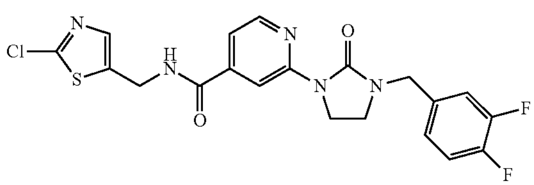 [SMILES: O=C(NCc1cnc(Cl)s1)c1ccnc(N2CCN(Cc3ccc(F)c(F)c3)C2=O)c1] | N-((2-Chlorothiazol-5-yl)methyl)-2-(3-(3,4-difluorobenzyl)-2-oxoimidazolidin-1-yl)isonicotinamide | mp 161-163° C.; $^1$H NMR (300 MHz, CDCl$_3$) δ 8.53 (s, 1H), 8.37 (d, J = 5.1 Hz, 1H), 7.42-7.39 (m, 2H), 7.27-7.24 (m, 1H), 7.16-7.00 (m, 3H), 4.67 (d, J = 5.7 Hz, 2H), 4.39 (s, 2H), 4.06 (t, J = 8.1 Hz, 2H), 3.39 (t, J = 8.1 Hz, 2H); MS (ES+) m/z 463.8 (M + 1), 465.7 (M + 1). |
| 26.34 | 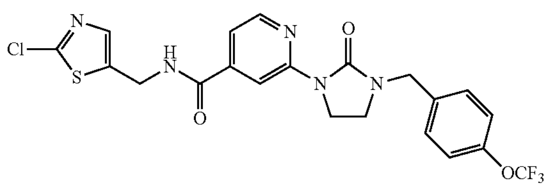 [SMILES: O=C(NCc1cnc(Cl)s1)c1ccnc(N2CCN(Cc3ccc(OC(F)(F)F)cc3)C2=O)c1] | N-((2-Chlorothiazol-5-yl)methyl)-2-(2-oxo-3-(4-(trifluoromethoxy)-benzyl)imidazolidin-1-yl)isonicotinamide | mp 184-186° C.; $^1$H NMR (300 MHz, CDCl$_3$) δ 8.59 (s, 1H), 8.37 (d, J = 4.8 Hz, 1H), 7.43-7.39 (m, 2H), 7.32-7.17 (m, 5H), 4.68 (d, J = 5.4 Hz, 2H), 4.45 (s, 2H), 4.05 (t, J = 8.0 Hz, 2H), 3.40 (t, J = 8.0 Hz, 2H); MS (ES+) m/z 511.8 (M + 1), 513.7 (M + 1). |

Example 27

Measuring Stearoyl-CoA Desaturase Inhibition Activity of a Test Compound Using Mouse Liver Microsomes The identification of compounds of the invention as SCD inhibitors was readily accomplished using the SCD microsomal assay procedure described in Shanklin J. and Summerville C., *Proc. Natl. Acad. Sci. USA* (1991), Vol. 88, pp. 2510-2514.

Preparation of Mouse Liver Microsomes:

Male ICR outbread mice, on a high-carbohydrate, low fat diet, under light halothane (15% in mineral oil) anesthesia are sacrificed by exsanguination during periods of high enzyme activity. Livers are immediately rinsed with cold 0.9% NaCl solution, weighed and minced with scissors. All procedures are performed at 4° C. unless specified otherwise. Livers are homogenized in a solution (1/3 w/v) containing 0.25 M sucrose, 62 mM potassium phosphate buffer (pH 7.0), 0.15 M KCl, 15 mM N-acetyleysteine, 5 mM MgCl$_2$, and 0.1 mM EDTA using 4 strokes of a Potter-Elvehjem tissue homogenizer. The homogenate is centrifuged at 10,400×g for 20 min to eliminate mitochondria and cellular debris. The supernatant is filtered through a 3-layer cheesecloth and centrifuged at 105,000×g for 60 min. The microsomal pellet is gently resuspended in the same homogenization solution with a small glass/teflon homogenizer and stored at −70° C. The absence of mitochondrial contamination is enzymatically assessed. The protein concentration is measured using bovine serum albumin as the standard.

Incubation of Mouse Liver Microsomes with Test Compounds:

Desaturase activity is measured as the release of $^3H_2O$ from [9,10-$^3$H]stearoyl-CoA. Reactions per assay point conditions are as follows: 2 µL 1.5 mM stearoyl-CoA, 0.25 µL 1 mCi/mL $^3$H stearoyl CoA, 10 µL 20 mM NADH, 36.75 µL 0.1 M PK buffer ($K_2HPO_4$/$NaH_2PO_4$, pH 7.2). The test compound or control solution is added in a 1 µL volume. Reactions are started by adding 50 µL of microsomes (1.25 mg/mL). The plates are mixed and after 15 min incubation on a heating block (25° C.), the reactions are stopped by the addition of 10 µL 60% PCA. An aliquot of 100 µL is then transferred to a filter plate pretreated with charcoal and the plate centrifuged at 4000 rpm for 1 minute. The flow through containing the $^3H_2O$ released by the SCD1 desaturation reaction is added to scintillation fluid and the radioactivity measured in a Packard TopCount. The data is analysed to identify the $IC_{50}$ for test compounds and reference compounds.

Representative compounds of the invention showed activity as inhibitors of SCD when tested in this assay. The activity was defined in terms of % SCD enzyme activity remaining at the desired concentration of the test compound or as the $IC_{50}$ concentration. The $IC_{50}$ (affinity) of the example compounds toward the stearoyl-CoA desaturase is comprised between around 20 mM and 0.0001 µM or between around 5 µM and 0.0001 µM or between around 1 µM and 0.0001 µM.

The following Table provides data that exemplifies representative compounds and their Microsomal $IC_{50}$ (µM) data.

| Example | Compound name | Microsomal $IC_{50}$ (µM) |
|---|---|---|
| 6.4 | N-benzyl-2-(3-methoxybenzamido)isonicotinamide | 0.13 |
| 6.8 | N-benzyl-2-(3,5-difluorobenzamido)isonicotinamide | 0.41 |
| 6.11 | N-benzyl-2-(4-(dimethylamino)benzamido)isonicotinamide | 0.02 |
| 10.2 | N-(4-(4-benzyl-1H-imidazol-2-yl)pyridin-2-yl)benzamide | 0.17 |
| 14 | 2-(3-(4-fluorobenzyl)-2-oxoimidazolidin-1-yl)-N-(oxazol-4-ylmethyl)isonicotinamide | 0.20 |
| 14.2 | 2-(3-(4-fluorobenzyl)-2-oxoimidazolidin-1-yl)-N-((5-methylpyrazin-2-yl)methyl)isonicotinamide | 0.08 |
| 14.5 | 2-(3-(4-fluorobenzyl)-2-oxoimidazolidin-1-yl)-N-((1-methyl-1H-imidazol-4-yl)methyl)isonicotinamide | 0.19 |
| 14.10 | 2-(3-(4-fluorobenzyl)-2-oxoimidazolidin-1-yl)-N-((5-methylisoxazol-3-yl)methyl)isonicotinamide | 0.26 |
| 15.3 | of 2-(3-(4-fluorobenzyl)-2-oxoimidazolidin-1-yl)-N-(pyridin-2-ylmethyl)isonicotinamide dihydrochloride | 0.07 |
| 15.4 | N-(4-fluorobenzyl)-2-(3-(4-fluorobenzyl)-2-oxoimidazolidin-1-yl)isonicotinamide | 0.02 |
| 15.11 | 2-(3-(cyclopropylmethyl)-2-oxoimidazolidin-1-yl)-N-(pyridin-4-ylmethyl)isonicotinamide | 0.67 |
| 15.17 | N-(3,4-difluorobenzyl)-2-(2-oxo-3-(pyridin-3-ylmethyl)imidazolidin-1-yl)isonicotinamide | 0.26 |
| 23 | 2-(2-oxo-3-(4-(trifluoromethyl)benzyl)imidazolidin-1-yl)-N-(thiazol-2-ylmethyl)isonicotinamide | 0.01 |
| 24 | 2-(1-(3,4-Difluorobenzyl)-5-oxo-1H-1,2,4-triazol-4(5H)-yl)-N-((5-methylisoxazol-3-yl)methyl)-isonicotinamide | 0.02 |
| 25 | 2-(3-(3,4-Difluorobenzyl)-2-oxoimidazolidin-1-yl)-N-(pyridin-2-ylmethyl)-isonicotinamide | 0.02 |
| 26.12 | 2-(2-Oxo-3-(4-(trifluoromethyl)benzyl)imidazolidin-1-yl)-N-(pyridin-2-ylmethyl)-isonicotinamide | 0.01 |
| 26.13 | N-((5-Methylisoxazol-3-yl)methyl)-2-(2-oxo-3-(4-(trifluoromethoxy)-benzyl)imidazolidin-1-yl)isonicotinamide | 0.01 |
| 26.15 | 2-(2-Oxo-3-(4-(trifluoromethoxy)benzyl)imidazolidin-1-yl)-N-(pyridin-2-ylmethyl)-isonicotinamide | 0.05 |
| 26.18 | N-((5-Methylisoxazol-3-yl)methyl)-2-(2-oxo-3-(4-(trifluoromethyl)-benzyl)imidazolidin-1-yl)isonicotinamide | 0.01 |
| 26.19 | 2-(2-Oxo-3-(4-(trifluoromethyl)benzyl)imidazolidin-1-yl)-N-(thiazol-2-ylmethyl)-isonicotinamide | 0.01 |
| 26.22 | 2-(1-(4-Fluorobenzyl)-5-oxo-1H-1,2,4-triazol-4(5H)-yl)-N-((5-methylisoxazol-3-yl)methyl)-isonicotinamide | 0.01 |
| 26.23 | 2-(3-(3,4-Difluorobenzyl)-2-oxoimidazolidin-1-yl)-N-((5-methylisoxazol-3-yl)methyl)-isonicotinamide | 0.01 |
| 26.27 | 2-(1-(4-Fluorobenzyl)-5-oxo-1H-1,2,4-triazol-4(5H)-yl)-N-(pyridin-2-ylmethyl)-isonicotinamide | 0.12 |
| 26.29 | 2-(1-(3,4-Difluorobenzyl)-5-oxo-1H-1,2,4-triazol-4(5H)-yl)-N-(pyridin-2-ylmethyl)-isonicotinamide | 0.03 |
| 26.30 | 2-(3-(3,4-Difluorobenzyl)-2-oxoimidazolidin-1-yl)isonicotinamide | 1.10 |
| 26.31 | 2-(2-Oxo-3-(4-(Trifluoromethyl)-benzyl)imidazolidin-1-yl)isonicotinamide | 0.18 |
| 26.32 | 2-(2-Oxo-3-(4-(trifluoromethoxy)-benzyl)imidazolidin-1-yl)isonicotinamide | 1.20 |

Those skilled in the art are aware of a variety of modifications to this assay that can be useful for measuring inhibition of stearoyl-CoA desaturase activity in microsomes or in cells by test compounds.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A compound selected from:
   2-(3-(cyclopropylmethyl)-2-oxoimidazolidin-1-yl)-N-(pyridin-2-ylmethyl)isonicotinamide,
   2-(3-(3,4-difluorobenzyl)-2-oxoimidazolidin-1-yl)-N-(pyridin-2-ylmethyl)-isonicotinamide,
   2-(2-oxo-3-(4-(trifluoromethyl)benzyl)imidazolidin-1-yl)-N-(pyridin-2-ylmethyl)-isonicotinamide, and
   2-(2-oxo-3-(4-(trifluoromethoxy)benzyl)imidazolidin-1-yl)-N-(pyridin-2-ylmethyl)-isonicotinamide, or a pharmaceutically acceptable salt thereof.

2. A pharmaceutical composition, comprising:
   the compound of Formula (I) according to claim 1, or a pharmaceutically acceptable salt thereof, and a pharmaceutically acceptable excipient or carrier.

* * * * *